US011691971B2

(12) United States Patent
Shepard et al.

(10) Patent No.: US 11,691,971 B2
(45) Date of Patent: Jul. 4, 2023

(54) NAPHTHYRIDINONE COMPOUNDS AS JAK2 V617F INHIBITORS

(71) Applicant: Incyte Corporation, Wilmington, DE (US)

(72) Inventors: Stacey Shepard, Wilmington, DE (US); Lixin Shao, Wilmington, DE (US); Liangxing Wu, Wilmington, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 69 days.

(21) Appl. No.: 17/350,470

(22) Filed: Jun. 17, 2021

(65) Prior Publication Data

US 2021/0395251 A1    Dec. 23, 2021

Related U.S. Application Data

(60) Provisional application No. 63/041,541, filed on Jun. 19, 2020, provisional application No. 63/043,040, filed on Jun. 23, 2020.

(51) Int. Cl.
*C07D 471/04* (2006.01)
(52) U.S. Cl.
CPC .................................. *C07D 471/04* (2013.01)
(58) Field of Classification Search
CPC ........................................................ C07D 471/04
USPC ....................................................... 514/300
See application file for complete search history.

(56) References Cited

U.S. PATENT DOCUMENTS

| | | | |
|---|---|---|---|
| 4,698,341 A | 10/1987 | Satzinger et al. | |
| 6,339,099 B1 | 1/2002 | Lam et al. | |
| 6,951,865 B2 | 10/2005 | Hibi et al. | |
| 7,429,456 B2 | 9/2008 | Vainchenker et al. | |
| 7,781,199 B2 | 8/2010 | Vainchenker et al. | |
| 7,879,844 B2 | 2/2011 | Inoue et al. | |
| 8,163,767 B2 | 4/2012 | Inoue et al. | |
| 8,524,867 B2 | 9/2013 | Bemett et al. | |
| 8,637,235 B2 | 1/2014 | Vainchenker et al. | |
| 8,785,639 B2 | 7/2014 | Wishart et al. | |
| 8,852,931 B2 | 10/2014 | Vainchenker et al. | |
| 9,115,133 B2 | 8/2015 | Barawkar et al. | |
| 9,233,985 B2 | 1/2016 | Van Zandt et al. | |
| 9,321,730 B2 | 4/2016 | Chan et al. | |
| 9,493,419 B2 | 11/2016 | Tang et al. | |
| 10,065,974 B2 | 9/2018 | Sjogren et al. | |
| 10,155,987 B2 | 12/2018 | Sattler et al. | |
| 10,287,303 B2 | 4/2019 | Sjogren et al. | |
| 10,377,759 B2 | 8/2019 | Yamamoto et al. | |
| 2003/0139431 A1 | 7/2003 | Kawakami et al. | |
| 2004/0209902 A1 | 10/2004 | Lin et al. | |
| 2005/0182060 A1 | 8/2005 | Kelly et al. | |
| 2006/0004043 A1 | 1/2006 | Bhagwat et al. | |
| 2007/0049610 A1 | 3/2007 | Dillon et al. | |
| 2007/0161670 A1 | 7/2007 | Staab et al. | |
| 2008/0004297 A1 | 1/2008 | Cai et al. | |
| 2008/0004318 A1 | 1/2008 | Chelliah et al. | |
| 2008/0188467 A1 | 8/2008 | Wong et al. | |
| 2008/0280879 A1 | 11/2008 | Brickner et al. | |
| 2008/0293739 A1 | 11/2008 | Trede | |
| 2009/0246198 A1 | 10/2009 | Dong et al. | |
| 2010/0105661 A1 | 4/2010 | Shirakami et al. | |
| 2010/0160355 A1 | 6/2010 | DeGoey et al. | |
| 2011/0182812 A1 | 7/2011 | Szardenings et al. | |
| 2011/0269740 A1 | 11/2011 | Sunny et al. | |
| 2011/0313003 A1 | 12/2011 | Shi et al. | |
| 2012/0065188 A1 | 3/2012 | Brickner et al. | |
| 2012/0165370 A1 | 7/2012 | Tang et al. | |
| 2012/0214842 A1 | 8/2012 | Donello et al. | |
| 2012/0282233 A1 | 11/2012 | Rolshausen et al. | |
| 2013/0267521 A1 | 10/2013 | Castro et al. | |
| 2013/0281399 A1 | 10/2013 | McLure et al. | |
| 2013/0302248 A1 | 11/2013 | Gangadharmath et al. | |
| 2014/0142102 A1 | 4/2014 | Fairfax et al. | |
| 2014/0225082 A1 | 8/2014 | Park et al. | |
| 2014/0249204 A1 | 9/2014 | Vainchenker et al. | |
| 2014/0286964 A1 | 9/2014 | Hubbard et al. | |
| 2014/0288048 A1 | 9/2014 | Castro et al. | |
| 2016/0016914 A1 | 1/2016 | Ladziata et al. | |
| 2016/0118600 A1 | 4/2016 | Kim et al. | |
| 2016/0220592 A1 | 8/2016 | Franz et al. | |
| 2017/0107216 A1 | 4/2017 | Wu et al. | |
| 2017/0121346 A1 | 5/2017 | Sprengler et al. | |
| 2017/0145025 A1 | 5/2017 | Li et al. | |
| 2017/0174671 A1 | 6/2017 | Wu et al. | |
| 2017/0174679 A1 | 6/2017 | Lajkiewicz et al. | |
| 2017/0226095 A1 | 8/2017 | Tazi et al. | |
| 2017/0298040 A1 | 10/2017 | Bennett et al. | |

(Continued)

FOREIGN PATENT DOCUMENTS

| | | |
|---|---|---|
| CN | 102838600 | 12/2012 |
| CN | 102838601 | 12/2012 |

(Continued)

OTHER PUBLICATIONS

Atzrodt et al., "The Renaissance of H/D Exchange," Angew Chem Int Ed., 2007, 7744-7765.

Baxter et al., "Acquired mutation of the tyrosine kinase JAK2 in human myeloproliferative disorders," Lancet., 2005, 365:1054-1061.

Bennett et al., "Proposals for the classification of the myelodysplastic syndromes," Br J Haematol., 1982,51:189-199.

Berge et al., "Pharmaceutical Salts," Journal of Pharmaceutical Science, 1977, 66:1-19 pages.

(Continued)

*Primary Examiner* — Niloofar Rahmani
(74) *Attorney, Agent, or Firm* — Fish & Richardson P.C.

(57) ABSTRACT

The present application provides naphthyridinone compounds that modulate the activity of the V617F variant of JAK2, which are useful in the treatment of various diseases, including cancer.

46 Claims, No Drawings
Specification includes a Sequence Listing.

(56) References Cited

U.S. PATENT DOCUMENTS

| | | | |
|---|---|---|---|
| 2017/0320875 | A1 | 11/2017 | Li et al. |
| 2017/0342060 | A1 | 11/2017 | Lu et al. |
| 2017/0362253 | A1 | 12/2017 | Xiao et al. |
| 2018/0016260 | A1 | 1/2018 | Yu et al. |
| 2018/0031557 | A1 | 2/2018 | Scherrer et al. |
| 2018/0086719 | A1 | 3/2018 | Chandrasekhar et al. |
| 2018/0104245 | A1 | 4/2018 | Hansen |
| 2018/0179159 | A1 | 6/2018 | Becknell et al. |
| 2018/0237797 | A1 | 8/2018 | Loh |
| 2019/0152913 | A1 | 5/2019 | Becknell et al. |
| 2019/0152988 | A1 | 5/2019 | Sprengler et al. |
| 2019/0256492 | A1 | 8/2019 | Tu et al. |
| 2021/0395257 | A1 | 12/2021 | Yu et al. |
| 2022/0002299 | A1 | 1/2022 | Liu et al. |
| 2022/0064165 | A1 | 3/2022 | Liu et al. |
| 2022/0169649 | A1 | 6/2022 | Ai et al. |
| 2022/0213108 | A1 | 7/2022 | Buesking et al. |
| 2022/0281887 | A1 | 9/2022 | Shepard et al. |

FOREIGN PATENT DOCUMENTS

| | | | |
|---|---|---|---|
| CN | 104311426 | | 1/2015 |
| CN | 104725249 | | 6/2015 |
| CN | 105461714 | | 4/2016 |
| CN | 105481765 | | 4/2016 |
| CN | 105732591 | | 7/2016 |
| CN | 109575022 | | 4/2019 |
| CN | 109608504 | | 4/2019 |
| CN | 111484480 | * | 1/2020 |
| CN | 111484480 | | 8/2020 |
| EP | 0329012 | | 8/1989 |
| EP | 0481448 | | 4/1992 |
| EP | 0652218 | | 5/1995 |
| EP | 1692281 | | 10/2005 |
| EP | 2309567 | | 10/2010 |
| EP | 3277293 | | 2/2018 |
| EP | 3277820 | | 2/2018 |
| EP | 3578555 | | 12/2019 |
| FR | 2996129 | | 4/2014 |
| JP | 62209062 | | 9/1987 |
| JP | 07089957 | | 4/1995 |
| JP | 2000123973 | | 4/2000 |
| JP | 2003107641 | | 4/2003 |
| JP | 2004196702 | | 7/2004 |
| KR | 20140111166 | | 9/2014 |
| KR | 20150002266 | | 1/2015 |
| KR | 20160123112 | | 10/2016 |
| KR | 20170003469 | | 6/2017 |
| WO | WO 93/17681 | | 9/1993 |
| WO | WO 93/17682 | | 9/1993 |
| WO | WO 95/18127 | | 7/1995 |
| WO | WO 97/34893 | | 9/1997 |
| WO | WO 97/47601 | | 12/1997 |
| WO | WO 98/16184 | | 4/1998 |
| WO | WO 98/40373 | | 9/1998 |
| WO | WO 99/61444 | | 12/1999 |
| WO | WO 99/64400 | | 12/1999 |
| WO | WO 2000/041695 | | 7/2000 |
| WO | WO 2000/067754 | | 11/2000 |
| WO | WO 2000/068230 | | 11/2000 |
| WO | WO 2001/023389 | | 4/2001 |
| WO | WO 2001/042247 | | 6/2001 |
| WO | WO 2001/047891 | | 7/2001 |
| WO | WO 2001/058899 | | 8/2001 |
| WO | WO 2001/070229 | | 9/2001 |
| WO | WO 2002/000196 | | 1/2002 |
| WO | WO 2002/091830 | | 11/2002 |
| WO | WO 2003/062209 | | 7/2003 |
| WO | WO 2003/074045 | | 9/2003 |
| WO | WO 2004/014866 | | 2/2004 |
| WO | WO 2004/024693 | | 3/2004 |
| WO | WO 2004/030635 | | 4/2004 |
| WO | WO 2004/031161 | | 4/2004 |
| WO | WO 2004/039806 | | 5/2004 |
| WO | WO 2004/055004 | | 7/2004 |
| WO | WO 2004/080463 | | 9/2004 |
| WO | WO 2005/003100 | | 1/2005 |
| WO | WO 2005/007658 | | 1/2005 |
| WO | WO 2005/009967 | | 2/2005 |
| WO | WO 2005/028478 | | 3/2005 |
| WO | WO 2005/061460 | | 7/2005 |
| WO | WO 2005/072412 | | 8/2005 |
| WO | WO 2005/080377 | | 9/2005 |
| WO | WO 2005/082367 | | 9/2005 |
| WO | WO 2005/110410 | | 11/2005 |
| WO | WO 2005/112932 | | 12/2005 |
| WO | WO 2005/117890 | | 12/2005 |
| WO | WO 2005/121138 | | 12/2005 |
| WO | WO 2006/021448 | | 3/2006 |
| WO | WO 2006/032470 | | 3/2006 |
| WO | WO 2006/039718 | | 4/2006 |
| WO | WO 2006/045096 | | 4/2006 |
| WO | WO 2006/045827 | | 5/2006 |
| WO | WO 2006/065842 | | 6/2006 |
| WO | WO 2006/072828 | | 7/2006 |
| WO | WO 2006/074147 | | 7/2006 |
| WO | WO 2006/108107 | | 10/2006 |
| WO | WO 2006/122156 | | 11/2006 |
| WO | WO 2007/002781 | | 1/2007 |
| WO | WO 2007/007919 | | 1/2007 |
| WO | WO 2007/016525 | | 2/2007 |
| WO | WO 2007/022946 | | 3/2007 |
| WO | WO 2007/038209 | | 4/2007 |
| WO | WO 2007/047653 | | 4/2007 |
| WO | WO 2007/051062 | | 5/2007 |
| WO | WO 2007/076092 | | 5/2007 |
| WO | WO 2007/077949 | | 7/2007 |
| WO | WO 2007/110868 | | 10/2007 |
| WO | WO 2007/112347 | | 10/2007 |
| WO | WO 2007/113565 | | 10/2007 |
| WO | WO 2007/125405 | | 11/2007 |
| WO | WO 2007/133637 | | 11/2007 |
| WO | WO 2007/136465 | | 11/2007 |
| WO | WO 2007/140222 | | 12/2007 |
| WO | WO 2007/147217 | | 12/2007 |
| WO | WO 2008/000409 | | 1/2008 |
| WO | WO 2008/005956 | | 1/2008 |
| WO | WO 2008/007127 | | 1/2008 |
| WO | WO 2008/011109 | | 1/2008 |
| WO | WO 2008/011174 | | 1/2008 |
| WO | WO 2008/021924 | | 2/2008 |
| WO | WO 2008/024977 | | 2/2008 |
| WO | WO 2008/046919 | | 4/2008 |
| WO | WO 2008/060090 | | 5/2008 |
| WO | WO 2008/064107 | | 5/2008 |
| WO | WO 2008/079965 | | 7/2008 |
| WO | WO 2008/084861 | | 7/2008 |
| WO | WO 2008/092231 | | 8/2008 |
| WO | WO 2008/112217 | | 9/2008 |
| WO | WO 2008/113558 | | 9/2008 |
| WO | WO 2008/124083 | | 10/2008 |
| WO | WO 2008/135524 | | 11/2008 |
| WO | WO 2008/151184 | | 12/2008 |
| WO | WO 2009/024095 | | 2/2009 |
| WO | WO 2009/042970 | | 4/2009 |
| WO | WO 2009/114512 | | 9/2009 |
| WO | WO 2010/006130 | | 1/2010 |
| WO | WO 2010/026771 | | 3/2010 |
| WO | WO 2010/039518 | | 4/2010 |
| WO | WO 2010/042684 | | 4/2010 |
| WO | WO 2010/077947 | | 7/2010 |
| WO | WO 2010/078229 | | 7/2010 |
| WO | WO 2010/080537 | | 7/2010 |
| WO | WO 2010/101949 | | 9/2010 |
| WO | WO 2010/106436 | | 9/2010 |
| WO | WO 2010/107765 | | 9/2010 |
| WO | WO 2010/107768 | | 9/2010 |
| WO | WO 2010/123975 | | 10/2010 |
| WO | WO 2010/125350 | | 11/2010 |
| WO | WO 2010/129816 | | 11/2010 |
| WO | WO 2010/141062 | | 12/2010 |
| WO | WO 2010/143168 | | 12/2010 |
| WO | WO 2010/143169 | | 12/2010 |
| WO | WO 2010/143170 | | 12/2010 |

(56) References Cited

FOREIGN PATENT DOCUMENTS

| | | |
|---|---|---|
| WO | WO 2011/004276 | 1/2011 |
| WO | WO 2011/022439 | 2/2011 |
| WO | WO 2011/028864 | 3/2011 |
| WO | WO 2011/047432 | 4/2011 |
| WO | WO 2011/050245 | 4/2011 |
| WO | WO 2011/053861 | 5/2011 |
| WO | WO 2011/068899 | 6/2011 |
| WO | WO 2011/072275 | 6/2011 |
| WO | WO 2011/075630 | 6/2011 |
| WO | WO 2011/078143 | 6/2011 |
| WO | WO 2011/078369 | 6/2011 |
| WO | WO 2011/086053 | 7/2011 |
| WO | WO 2011/097717 | 8/2011 |
| WO | WO 2011/103557 | 8/2011 |
| WO | WO 2011/112687 | 9/2011 |
| WO | WO 2011/123693 | 10/2011 |
| WO | WO 2011/137428 | 11/2011 |
| WO | WO 2011/146882 | 11/2011 |
| WO | WO 2012/061696 | 5/2012 |
| WO | WO 2012/066578 | 5/2012 |
| WO | WO 2012/078902 | 6/2012 |
| WO | WO 2012/085176 | 6/2012 |
| WO | WO 2012/089828 | 7/2012 |
| WO | WO 2012/097479 | 7/2012 |
| WO | WO 2012/116237 | 8/2012 |
| WO | WO 2012/127506 | 9/2012 |
| WO | WO 2013/007765 | 1/2013 |
| WO | WO 2013/033093 | 3/2013 |
| WO | WO 2013/033268 | 3/2013 |
| WO | WO 2013/033270 | 3/2013 |
| WO | WO 2013/033981 | 3/2013 |
| WO | WO 2013/049352 | 4/2013 |
| WO | WO 2013/062987 | 5/2013 |
| WO | WO 2013/067036 | 5/2013 |
| WO | WO 2013/086229 | 6/2013 |
| WO | WO 2013/156869 | 10/2013 |
| WO | WO 2013/158928 | 10/2013 |
| WO | WO 2013/167653 | 11/2013 |
| WO | WO 2013/175281 | 11/2013 |
| WO | WO 2013/191112 | 12/2013 |
| WO | WO 2014/018891 | 1/2014 |
| WO | WO 2014/023377 | 2/2014 |
| WO | WO 2014/051653 | 4/2014 |
| WO | WO 2014/074580 | 5/2014 |
| WO | WO 2014/087165 | 6/2014 |
| WO | WO 2014/120764 | 8/2014 |
| WO | WO 2014/203152 | 12/2014 |
| WO | WO 2014/204263 | 12/2014 |
| WO | WO 2015/001518 | 1/2015 |
| WO | WO 2015/009812 | 1/2015 |
| WO | WO 2015/025228 | 2/2015 |
| WO | WO 2015/036560 | 3/2015 |
| WO | WO 2015/049022 | 4/2015 |
| WO | WO 2015/086523 | 6/2015 |
| WO | WO 2015/124063 | 8/2015 |
| WO | WO 2015/144001 | 10/2015 |
| WO | WO 2015/168079 | 11/2015 |
| WO | WO 2016/009076 | 1/2016 |
| WO | WO 2016/116900 | 7/2016 |
| WO | WO 2016/123627 | 8/2016 |
| WO | WO 2016/128465 | 8/2016 |
| WO | WO 2016/160860 | 10/2016 |
| WO | WO 2016/190847 | 12/2016 |
| WO | WO 2016/197027 | 12/2016 |
| WO | WO 2017/003723 | 1/2017 |
| WO | WO 2017/004134 | 1/2017 |
| WO | WO 2017/029601 | 2/2017 |
| WO | WO 2017/059319 | 4/2017 |
| WO | WO 2017/072039 | 5/2017 |
| WO | WO 2017/072283 | 5/2017 |
| WO | WO 2017/075394 | 5/2017 |
| WO | WO 2017/090002 | 6/2017 |
| WO | WO 2017/103931 | 6/2017 |
| WO | WO 2017/205538 | 11/2017 |
| WO | WO 2017/223452 | 12/2017 |
| WO | WO 2018/009622 | 1/2018 |
| WO | WO 2018/046933 | 3/2018 |
| WO | WO 2018/057805 | 3/2018 |
| WO | WO 2018/068017 | 4/2018 |
| WO | WO 2018/083098 | 5/2018 |
| WO | WO 2018/112382 | 6/2018 |
| WO | WO 2018/140512 | 8/2018 |
| WO | WO 2018/140600 | 8/2018 |
| WO | WO 2018/144478 | 8/2018 |
| WO | WO 2018/204176 | 11/2018 |
| WO | WO 2018/204765 | 11/2018 |
| WO | WO 2018/222901 | 12/2018 |
| WO | WO 2018/231745 | 12/2018 |
| WO | WO 2018/237370 | 12/2018 |
| WO | WO 2019/060860 | 3/2019 |
| WO | WO 2019/070492 | 4/2019 |
| WO | WO 2019/129213 | 7/2019 |
| WO | WO 2019/135920 | 7/2019 |
| WO | WO 2019/177975 | 9/2019 |
| WO | WO 2019/201283 | 10/2019 |
| WO | WO 2019/214546 | 11/2019 |
| WO | WO 2021/018012 | 2/2021 |

OTHER PUBLICATIONS

Blom et al., "Preparative LC-MS Purification: Improved Compound Specific Method Optimization," J Combi Chem., 2004, 2004, 6:874-883.

Blom et al., "Optimizing Preparative LC-MS Configurations and Methods for Parallel Synthesis Purification," J Combi Chem., 2003, 5:670.

Blom et al., "Two-Pump at Column Dilution Configuration for Preparative Lc-Ms," J Combi Chem., 2002, 4:295.

Brunning et al., "Myelodysplastic syndromes/neoplasms," in Chapter 5, Swerdlow, et al., eds. WHO Classification of Tumours of Haematopoietic and Lymphoid Tissues., 4th edition, 21 pages.

Ceesay et al., "The JAK2 V617F mutation is rare in RARS but common in RARS-T," Leukemia, 2006, 20:2060-2061.

Dommaraju et al., "An efficient catalyst-free chemoselective multicomponent reaction for the synthesis of pyrimidine functionalized pyrrolo-annelated derivatives," RSC Adv., Jan. 1, 2015, 5:24327-24335.

Eisenhauer et al., "New response evaluation criteria in solid tumours: Revised RECIST guideline (version 1.1)," European Journal of Cancer, Jan. 2009, 45(2):228-247.

Harris et al., "World Health Organization classification of neoplastic diseases of the hematopoietic and lymphoid tissues: report of the Clinical Advisory Committee meeting—Airlie House, Virginia, Nov. 1997," J Clin Oncol., 1999, 17:3835-3849.

Hart et al., "Structure-Based Design of Selective Janus Kinase 2 Imidazo[4,5-d]pyrrolo[2,3-b]pyridine Inhibitors," ACS Med Chem Lett., Aug. 13, 2015, 6(8):845-849.

International Search Report and Written Opinion in International Appln. No. PCT/US2021/037870, dated Aug. 13, 2021, 13 pages.

International Search Report and Written Opinion in International Appln. No. PCT/US2021/037877, dated Aug. 13, 2021, 10 pages.

International Search Report and Written Opinion in International Appln. No. PCT/US2021/040182, dated Sep. 22, 2021, 12 pages.

International Search Report and Written Opinion in International Appln. No. PCT/US2021/040185, dated Sep. 22, 2021, 15 pages.

International Search Report and Written Opinion in International Appln. No. PCT/US2021/047687, dated Nov. 19, 2021, 16 pages.

International Search Report and Written Opinion in International Appln. No. PCT/US2021/064295, dated Mar. 17, 2022, 15 pages.

International Search Report and Written Opinion in International Appln. No. PCT/US2022/017654, dated May 30, 2022, 22 pages.

James et al., "A unique clonal JAK2 mutation leading to constitutive signalling causes polycythaemia vera," Nature, 2005, 434:1144-1148.

Jisha et al., "Exploration of 3,6-dihydroimidazo(4,5-d)pyrrolo(2,3-b)pyridin-2(1H)-one derivatives as JAK inhibitors using various in silico techniques," In Silico Pharmacology, 2017, 5(1):1-23.

Kerekes et al., "Aurora kinase inhibitors based on the imidazo[1,2-a]pyrazine core: fluorine and deuterium incorporation improve oral absorption and exposure," J Med Chem., 2011, 54:201-210.

(56) References Cited

OTHER PUBLICATIONS

Khalaf et al., "Structure-based design and synthesis of antiparasitic pyrrolopyrimidines targeting pteridine reductase 1," J Med Chem., Jul. 9, 2014, 57(15):6479-6494.

Kralovics et al., "A gain-of-function mutation of JAK2 in myeloproliferative disorders," N Engl J Med., 2005, 352:1779-1790.

Kulagawski et al., "Identification of imidazo-pyrrolopyridines as novel and potent JAK1 inhibitors," J Med Chem., 2012, 55(12):5901-5921.

Labadie et al., "Design and evaluation of novel 8-oxo-pyridopyrimidine Jak1/2 inhibitors," Bioorg Med Chem Lett., Nov. 2013, 23(21):5923-5930.

Leroy et al., "Differential effect of inhibitory strategies of the V617 mutant of JAK2 on cytokine receptor signaling," Journal of Allergy and Clinical Immunology, Jul. 2019, 144(1):224-235.

Levine et al., "Activating mutation in the tyrosine kinase JAK2 in polycythemia vera, essential thrombocythemia, and myeloid metaplasia with myelofibrosis," Cancer Cell., 2005, 7:387-397.

Ma et al., "Mutation Profile of JAK2 Transcripts in Patients with Chronic Myeloproliferative Neoplasias," J. Mol. Diagn., Jan. 2009, 11(1):49-53.

Remington's Pharmaceutical Sciences, 17th ed., Mack Publishing Company, Easton, Pa., 1985, p. 1418.

STN Search Report, Conducted Dec. 10, 2019, 379 pages.
STN Search Report, Conducted Dec. 2019, 1 page.
STN Search Report, Conducted Dec. 2020, 11 pages.
STN Search Report, Conducted Jun. 19, 2021, 236 pages.
STN Search Report, Conducted Jun. 2019, 316 pages.
STN Search Report, Conducted Jun. 2019, 292 pages.
STN Search Report, Conducted Jun. 2019, 13 pages.
STN Search Report, Conducted Jun. 2019, 39 pages.
STN Search Report, Conducted Oct. 2019, 14 pages.
STN Search Report, Conducted Sep. 2019, 236 pages.
STN Search Report, Conducted Sep. 2019, 5 pages.

Vainchecker et al., "JAK inhibitors for the treatment of myeloproliferative neoplasms and other disorders," F1000Research., 2018, 7:82.

Vardiman et al., "The 2008 revision of the World Health Organization (WHO) classification of myeloid neoplasms and acute leukemia: rationale and important changes," Blood 2009, 114:937-951.

Vardiman et al., "The World Health Organization (WHO) classification of the myeloid neoplasms," Blood 2002, 100:2292-2302.

Wilmes et al., "Mechanism of homodimeric cytokine receptor activation and dysregulation by oncogenic mutations," Science, 2020, 367:643-652.

Woods et al., "Activation of JAK/STAT Signaling in Megakaryocytes Sustains Myeloproliferation In Vivo," Clin Cancer Res., 2019, 25(19):5901-5912.

Xu et al., "Design, synthesis and biological evaluation of deuterated nintedanib for improving pharmacokinetic properties," J Label Compd Radiopharm., 2015, 58:308-312.

Yamagishi et al., "Discovery of 3,6-dihydroimidazo[4,5-d]pyrrolo[2,3-b]pyridin-2(1H)-one derivatives as novel JAK inhibitors," Biorg & Med Chem., 2015, 23(15):4846-4859.

Yamagishi et al., "Discovery of tricyclic dipyrrolopyridine derivatives as novel JAK inhibitors," Biorg & Med Chem, 2017, 25(20):5311-5326.

Yang et al., "Three-component reaction for synthesis of 2-amino-6-aryl-5-(phenylamino)-3,7-dihydro-4H-pyrrolo[2,3-d]pyrimidin-4-one derivatives in water," J Hetero Chem., Sep. 2020, 57(9):3271-3278.

Zak et al., "Discovery and optimization of C-2 methyl imidazopyrrolopyridines as potent and orally bioavailable JAK1 inhibitors with selectivity over JAK2," J Med Chem., 2012, 55(13):6176-6193.

Dommaraju et al., "An efficient catalyst-free chemoselective multicomponent reaction for the synthesis of pyrimidine functionalized pyrrolo-annelated derivatives," Electronic Supplementary Information for RSC Adv., Jan. 1, 2015, 64 pages.

International Preliminary Report on Patentability in International Application No. PCT/US2021/037870, dated Dec. 29, 2022, 8 pages.

International Preliminary Report on Patentability in International Application No. PCT/US2021/037877, dated Dec. 29, 2022, 8 pages.

International Preliminary Report on Patentability in International Application No. PCT/US2021/040182, dated Jan. 12, 2023, 8 pages.

International Preliminary Report on Patentability in International Application No. PCT/US2021/040185, dated Jan. 12, 2023, 8 pages.

Quiroga et al., "Generation of pyrrolo[2,3-d]pyrimidines. Unexpected products in the multicomponent reaction of 6-aminopyrimidines, dimedone, and arylglyoxal," Tetrahedron Letters, Oct. 2010, 51(41):5443-5447.

Scott et al., "JAK2 Exon 12 Mutations in Polycythemia Vera and Idiopathic Erythrocytosis," The New England Journal of Medicine, Feb. 1, 2007, 356:459-68.

* cited by examiner

NAPHTHYRIDINONE COMPOUNDS AS JAK2 V617F INHIBITORS

TECHNICAL FIELD

The present invention provides naphthyridinone compounds that modulate the activity of the V617F variant of JAK2 and are useful in the treatment of diseases related to the V617F variant of JAK2, including cancer.

SEQUENCE LISTING

This application contains a Sequence Listing that has been submitted electronically as an ASCII text file named Sequence Listing. The ASCII text file, created on Aug. 30, 2021, is 600 kilobytes in size. The material in the ASCII text file is hereby incorporated by reference in its entirety.

BACKGROUND

Janus kinase (JAK) 2 plays pivotal roles in signaling by several cytokine receptors. The mutant JAK2 V617F is the most common molecular event associated with myeloproliferative neoplasms. Selective targeting of the JAK2 V617F mutant may be useful for treating various pathologies, while sparing essential JAK2 functions. This application is directed to this need and others.

SUMMARY

The present invention related to, inter alia, compounds of Formula F

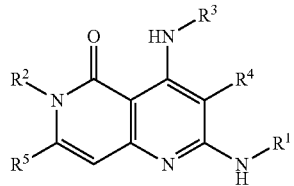

or pharmaceutically acceptable salts, wherein constituent members are defined herein.

The present invention further provides pharmaceutical compositions comprising a compound of Formula I, or a pharmaceutically acceptable salt thereof, and a pharmaceutically acceptable carrier.

The present invention further provides methods of inhibiting an activity of the V617F variant of JAK2 kinase comprising contacting the kinase with a compound of Formula I, or a pharmaceutically acceptable salt thereof.

The present invention further provides methods of treating a disease or a disorder associated with expression or activity of the V617F variant of JAK2 kinase in a patient by administering to a patient a therapeutically effective amount of a compound of Formula I, or a pharmaceutically acceptable salt thereof.

The present invention further provides a compound of Formula I, or a pharmaceutically acceptable salt thereof, for use in any of the methods described herein.

The present invention further provides use of a compound of Formula I, or a pharmaceutically acceptable salt thereof, for the preparation of a medicament for use in any of the methods described herein.

DETAILED DESCRIPTION

The present application provides compounds of Formula I:

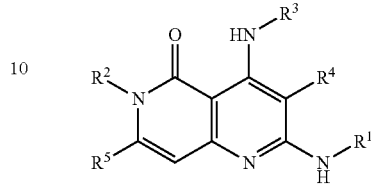

or a pharmaceutically acceptable salt thereof, wherein:

$R^1$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a1}$, $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{14}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{c1}$ and $R^{d1}$ are each optionally substituted with 1, 2, 3, 4, 5, 6, 7, or 8 independently selected $R^{14}$ substituents;

or, any $R^{c1}$ and $R^{d1}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{14}$ substituents;

each $R^{b1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b1}$ are each optionally substituted with 1, 2, 3, 4, 5, 6, 7, or 8 independently selected $R^{14}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{1A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)R^{b11}$, $NR^{c11}S(O)NR^{c11}R^{d11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, $OS(O)_2R^{b11}$, $SF_5$, $P(O)R^{f11}R^{g11}$, $OP(O)(OR^{h11})(OR^{i11})$, $P(O)(OR^{h11})(OR^{i11})$, and $BR^{j11}R^{k11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, 4, 5, 6, 7, or 8 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{c11}$ and $R^{d11}$ are each optionally substituted with 1, 2, 3, 4, 5, 6, 7, or 8 independently selected $R^{1B}$ substituents;

or, any $R^{c11}$ and $R^{d11}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{1B}$ substituents;

each $R^{b11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b11}$ are each optionally substituted with 1, 2, 3, 4, 5, 6, 7, or 8 independently selected $R^{1B}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{c11}$ and $R^{g11}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h11}$ and $R^{i11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j11}$ and $R^{k11}$ is independently selected from OH, $C_{1-6}$ alkoxy, and $C_{1-6}$ haloalkoxy;

or any $R^{j11}$ and $R^{k11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1B}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)NR^{c12}R^{d12}$, $C(=NR^{e12})R^{b12}$, $C(=NR^{e12})NR^{c12}R^{d12}$, $NR^{c12}C(=NR^{e12})NR^{c12}R^{d12}$, $NR^{c12}C(=NR^{e12})R^{b12}$, $NR^{c12}S(O)R^{b12}$, $NR^{c12}S(O)NR^{c12}R^{d12}$, $NR^{c12}S(O)_2R^{b12}$, $NR^{c12}S(O)(=NR^{e12})R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, $OS(O)(=NR^{e12})R^{b12}$, and $OS(O)_2R^{b12}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{1B}$ are each optionally substituted with 1, 2, 3, or 4 independently selected $R^{M}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{a12}$, $R^{c12}$ and $R^{d12}$ are each optionally substituted with 1, 2, 3, or 4 independently selected $R^{M}$ substituents;

or, any $R^{c12}$ and $R^{d12}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^{M}$ substituents;

each $R^{b12}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{b12}$ are each optionally substituted with 1, 2, 3, or 4 independently selected $R^M$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

$R^2$ is selected from H, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $C(=NR^{e2})R^{b2}$, $C(=NR^{e2})NR^{c2}R^{d2}$, $NR^{c2}R^{d2}$, $S(O)R^{b2}$, $S(O)NR^{c2}R^{d2}$, $S(O)_2R^{b2}$, and $S(O)_2NR^{c2}R^{d2}$, wherein the $C_{1-6}$ alkyl, $C_{2-6}$ alkenyl, and $C_{2-6}$ alkynyl of $R^2$ are each optionally substituted with 1, 2, 3, 4, 5, 6, 7, or 8 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, of $R^{a2}$, $R^{c2}$ and $R^{d2}$ are each optionally substituted with 1, 2, 3, 4, 5, 6, 7, or 8 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{2A}$ is independently selected from D, halo, oxo, $C_{1-6}$ alkyl, $C_{1-6}$ haloalkyl, $C_{2-6}$ alkenyl, $C_{2-6}$ alkynyl, CN, $NO_2$, $OR^{a21}$, $C(O)R^{b21}$, $C(O)NR^{c21}R^{d21}$, $C(O)OR^{a21}$, $C(=NR^{e21})R^{b21}$, $C(=NR^{e21})NR^{c21}R^{d21}$, $S(O)R^{b21}$, $S(O)NR^{c21}R^{d21}$, $S(O)_2R^{b21}$, and $S(O)_2NR^{c21}R^{d21}$, wherein the $C_{1-6}$ alkyl, $C_{2-6}$ alkenyl, and $C_{2-6}$ alkynyl of $R^{2A}$ are each optionally substituted with 1, 2, 3, or 4 independently selected $R^M$ substituents;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, of $R^{a21}$, $R^{c21}$ and $R^{d21}$ are each optionally substituted with 1, 2, 3, or 4 independently selected $R^M$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

$R^3$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a3}$, $C(O)R^{b3}$, $C(O)NR^{c3}R^{d3}$, $C(O)OR^{a3}$, $C(=NR^{e3})R^{b3}$, $C(=NR^{e3})NR^{c3}R^{d3}$, $S(O)R^{b3}$, $S(O)NR^{c3}R^{d3}$, $S(O)_2R^{b3}$, and $S(O)_2NR^{c3}R^{d3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, 4, 5, 6, 7, or 8 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, 4, 5, 6, 7, or 8 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, 4, 5, 6, 7, or 8 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $NHOR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}NR^{c31}R^{d31}$, $NR^{c31}C(O)R^{b31}$, $NR^{c31}C(O)OR^{a31}$, $NR^{c31}C(O)NR^{c31}R^{d31}$, $C(=NR^{e31})R^{b31}$, $C(=NR^{e31})NR^{c31}R^{d31}$, $NR^{c31}C(=NR^{e31})NR^{c31}R^{d31}$, $NR^{c31}C(=NR^{e31})R^{b31}$, $NR^{c31}S(O)R^{b31}$, $NR^{c31}S(O)NR^{c31}R^{d31}$, $NR^{c31}S(O)_2R^{b31}$, $NR^{c31}S(O)(=NR^{e31})R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, $OS(O)(=NR^{e31})R^{b31}$, $OS(O)_2R^{b31}$, $SF_5$, $P(O)R^{f31}R^{g31}$, $OP(O)(OR^{h31})(OR^{i31})$, $P(O)(OR^{h31})(OR^{i31})$, and $BR^{j31}R^{k31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, 4, 5, 6, 7, or 8 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, 4, 5, 6, 7, or 8 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, 4, 5, 6, 7, or 8 independently selected $R^{3B}$ substituents;

each $R^{e31}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f31}$ and $R^{g31}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h31}$ and $R^{i31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j31}$ and $R^{k31}$ is independently selected from OH, $C_{1-6}$ alkoxy, and $C_{1-6}$ haloalkoxy;

or any $R^{j31}$ and $R^{k31}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{3B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $NHOR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}NR^{c32}R^{d32}$, $NR^{c32}C(O)R^{b32}$, $NR^{c32}C(O)OR^{a32}$, $NR^{c32}C(O)NR^{c32}R^{d32}$, $C(=NR^{e32})R^{b32}$, $C(=NR^{e32})NR^{c32}R^{d32}$, $NR^{c32}C(=NR^{e32})NR^{c32}R^{d32}$, $NR^{c32}C(=NR^{e32})R^{b32}$, $NR^{c32}S(O)R^{b32}$, $NR^{c32}S(O)NR^{c32}R^{d32}$, $NR^{c32}S(O)_2R^{b32}$, $NR^{c32}S(O)(=NR^{e32})R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, $OS(O)R^{b32}$, $OS(O)(=NR^{e32})R^{b32}$, $OS(O)_2R^{b32}$, $SF_5$, $P(O)R^{f32}R^{g32}$, $OP(O)(OR^{h32})(OR^{i32})$, $P(O)(OR^{h32})(OR^{i32})$, and $BR^{j32}R^{k32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, 4, 5, 6, 7, or 8 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, 4, 5, 6, 7, or 8 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, 4, 5, 6, 7, or 8 independently selected $R^{3C}$ substituents;

each $R^{e32}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocyclo alkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f32}$ and $R^{g32}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h32}$ and $R^{i32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j32}$ and $R^{k32}$ is independently selected from OH, $C_{1-6}$ alkoxy, and $C_{1-6}$ haloalkoxy;

or any $R^{j32}$ and $R^{k32}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{3C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $NHOR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}NR^{c33}R^{d33}$, $NR^{c33}C(O)R^{b33}$, $NR^{c33}C(O)OR^{a33}$, $NR^{c33}C(O)NR^{c33}R^{d33}$, $C(=NR^{e33})R^{b33}$, $C(=NR^{e33})NR^{c33}R^{d33}$, $NR^{c33}C(=NR^{e33})NR^{c33}R^{d33}$, $NR^{c33}C(=NR^{e33})R^{b33}$, $NR^{c33}S(O)R^{b33}$, $NR^{c33}S(O)NR^{c33}R^{d33}$, $NR^{c33}S(O)_2R^{b33}$, $NR^{c33}S(O)(=NR^{e33})R^{b33}$, $NR^{c33}S(O)_2NR^{c33}R^{d33}$, $S(O)R^{b33}$, $S(O)NR^{c33}R^{d33}$, $S(O)_2R^{b33}$, $S(O)_2NR^{c33}R^{d33}$, $OS(O)(=NR^{e33})R^{b33}$, and $OS(O)_2R^{b33}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{3C}$ are each optionally substituted with 1, 2, 3, or 4 independently selected $R^M$ substituents;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a33}$, $R^{c33}$ and $R^{d33}$ are each optionally substituted with 1, 2, 3, or 4 independently selected $R^M$ substituents;

or, any $R^{c33}$ and $R^{d33}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b33}$ are each optionally substituted with 1, 2, 3, or 4 independently selected $R^M$ substituents;

each $R^{e33}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$;

$R^5$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$; and each $R^M$ is independently selected from H, D, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments:

$R^1$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a1}$, $C(O)R^{b1}$, $C(O)NR^{c1}R^{d1}$, and $C(O)OR^{a1}$;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

or, any $R^{c1}$ and $R^{d1}$ attached to the same N atom, together with the N atom to which they are attached, form a 5-10 membered heteroaryl or a 4-10 membered heterocycloalkyl group;

each $R^{b1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

$R^2$ is selected from H, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, of $R^{a2}$, $R^{c2}$ and $R^{d2}$ are each optionally substituted with 1, 2, 3, 4, 5, 6, 7, or 8 independently selected $R^{2A}$ substituents;

$R^3$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a3}$, $C(O)R^{b3}$, $C(O)NR^{c3}R^{d3}$, $C(O)OR^{a3}$, $S(O)R^{b3}$, $S(O)NR^{c3}R^{d3}$, $S(O)_2R^{b3}$, and $S(O)_2NR^{c3}R^{d3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, or 4 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, or 4 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1}$-6 alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, or 4 independently selected $R^{3A}$ substituents;

each $R^{3A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $NHOR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}NR^{c31}R^{d31}$, $NR^{c31}C(O)R^{b31}$, $NR^{c31}C(O)OR^{a31}$, $NR^{c31}C(O)NR^{c31}R^{d31}$, $NR^{c31}S(O)R^{b31}$, $NR^{c31}S(O)NR^{c31}R^{d31}$, $NR^{c31}S(O)_2R^{b31}$, $NR^{c31}S(O)_2NR^{c31}R^{d31}$, $S(O)R^{b31}$, $S(O)NR^{c31}R^{d31}$, $S(O)_2R^{b31}$, and $S(O)_2NR^{c31}R^{d31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, or 4 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, or 4 independently selected $R^{3B}$ substituents;

each $R^{3B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $NHOR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}NR^{c32}R^{d32}$. $NR^{c32}C(O)R^{b32}$, $NR^{c32}C(O)OR^{a32}$, $NR^{c32}C(O)NR^{c32}R^{d32}$, $NR^{c32}S(O)R^{b32}$, $NR^{c32}S(O)NR^{c32}R^{d32}$, $NR^{c32}S(O)_2R^{b32}$, $NR^{c32}S(O)_2NR^{c32}R^{d32}$, $S(O)R^{b32}$, $S(O)NR^{c32}R^{d32}$, $S(O)_2R^{b32}$, and $S(O)_2NR^{c32}R^{d32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, or 4 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, or 4 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, or 4 independently selected $R^{3C}$ substituents;

each $R^{3C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $NHOR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}NR^{c33}R^{d33}$, $NR^{c33}C(O)R^{b33}$, $NR^{c33}C(O)$ OR$^{a33}$, NR$^{c33}$C(O)NR$^{c33}$R$^{d33}$, NR$^{c33}$S(O)R$^{b33}$, NR$^{c33}$S(O)NR$^{c33}$R$^{d33}$, NR$^{c33}$S(O)$_2$R$^{b33}$, NR$^{c33}$S(O)$_2$NR$^{c33}$R$^{d33}$, S(O)R$^{b33}$, S(O)NR$^{c33}$R$^{d33}$, S(O)$_2$R$^{b33}$, S(O)$_2$NR$^{c33}$R$^{d33}$, and OS(O)$_2$R$^{b33}$, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl- of R$^{3C}$ are each optionally substituted with 1, 2, 3, or 4 independently selected R$^M$ substituents;

each R$^{a33}$, R$^{c33}$, and R$^{d33}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a33}$, R$^{c33}$ and R$^{d33}$ are each optionally substituted with 1, 2, 3, or 4 independently selected R$^M$ substituents;

or, any R$^{c33}$ and R$^{d33}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected R$^M$ substituents;

each R$^{b33}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{b33}$ are each optionally substituted with 1, 2, 3, or 4 independently selected R$^M$ substituents;

R$^4$ is selected from H, D, halo, C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, CN, OH, and NH$_2$;

R$^5$ is selected from H, D, halo, C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, CN, OH, and NH$_2$; and each R$^M$ is independently selected from H, D, OH, halo, oxo, CN, C(O)OH, NH$_2$, NO$_2$, SF$_5$, C$_{1-6}$ alkyl, C$_{1-6}$ alkoxy, C$_{1-6}$ haloalkoxy, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-.

In some embodiments, R$^1$ is selected from C(O)R$^{b1}$, C(O)NR$^{c1}$R$^{d1}$, C(O)OR$^{a1}$, C(=NR$^{e1}$)R$^{b1}$, C(=NR$^{e1}$)NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$.

In some embodiments, R$^1$ is selected from C(O)R$^{b1}$, C(O)NR$^{c1}$R$^{d1}$, and C(O)OR$^{a1}$.

In some embodiments, R$^{a1}$, R$^{c1}$, and R$^{d1}$ are each independently selected from C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a1}$, R$^{c1}$ and R$^{d1}$ are each optionally substituted with 1, 2, 3, or 4 independently selected R$^{1A}$ substituents.

In some embodiments, R$^{a1}$, R$^{c1}$, and R$^{d1}$ are each independently selected from C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-.

In some embodiments, R$^{a1}$, R$^{c1}$, and R$^{d1}$ are each independently selected from C$_{6-10}$ aryl, C$_{3-10}$ cycloalkyl, 5-10 membered heteroaryl, and 4-10 membered heterocycloalkyl.

In some embodiments, R$^{a1}$, R$^{c1}$, and R$^{d1}$ are each independently selected from phenyl, C$_{3-6}$ cycloalkyl, 5-6 membered heteroaryl, and 4-6 membered heterocycloalkyl.

In some embodiments, R$^{b1}$ is selected from C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a1}$, R$^{c1}$ and R$^{d1}$ are each optionally substituted with 1, 2, 3, or 4 independently selected R$^{1A}$ substituents.

In some embodiments, R$^{b1}$ is selected from C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-.

In some embodiments, R$^{b1}$ is selected from C$_{6-10}$ aryl, C$_{3-10}$ cycloalkyl, 5-10 membered heteroaryl, and 4-10 membered heterocycloalkyl.

In some embodiments, R$^{b1}$ is selected from phenyl, C$_{3-6}$ cycloalkyl, 5-6 membered heteroaryl, and 4-6 membered heterocycloalkyl.

In some embodiments, R$^{b1}$ is C$_{3-6}$ cycloalkyl.

In some embodiments, R$^{b1}$ is cyclopropyl.

In some embodiments, R$^1$ is C(O)R$^{b1}$.

In some embodiments, R$^1$ is cyclopropylcarbonyl.

In some embodiments, R$^2$ is selected from H, C$_{1-6}$ alkyl, C$_{1-6}$ haloalkyl, C$_{2-6}$ alkenyl, and C$_{2-6}$ alkynyl.

In some embodiments, R$^2$ is H or C$_{1-6}$ alkyl.

In some embodiments, R$^2$ is H or methyl.

In some embodiments, R$^2$ is H.

In some embodiments, R$^2$ is methyl.

In some embodiments, R$^3$ is selected from C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^3$ are each optionally substituted with 1, 2, 3, or 4 independently selected R$^{3A}$ substituents.

In some embodiments, R$^3$ is selected from C$_{6-10}$ aryl, C$_{3-10}$ cycloalkyl, 5-10 membered heteroaryl, and 4-10 membered heterocycloalkyl-, wherein the C$_{6-10}$ aryl, C$_{3-10}$ cycloalkyl, 5-10 membered heteroaryl, and 4-10 membered heterocycloalkyl of R$^3$ are each optionally substituted with 1, 2, 3, or 4 independently selected R$^{3A}$ substituents.

In some embodiments, $R^3$ is selected from $C_{6-10}$ aryl and 5-10 membered heteroaryl, wherein the phenyl and 5-10 membered heteroaryl of $R^3$ are each optionally substituted with 1, 2, 3, or 4 independently selected $R^{3A}$ substituents.

In some embodiments, $R^3$ is selected from phenyl and 5-10 membered heteroaryl, wherein the phenyl and 5-10 membered heteroaryl of $R^3$ are each optionally substituted with 1, 2, 3, or 4 independently selected $R^{3A}$ substituents.

In some embodiments, $R^3$ is selected from phenyl and 5-10 membered heteroaryl, wherein the phenyl and 5-10 membered heteroaryl of $R^3$ are each optionally substituted with 1 or 2 independently selected $R^{3A}$ substituents.

In some embodiments, $R^3$ is selected from phenyl and indolyl, wherein the phenyl and indolyl of $R^3$ are each optionally substituted with 1, 2, 3, or 4 independently selected $R^{3A}$ substituents.

In some embodiments, $R^3$ is selected from phenyl and indolyl, wherein the phenyl and indolyl of $R^3$ are each optionally substituted with 1 or 2 independently selected $R^{3A}$ substituents.

In some embodiments, each $R^{3A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a31}$, SR$^{a31}$, C(O)R$^{b31}$, C(O)NR$^{c31}$R$^{d31}$, C(O)OR$^{a31}$, OC(O)R$^{b31}$, OC(O)NR$^{c31}$R$^{d31}$, NR$^{c31}$R$^{d31}$, NR$^{c31}$C(O)R$^{b31}$, NR$^{c31}$C(O)OR$^{a31}$, NR$^{c31}$C(O)NR$^{c31}$R$^{d31}$, S(O)R$^{b31}$, S(O)NR$^{c31}$R$^{d31}$, S(O)$_2$R$^{b31}$, and S(O)$_2$NR$^{c31}$R$^{d31}$, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents.

In some embodiments, each $R^{3A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a31}$, SR$^{a31}$, C(O)R$^{b31}$, C(O)NR$^{c31}$R$^{d31}$, C(O)OR$^{a31}$, OC(O)R$^{b31}$, OC(O)NR$^{c31}$R$^{d31}$, NR$^{c31}$R$^{d31}$, NR$^{c31}$C(O)R$^{b31}$, NR$^{c31}$C(O)OR$^{a31}$, NR$^{c31}$C(O)NR$^{c31}$R$^{d31}$, S(O)R$^{b31}$, S(O)NR$^{c31}$R$^{d31}$, S(O)$_2$R$^{b31}$, and S(O)$_2$NR$^{c31}$R$^{d31}$, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1 or 2 independently selected $R^{3B}$ substituents.

In some embodiments, each $R^{3A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, OR$^{a31}$, SR$^{a31}$, C(O)R$^{b31}$, C(O)NR$^{c31}$R$^{d31}$, C(O)OR$^{a31}$, NR$^{c31}$R$^{d31}$, S(O)R$^{b31}$, S(O)NR$^{c31}$R$^{d31}$, S(O)$_2$R$^{b31}$, and S(O)$_2$NR$^{c31}$R$^{d31}$, wherein the $C_{1-6}$ alkyl, $C_{6-10}$ aryl, $C_{3-10}$ cycloalkyl, 5-10 membered heteroaryl, and 4-10 membered heterocycloalkyl of $R^{3A}$ are each optionally substituted with 1 or 2 independently selected $R^{3B}$ substituents.

In some embodiments, each $R^{3A}$ is independently selected from halo, $C_{1-6}$ alkyl, $C_{1-6}$ haloalkyl, 5-10 membered heteroaryl, 4-10 membered heterocycloalkyl, OR$^{a31}$, SR$^{a31}$, C(O)NR$^{c31}$R$^{d31}$, NR$^{c31}$R$^{d31}$, and S(O)$_2$R$^{b31}$, wherein the $C_{1-6}$ alkyl, 5-10 membered heteroaryl, and 4-10 membered heterocycloalkyl of $R^{3A}$ are each optionally substituted with 1, 2, 3, or 4 independently selected $R^{3B}$ substituents.

In some embodiments, each $R^{3A}$ is independently selected from halo, $C_{1-6}$ alkyl, $C_{1-6}$ haloalkyl, 5-10 membered heteroaryl, 4-10 membered heterocycloalkyl, OR$^{a31}$, SR$^{a31}$, C(O)NR$^{c31}$R$^{d31}$, NR$^{c31}$R$^{d31}$, and S(O)$_2$R$^{b31}$, wherein the $C_{1-6}$ alkyl, 5-10 membered heteroaryl, and 4-10 membered heterocycloalkyl of $R^{3A}$ are each optionally substituted with 1 or 2 independently selected $R^{3B}$ substituents.

In some embodiments, each $R^{3A}$ is independently selected from halo, $C_{1-6}$ alkyl, $C_{1-6}$ haloalkyl, 5-6 membered heteroaryl, 4-6 membered heterocycloalkyl, OR$^{a31}$, SR$^{a31}$, C(O)NR$^{c31}$R$^{d31}$, NR$^{c31}$R$^{d31}$, and S(O)$_2$R$^{b31}$, wherein the $C_{1-6}$ alkyl, 5-6 membered heteroaryl, and 4-6 membered heterocycloalkyl of $R^{3A}$ are each optionally substituted with 1, 2, 3, or 4 independently selected $R^{3B}$ substituents.

In some embodiments, each $R^{3A}$ is independently selected from halo, $C_{1-6}$ alkyl, $C_{1-6}$ haloalkyl, 5-6 membered heteroaryl, 4-6 membered heterocycloalkyl, OR$^{a31}$, SR$^{a31}$, C(O)NR$^{c31}$R$^{d31}$, NR$^{c31}$R$^{d31}$, and S(O)$_2$R$^{b31}$, wherein the $C_{1-6}$ alkyl, 5-6 membered heteroaryl, and 4-6 membered heterocycloalkyl of $R^{3A}$ are each optionally substituted with 1 or 2 independently selected $R^{3B}$ substituents.

In some embodiments, $R^{a31}$, $R^{b31}$, $R^{c31}$, and $R^{d31}$ are each independently selected from H, $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{a31}$, $R^{b31}$, $R^{c31}$, and $R^{d31}$ are each optionally substituted with 1, 2, 3, or 4 independently selected $R^{3B}$ substituents.

In some embodiments, $R^{a31}$, $R^{b31}$, $R^{c31}$, and $R^{d31}$ are each independently selected from H, $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{a31}$, $R^{b31}$, $R^{c31}$, and $R^{d31}$ are each optionally substituted with 1 or 2 independently selected $R^{3B}$ substituents.

In some embodiments, $R^{a31}$, $R^{b31}$, $R^{c31}$, and $R^{d31}$ are each independently selected from H, $C_{1-6}$ alkyl, $C_{1-6}$ haloalkyl, $C_{3-6}$ cycloalkyl, and (4-6 membered heterocycloalkyl)-$C_{1-6}$ alkyl-, wherein the $C_{1-6}$ alkyl of $R^{a31}$, $R^{b31}$, $R^{c31}$, and $R^{d31}$ is optionally substituted with 1 or 2 independently selected $R^{3B}$ substituents.

In some embodiments, $R^{a31}$, $R^{b31}$, $R^{c31}$, and $R^{d31}$ are each independently selected from H, $C_{1-6}$ alkyl, $C_{1-6}$ haloalkyl, $C_{3-6}$ cycloalkyl, and (4-6 membered heterocycloalkyl)-$C_{1-6}$ alkyl-, wherein the $C_{1-6}$ alkyl of $R^{a31}$, $R^{b31}$, $R^{c31}$, and $R^{d31}$ is optionally substituted with 1 or 2 $OR^{a32}$ substituents, wherein each $OR^{a32}$ is independently selected from H, $C_{1-6}$ alkyl, $C_{1-6}$ haloalkyl, $C_{2-6}$ alkenyl, and $C_{2-6}$ alkynyl.

In some embodiments, $R^{a31}$, $R^{b31}$, $R^{c31}$, and $R^{d31}$ are each independently selected from H, $C_{1-6}$ alkyl, $C_{1-6}$ haloalkyl, $C_{3-6}$ cycloalkyl, and (4-6 membered heterocycloalkyl)-$C_{1-6}$ alkyl-, wherein the $C_{1-6}$ alkyl of $R^{a31}$, $R^{b31}$, $R^{c31}$, and $R^{d31}$ is optionally substituted with 1 or 2 OH groups.

In some embodiments, $R^{a31}$, $R^{b31}$, $R^{c31}$, and $R^{d31}$ are each independently selected from H, methyl, hydroxymethyl, difluoromethyl, cyclopropyl, and tetrahydropyranylmethyl.

In some embodiments, each $R^{3A}$ is independently selected from chloro, ethyl, trifluoromethyl, hydroxymethyl, pyrazolyl, thiazolyl, piperazinyl, methoxy, difluoromethoxy, cyclopropoxy, methylthio, methylsulfonyl, methylamino, tetrahydropyranylmethylaminocarbonyl, wherein the pyrazolyl, thiazolyl, and piperazinyl of $R^{3A}$ are each optionally substituted with 1 or 2 independently selected $R^{3B}$ substituents.

In some embodiments, each $R^{3B}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $S(O)R^{b32}$, $S(O)NR^{c32}R^{d32}$, $S(O)_2R^{b32}$, and $S(O)_2NR^{c32}R^{d32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{3B}$ are each optionally substituted with 1, 2, 3, or 4 independently selected $R^{3C}$ substituents.

In some embodiments, each $R^{3B}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $S(O)R^{b32}$, $S(O)NR^{c32}R^{d32}$, $S(O)_2R^{b32}$, and $S(O)_2NR^{c32}R^{d32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{3B}$ are each optionally substituted with 1 or 2 independently selected $R^{3C}$ substituents.

In some embodiments, each $R^{3B}$ is independently selected from $C_{1-6}$ alkyl, $C_{6-10}$ aryl, $C_{3-10}$ cycloalkyl, 4-10 membered heterocycloalkyl, and $S(O)_2R^{b32}$, wherein the $C_{1-6}$ alkyl, $C_{6-10}$ aryl, $C_{3-10}$ cycloalkyl, and 4-10 membered heterocycloalkyl of $R^{3B}$ are each optionally substituted with 1, 2, 3, or 4 independently selected $R^{3C}$ substituents.

In some embodiments, each $R^{3B}$ is independently selected from $C_{1-6}$ alkyl, $C_{6-10}$ aryl, $C_{3-10}$ cycloalkyl, 4-10 membered heterocycloalkyl, and $S(O)_2R^{b32}$, wherein the $C_{1-6}$ alkyl, $C_{6-10}$ aryl, $C_{3-10}$ cycloalkyl, and 4-10 membered heterocycloalkyl of $R^{3B}$ are each optionally substituted with 1 or 2 independently selected $R^{3C}$ substituents.

In some embodiments, each $R^{3B}$ is independently selected from $C_{1-6}$ alkyl, $C_{6-10}$ aryl, $C_{3-10}$ cycloalkyl, 4-10 membered heterocycloalkyl, and $S(O)_2R^{b32}$, wherein the $C_{1-6}$ alkyl, $C_{6-10}$ aryl, $C_{3-10}$ cycloalkyl, and 4-10 membered heterocycloalkyl of $R^{3B}$ are each optionally substituted with 1 or 2 aminocarbonyl groups; and $R^{b32}$ is selected from $C_{6-10}$ aryl and $C_{3-10}$ cycloalkyl.

In some embodiments, each $R^{3B}$ is independently selected from $C_{1-6}$ alkyl, phenyl, $C_{3-6}$ cycloalkyl, 4-6 membered heterocycloalkyl, and $S(O)_2R^{b32}$, wherein the $C_{1-6}$ alkyl of $R^{3B}$ is optionally substituted with aminocarbonyl; and $R^{b32}$ is selected from phenyl and $C_{3-6}$ cycloalkyl.

In some embodiments, each $R^{3B}$ is independently selected from methyl, aminocarbonylethyl, tetrahydropyranyl, cyclopentyl, and cyclopropylsulfonyl.

In some embodiments, $R^4$ is selected from H, D, halo, $C_{1-6}$ alkyl, $C_{1-6}$ alkoxy, $C_{2-6}$ alkenyl, $C_{2-6}$ alkynyl, and $C_{1-6}$ haloalkyl.

In some embodiments, $R^4$ is selected from H, D, $C_{1-6}$ alkyl, and $C_{1-6}$ haloalkyl.

In some embodiments, $R^4$ is selected from H, D, and $C_{1-6}$ alkyl.

In some embodiments, $R^4$ is selected from H and D.

In some embodiments, $R^4$ is H.

In some embodiments, $R^5$ is selected from H, D, halo, $C_{1-6}$ alkyl, $C_{1-6}$ alkoxy, $C_{2-6}$ alkenyl, $C_{2-6}$ alkynyl, and $C_{1-6}$ haloalkyl.

In some embodiments, $R^5$ is selected from H, D, $C_{1-6}$ alkyl, and $C_{1-6}$ haloalkyl.

In some embodiments, $R^5$ is selected from H, D, and $C_{1-6}$ alkyl.

In some embodiments, $R^5$ is H.

In some embodiments, $R^4$ and $R^5$ are each H.

In some embodiments:
$R^2$ is selected from H, $C_{1-6}$ alkyl, $C_{1-6}$ haloalkyl, $C_{2-6}$ alkenyl, and $C_{2-6}$ alkynyl;
$R^4$ is selected from H, D, halo, $C_{1-6}$ alkyl, $C_{1-6}$ alkoxy, $C_{2-6}$ alkenyl, $C_{2-6}$ alkynyl, and $C_{1-6}$ haloalkyl; and
$R^5$ is selected from H, D, halo, $C_{1-6}$ alkyl, $C_{1-6}$ alkoxy, $C_{2-6}$ alkenyl, $C_{2-6}$ alkynyl, and $C_{1-6}$ haloalkyl.

In some embodiments:
$R^2$ is H or $C_{1-6}$ alkyl;
$R^4$ is selected from H, D, and $C_{1-6}$ alkyl; and
$R^5$ is selected from H, D, and $C_{1-6}$ alkyl.

In some embodiments:
$R^2$ is H or $C_{1-6}$ alkyl;
$R^4$ is H; and
$R^5$ is H.

In some embodiments:
$R^1$ is $C(O)R^{b1}$;
$R^{b1}$ is selected from $C_{6-10}$ aryl, $C_{3-10}$ cycloalkyl, 5-10 membered heteroaryl, and 4-10 membered heterocycloalkyl;
$R^2$ is H or $C_{1-6}$ alkyl;
$R^4$ is H; and
$R^5$ is H.

In some embodiments:
$R^1$ is $C(O)R^{b1}$;
$R^{b1}$ is selected from phenyl, $C_{3-6}$ cycloalkyl, 5-6 membered heteroaryl, and 4-6 membered heterocycloalkyl;
$R^2$ is H or $C_{1-6}$ alkyl;
$R^4$ is H; and
$R^5$ is H.

In some embodiments:
$R^1$ is $C(O)R^{b1}$;
$R^{b1}$ is $C_{3-6}$ cycloalkyl;
$R^2$ is H or $C_{1-6}$ alkyl;
$R^4$ is H; and
$R^5$ is H.

In some embodiments:
$R^1$ is C(O)-cyclopropyl;
$R^2$ is H or $C_{1-6}$ alkyl;
$R^4$ is H; and
$R^5$ is H.

In some embodiments:
$R^1$ is selected from $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)R^{b1}$, $S(O)NR^{c1}R^{d1}$, $S(O)_2R^{b1}$, and $S(O)_2NR^{c1}R^{d1}$;
$R^2$ is selected from H, $C_{1-6}$ alkyl, $C_{1-6}$ haloalkyl, $C_{2-6}$ alkenyl, and $C_{2-6}$ alkynyl;
$R^3$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^3$ are each optionally substituted with 1, 2, 3, or 4 independently selected R$^{3A}$ substituents;

R$^4$ is selected from H, D, and C$_{1-6}$ alkyl; and
R$^5$ is selected from H, D, and C$_{1-6}$ alkyl.

In some embodiments:
R$^1$ is selected from C(O)R$^{b1}$, C(O)NR$^{c1}$R$^{d1}$, C(O)OR$^{a1}$, C(=NR$^{e1}$)R$^{b1}$, C(=NR$^{e1}$)NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

R$^{a1}$, R$^{c1}$, and R$^{d1}$ are each independently selected from phenyl, C$_{3-6}$ cycloalkyl, 5-6 membered heteroaryl, and 4-6 membered heterocycloalkyl;

R$^2$ is selected from H, C$_{1-6}$ alkyl, C$_{1-6}$ haloalkyl, C$_{2-6}$ alkenyl, and C$_{2-6}$ alkynyl;

R$^3$ is selected from C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^3$ are each optionally substituted with 1, 2, 3, or 4 independently selected R$^{3A}$ substituents;

each R$^{3A}$ is independently selected from halo, C$_{1-6}$ alkyl, C$_{1-6}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a31}$, SR$^{a31}$, C(O)R$^{b31}$, C(O)NR$^{c31}$R$^{d31}$, C(O)OR$^{a31}$, OC(O)R$^{b31}$, OC(O)NR$^{c31}$R$^{d31}$, NR$^{c31}$R$^{d31}$, NR$^{c31}$C(O)R$^{b31}$, NR$^{c31}$C(O)OR$^{a31}$, NR$^{c31}$C(O)NR$^{c31}$R$^{d31}$, S(O)R$^{b31}$, S(O)NR$^{c31}$R$^{d31}$, S(O)$_2$R$^{b31}$, and S(O)$_2$NR$^{c31}$R$^{d31}$, wherein the C$_{1-6}$ alkyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{3A}$ are each optionally substituted with 1, 2, 3, or 4 independently selected R$^{3B}$ substituents;

R$^{a31}$, R$^{b31}$, R$^{c31}$, and R$^{d31}$ are each independently selected from H, C$_{1-6}$ alkyl, C$_{1-6}$ haloalkyl, phenyl, C$_{3-6}$ cycloalkyl, 5-6 membered heteroaryl, 4-6 membered heterocycloalkyl, phenyl-C$_{1-6}$ alkyl-, C$_{3-6}$ cycloalkyl-C$_{1-6}$ alkyl-, (5-6 membered heteroaryl)-C$_{1-6}$ alkyl-, and (4-6 membered heterocycloalkyl)-C$_{1-6}$ alkyl-, wherein the C$_{1-6}$ alkyl, phenyl, C$_{3-6}$ cycloalkyl, 5-6 membered heteroaryl, 4-6 membered heterocycloalkyl, phenyl-C$_{1-6}$ alkyl-, C$_{3-6}$ cycloalkyl-C$_{1-6}$ alkyl-, (5-6 membered heteroaryl)-C$_{1-6}$ alkyl-, and (4-6 membered heterocycloalkyl)-C$_{1-6}$ alkyl- of R$^{a31}$, R$^{b31}$, R$^{c31}$, and R$^{d31}$ are each optionally substituted with 1, 2, 3, or 4 independently selected R$^{3B}$ substituents;

each R$^{3B}$ is independently selected from halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, S(O)R$^{b32}$, S(O)NR$^{c32}$R$^{d32}$, S(O)$_2$R$^{b32}$, and S(O)$_2$NR$^{c32}$R$^{d32}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, and 4-10 membered heterocycloalkyl of R$^{3B}$ are each optionally substituted with 1, 2, 3, or 4 independently selected R$^{3C}$ substituents;

R$^4$ is selected from H, D, and C$_{1-6}$ alkyl; and
R$^5$ is selected from H, D, and C$_{1-6}$ alkyl.

In some embodiments:
R$^1$ is C(O)R$^{b1}$;
R$^{b1}$ is selected from phenyl, C$_{3-6}$ cycloalkyl, 5-6 membered heteroaryl, and 4-6 membered heterocycloalkyl;
R$^2$ is H or C$_{1-6}$ alkyl;
wherein R$^3$ is selected from phenyl and 5-10 membered heteroaryl, wherein the phenyl and 5-10 membered heteroaryl of R$^3$ are each optionally substituted with 1, 2, 3, or 4 independently selected R$^{3A}$ substituents;

each R$^{3A}$ is independently selected from halo, C$_{1-6}$ alkyl, C$_{1-6}$ haloalkyl, C$_{6-10}$ aryl, C$_{3-10}$ cycloalkyl, 5-10 membered heteroaryl, 4-10 membered heterocycloalkyl, OR$^{a31}$, SR$^{a31}$, C(O)R$^{b31}$, C(O)NR$^{c31}$R$^{d31}$, C(O)OR$^{a31}$, NR$^{c31}$R$^{d31}$, S(O)R$^{b31}$, S(O)NR$^{c31}$R$^{d31}$, S(O)$_2$R$^{b31}$, and S(O)$_2$NR$^{c31}$R$^{d31}$, wherein the C$_{1-6}$ alkyl, C$_{6-10}$ aryl, C$_{3-10}$ cycloalkyl, 5-10 membered heteroaryl, and 4-10 membered heterocycloalkyl of R$^{3A}$ are each optionally substituted with 1, 2, 3, or 4 independently selected R$^{3B}$ substituents;

each R$^{a31}$, R$^{b31}$, R$^{c31}$ and R$^{d31}$ is independently selected from H, C$_{1-6}$ alkyl, C$_{1-6}$ haloalkyl, C$_{3-6}$ cycloalkyl, and (4-6 membered heterocycloalkyl)-C$_{1-6}$ alkyl-, wherein the C$_{1-6}$ alkyl of R$^{a31}$, R$^{b31}$, R$^{c31}$, and R$^{d31}$ is optionally substituted with 1 or 2 OH groups;

each R$^{3B}$ is independently selected from C$_{1-6}$ alkyl, C$_{6-10}$ aryl, C$_{3-10}$ cycloalkyl, 4-10 membered heterocycloalkyl, and S(O)$_2$R$^{b32}$, wherein the C$_{1-6}$ alkyl, C$_{6-10}$ aryl, C$_{3-10}$ cycloalkyl, and 4-10 membered heterocycloalkyl of R$^{3B}$ are each optionally substituted with 1, 2, 3, or 4 independently selected R$^{3C}$ substituents;

R$^4$ is selected from H, D, and C$_{1-6}$ alkyl; and
R$^5$ is selected from H, D, and C$_{1-6}$ alkyl.

In some embodiments:
R$^1$ is cyclopropylcarbonyl;
R$^2$ is H or methyl;
R$^3$ is selected from phenyl and indolyl, wherein the phenyl and indolyl of R$^3$ are each optionally substituted with 1, 2, 3, or 4 independently selected R$^{3A}$ substituents;

each R$^{3A}$ is independently selected from chloro, ethyl, trifluoromethyl, hydroxymethyl, pyrazolyl, thiazolyl, piperazinyl, methoxy, difluoromethoxy, cyclopropoxy, methylthio, methylsulfonyl, methylamino, tetrahydropyranylmethylaminocarbonyl, wherein the pyrazolyl, thiazolyl, and piperazinyl of R$^{3A}$ are each optionally substituted with 1 or 2 independently selected R$^{3B}$ substituents;

each R$^{3B}$ is independently selected from C$_{1-6}$ alkyl, phenyl, C$_{3-6}$ cycloalkyl, 4-6 membered heterocycloalkyl, and S(O)$_2$R$^{b32}$, wherein the C$_{1-6}$ alkyl of R$^{3B}$ is optionally substituted with aminocarbonyl; and R$^{b32}$ is selected from phenyl and C$_{3-6}$ cycloalkyl;

R$^4$ is H; and
R$^5$ is H.

In some embodiments, the compound of Formula I is a compound of Formula II:

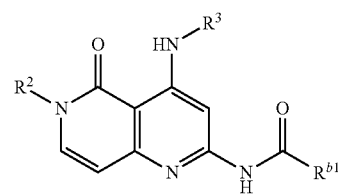

II or a pharmaceutically acceptable salt thereof, wherein variables R$^{b1}$, R$^2$, and R$^3$ are defined according to the definitions provided herein for compounds of Formula I.

The compound of claim 1, wherein the compound of Formula I is a compound of Formula III:

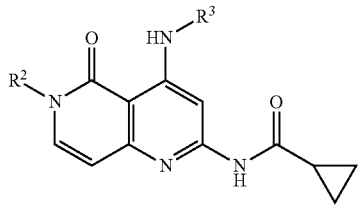

III or a pharmaceutically acceptable salt thereof, wherein variables $R^2$ and $R^3$ are defined according to the definitions provided herein for compounds of Formula I.

In some embodiments, the compound of Formula I is a compound of Formula IV:

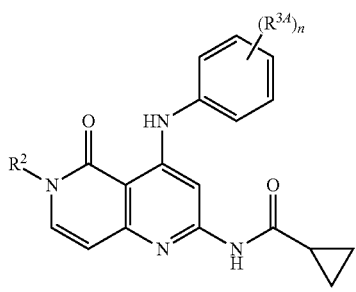

IV or a pharmaceutically acceptable salt thereof, wherein n is 0, 1, 2, 3 or 4, and variables $R^2$ and $R^{3A}$ are defined according to the definitions provided herein for compounds of Formula I.

In some embodiments, the compound provided herein is selected from:

N-(4-((2-methoxy-3-(1H-pyrazol-4-yl)phenyl)amino)-5-oxo-5,6-dihydro-1,6-naphthyridin-2-yl)cyclopropanecarboxamide;

N-(4-((2-methoxy-3-(2-(tetrahydro-2H-pyran-4-yl)thiazol-5-yl)phenyl)amino)-5-oxo-5,6-dihydro-1,6-naphthyridin-2-yl)cyclopropanecarboxamide;

N-(4-((3-(1-cyclopentyl-1H-pyrazol-4-yl)-2-methoxyphenyl)amino)-5-oxo-5,6-dihydro-1,6-naphthyridin-2-yl)cyclopropanecarboxamide;

N-(4-((3-(4-(cyclopropylsulfonyl)piperazin-1-yl)-2-methoxyphenyl)amino)-5-oxo-5,6-dihydro-1,6-naphthyridin-2-yl)cyclopropanecarboxamide;

N-(4-((2-methoxy-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide;

N-(5-oxo-4-((3-(1-(tetrahydro-2H-pyran-4-yl)-1H-pyrazol-4-yl)phenyl)amino)-5,6-dihydro-1,6-naphthyridin-2-yl)cyclopropanecarboxamide;

N-(4-((2-methoxy-4-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide;

N-(4-((3-(1-(1-amino-1-oxopropan-2-yl)-1H-pyrazol-4-yl)-2-methoxyphenyl)amino)-5-oxo-5,6-dihydro-1,6-naphthyridin-2-yl)cyclopropanecarboxamide;

N-(4-((1-ethyl-1H-indol-7-yl)amino)-5-oxo-5,6-dihydro-1,6-naphthyridin-2-yl)cyclopropanecarboxamide;

N-(4-((2-methoxy-3-(2-(tetrahydro-2H-pyran-4-yl)thiazol-5-yl)phenyl)amino)-6-methyl-5-oxo-5,6-dihydro-1,6-naphthyridin-2-yl)cyclopropanecarboxamide;

3-((2-(cyclopropanecarboxamido)-5-oxo-5,6-dihydro-1,6-naphthyridin-4-yl)amino)-2-methoxy-N-((tetrahydro-2H-pyran-4-yl)methyl)benzamide;

N-(4-((2-(methylthio)-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide;

N-(4-((2-(methylsulfonyl)-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide;

N-(4-((2-methoxy-3-(trifluoromethyl)phenyl)amino)-5-oxo-5,6-dihydro-1,6-naphthyridin-2-yl)cyclopropanecarboxamide;

N-(4-((2,3-dimethoxyphenyl)amino)-5-oxo-5,6-dihydro-1,6-naphthyridin-2-yl)cyclopropanecarboxamide;

N-(4-((3-chloro-2-(1H-pyrazol-4-yl)phenyl)amino)-5-oxo-5,6-dihydro-1,6-naphthyridin-2-yl)cyclopropanecarboxamide;

N-(4-((3-chloro-2-(5-methyl-1H-pyrazol-4-yl)phenyl)amino)-5-oxo-5,6-dihydro-1,6-naphthyridin-2-yl)cyclopropanecarboxamide;

N-(4-((2-(1H-pyrazol-4-yl)-3-(trifluoromethyl)phenyl)amino)-5-oxo-5,6-dihydro-1,6-naphthyridin-2-yl)cyclopropanecarboxamide;

N-(4-((2-(5-methyl-1H-pyrazol-4-yl)-3-(trifluoromethyl)phenyl)amino)-5-oxo-5,6-dihydro-1,6-naphthyridin-2-yl)cyclopropanecarboxamide;

N-(4-((2-(difluoromethoxy)phenyl)amino)-5-oxo-5,6-dihydro-1,6-naphthyridin-2-yl)cyclopropanecarboxamide;

N-(4-((2-methoxyphenyl)amino)-5-oxo-5,6-dihydro-1,6-naphthyridin-2-yl)cyclopropanecarboxamide;

N-(4-((2-(methylamino)phenyl)amino)-5-oxo-5,6-dihydro-1,6-naphthyridin-2-yl)cyclopropanecarboxamide;

N-(4-((2-(hydroxymethyl)phenyl)amino)-5-oxo-5,6-dihydro-1,6-naphthyridin-2-yl)cyclopropanecarboxamide; and N-(4-((2-cyclopropoxyphenyl)amino)-5-oxo-5,6-dihydro-1,6-naphthyridin-2-yl)cyclopropanecarboxamide;

or a pharmaceutically acceptable salt thereof.

In some embodiments, the pharmaceutically acceptable salt is a trifluoroacetic acid salt.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, .sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and iso-propoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 5 to 10 carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$ haloalkoxy" refers to a group of formula —O-haloalkyl having n to m carbon atoms. Example haloalkoxy groups include OCF$_3$ and OCHF$_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include CF$_3$, C$_2$F$_5$, CHF$_2$, CH$_2$F, CCl$_3$, CHCl$_2$, C$_2$Cl$_5$ and the like.

As used herein, the term "thio" refers to a group of formula-SH.

As used herein, the term "carbamyl" to a group of formula —C(O)NH$_2$.

As used herein, the term "carbonyl", employed alone or in combination with other terms, refers to a —C(O)— group.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylamino sulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH (alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "cyano-$C_{1-n}$ alkyl" refers to a group of formula —($C_{1-n}$ alkylene)-CN, wherein the alkyl group has 1 to n carbon atoms. In some embodiments, the alkyl group has 1 to 6, 1 to 4, or 1 to 3 carbon atoms, e.g., —($C_{1-3}$ alkylene)-CN.

As used herein, the term "HO—$C_{1-n}$ alkyl" refers to a group of formula —($C_{1-n}$ alkylene)-OH, wherein the alkyl group has 1 to n carbon atoms. In some embodiments, the alkyl group has 1 to 6, 1 to 4, or 1 to 3 carbon atoms, e.g., —($C_{1-3}$ alkylene)-OH.

As used herein, the term "$C_{1-n}$alkoxy-$C_{1-n}$alkyl" refers to a group of formula —($C_{1-n}$alkylene)-O($C_{1-n}$ alkyl), wherein the alkyl group has 1 to n carbon atoms. In some embodiments, the alkyl group has 1 to 6, 1 to 4, or 1 to 3 carbon atoms, e.g., —($C_{1-6}$ alkylene)-O($C_{1-6}$ alkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkylcarbonyloxy" is a group of formula —OC(O)— alkyl, wherein the alkyl group has n to m carbon atoms.

As used herein, "aminocarbonyloxy" is a group of formula —OC(O)—NH$_2$.

As used herein, "$C_{n-m}$ alkylaminocarbonyloxy" is a group of formula —OC(O)—NH-alkyl, wherein the alkyl group has n to m carbon atoms.

As used herein, "di($C_{n-m}$alkyl)aminocarbonyloxy" is a group of formula —OC(O)—N(alkyl)$_2$, wherein each alkyl group has, independently, n to m carbon atoms.

As used herein "$C_{n-m}$ alkoxycarbonylamino" refers to a group of formula —NHC(O)O($C_{n-m}$ alkyl), wherein the alkyl group has n to m carbon atoms.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1] heptanyl, bicyclo[2.2.2]octanyl, spiro[3.3]heptanyl, and the like. In some embodiments, cycloalkyl cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S, and B. In some embodiments, the heteroaryl is a 5-6 monocyclic heteroaryl having 1 or 2 heteroatom ring members independently selected from N, O, and S. In some embodiments, the heteroaryl group contains 3 to 10, 4 to 10, 5 to 10, 5 to 7, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, thienyl (or thiophenyl), furyl (or furanyl), pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine, pyridinyl, pyrimidinyl, pyrazinyl, pyridazinyl, azolyl, triazolyl, thiadiazolyl, quinolinyl, isoquinolinyl, indolyl, benzothiophenyl, benzofuranyl, benzisoxazolyl, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, triazolo[4,3-a] pyridinyl, 1H-pyrrolo[3,2-b]pyridinyl, 1H-pyrrolo[2,3-b] pyridinyl, pyrazolo[1,5-a]pyridinyl, indazolyl, and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S, and B, and wherein the ring-forming carbon atoms and heteroatoms of a heterocycloalkyl group can be optionally substituted by one or more oxo or sulfido (e.g., C(O), S(O), C(S), or $S(O)_2$, etc.). When a ring-forming carbon atom or heteroatom of a heterocycloalkyl group is optionally substituted by one or more oxo or sulfide, the O or S of said group is in addition to the number of ring-forming atoms specified herein (e.g., a 1-methyl-6-oxo-1,6-dihydropyridazin-3-yl is a 6-membered heterocycloalkyl group, wherein a ring-forming carbon atom is substituted with an oxo group, and wherein the 6-membered heterocycloalkyl group is further substituted with a methyl group). Heterocycloalkyl groups include monocyclic and polycyclic (e.g., having 2 fused rings) systems. Included in heterocycloalkyl are monocyclic and polycyclic 3 to 10, 4 to 10, 5 to 10, 4 to 7, 5 to 7, or 5 to 6 membered heterocycloalkyl groups. Heterocycloalkyl groups can also include spirocycles and bridged rings (e.g., a 5 to 10 membered bridged biheterocycloalkyl ring having one or more of the ring-forming carbon atoms replaced by a heteroatom independently selected from N, O, S, and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatom or 1 heteroatom. In some embodiments, the heterocycloalkyl is a monocyclic 4-6 membered heterocycloalkyl having 1 or 2 heteroatoms independently selected from N, O, S and B and having one or more oxidized ring members. In some embodiments, the heterocycloalkyl is a monocyclic or bicyclic 5-10 membered heterocycloalkyl having 1, 2, 3, or 4 heteroatoms independently selected from N, O, S, and B and having one or more oxidized ring members. In some embodiments, the heterocycloalkyl is a monocyclic or bicyclic 5 to 10 membered heterocycloalkyl having 1, 2, 3, or 4 heteroatoms independently selected from N, O, and S and having one or more oxidized ring members. In some embodiments, the heterocycloalkyl is a monocyclic 5 to 6 membered heterocycloalkyl having 1, 2, 3, or 4 heteroatoms independently selected from N, O, and S and having one or more oxidized ring members.

Example heterocycloalkyl groups include pyrrolidin-2-one (or 2-oxopyrrolidinyl), 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, 1,2,3,4-tetrahydroisoquinoline, benzazapene, azabicyclo[3.1.0]hexanyl, diazabicyclo[3.1.0]hexanyl, oxobicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxobicyclo[2.2.2]octanyl, azabicyclo[2.2.2]octanyl, azaadamantanyl, diazaadamantanyl, oxoadamantanyl, azaspiro[3.3]heptanyl, diazaspiro[3.3]heptanyl, oxo-azaspiro[3.3]heptanyl, azaspiro[3.4]octanyl, diazaspiro[3.4]octanyl, oxo-azaspiro[3.4]octanyl, azaspiro[2.5]octanyl, diazaspiro[2.5]octanyl, azaspiro[4.4]nonanyl, diazaspiro[4.4]nonanyl, oxo-azaspiro[4.4]nonanyl, azaspiro[4.5]decanyl, diazaspiro[4.5]decanyl, diazaspiro[4.4]nonanyl, oxo-diazaspiro[4.4]nonanyl, oxo-dihydropyridazinyl, oxo-2,6-diazaspiro[3.4]octanyl, oxohexahydropyrrolo[1,2-a]pyrazinyl, 3-oxopiperazinyl, oxo-pyrrolidinyl, oxo-pyridinyl and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, an "alkyl linking group" is a bivalent straight chain or branched alkyl linking group ("alkylene group"). For example, "$C_{o-p}$ cycloalkyl-$C_{n-m}$alkyl-", "$C_{o-p}$ aryl-$C_{n-m}$alkyl-", "phenyl-$C_{n-m}$ alkyl-", "heteroaryl-$C_{n-m}$alkyl-", and "heterocycloalkyl-$C_{n-m}$alkyl-" contain alkyl linking groups. Examples of "alkyl linking groups" or "alkylene groups" include methylene, ethan-1,1-diyl, ethan-1,2-diyl, propan-1,3-dilyl, propan-1,2-diyl, propan-1,1-diyl and the like.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl, or sulfonyl group.

As used herein, the term "independently selected from" means that each occurrence of a variable or substituent (e.g., each $R^M$), are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula I, Formula II, etc.) provided herein include stereoisomers of the compounds.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis will be appreciated by those skilled in the art, the compounds provided herein, including salts and stereoisomers thereof, can be prepared using known organic synthesis techniques and can be synthesized according to any of numerous possible synthetic routes.

Compounds of Formula I, and salts thereof, can be prepared as shown in Scheme 1. Requisite 1,6-naphthyridin-5(6H)-one intermediates 1-3 can be prepared by treating a suitably substituted (e.g., 2-alkyl substituted) nicotinic ester 1-1 (wherein R is a suitable group, e.g., $CH_3$ or $CH_2CH_3$) with base (e.g., sodium hydride) and a suitable nitrile 1-2a or nitrile equivalent 1-2b (e.g., 1,3,5-triazine) at elevated temperature (e.g., at 100° C.). Amine 1-4 can be added to intermediate 1-3 (wherein $Y^3$ is a suitable leaving group such as halogen (e.g., Cl)) via nucleophilic aromatic substitution in the presence of a base (e.g., LiHMDS) in a suitable solvent (e.g., THF) at low temperature (e.g., 0° C.) to afford intermediate 1-5. Where not commercially available, desired amines 1-4 can be prepared using methods known to one skilled in the art (e.g., via Suzuki coupling, Buchwald coupling, hydrogenation, reduction, alkylation, $S_NAr$ substitution, and the like). Palladium catalyzed cross-coupling between intermediate 1-5 (wherein $Y^1$ is a suitable halogen (e.g., Cl, Br, I) or pseudohalogen (e.g., OMs or OTf)) and compound 1-6 can be effected under standard Buchwald-Hartwig amination conditions (e.g., in the presence of a palladium catalyst (e.g., tris(dibenzylideneacetone)dipalladium(0)), a suitable ligand (e.g., 9,9-dimethyl-4,5-bis(diphenylphosphino)xanthene), and a suitable base (e.g., $Cs_2CO_3$ or NaOtBu) in a suitable solvent (e.g., dioxane) at elevated temperature (e.g., 100° C.)) to afford compounds 1-7. Where desired, further elaboration can take place via alkylation of 1-7 with R²-LG (wherein LG is a suitable leaving group (e.g., Cl, Br, I, OTs, OMs) in the presence of base (e.g., K₂CO₃) in a suitable solvent (e.g., DMF)) to afford compounds of Formula I, or salts thereof.

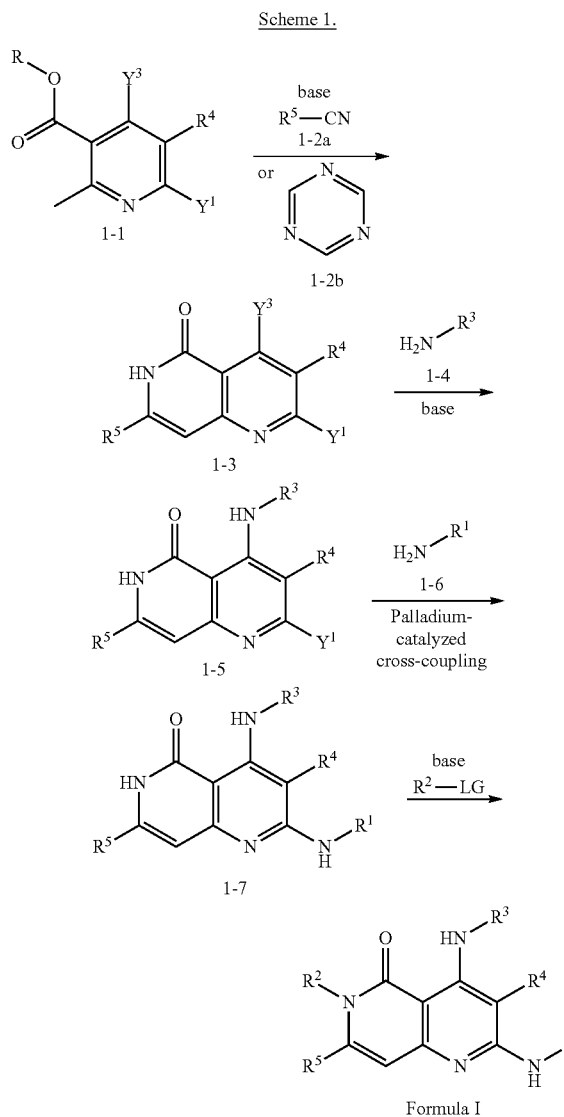

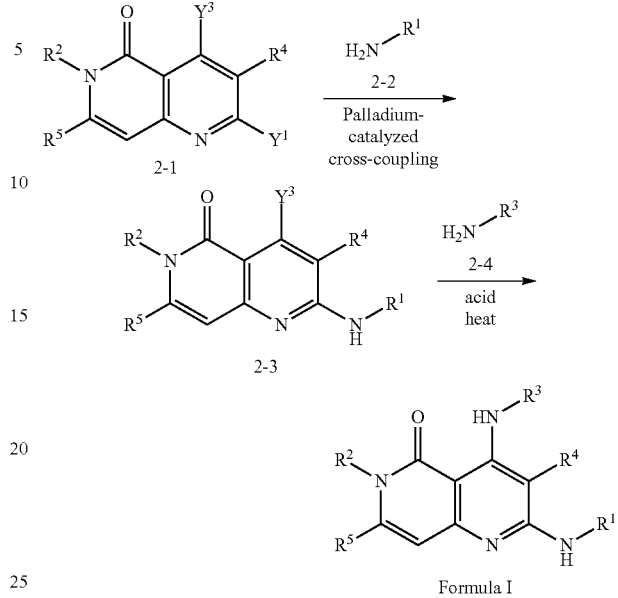

Alternatively, compounds of Formula I, or salts thereof, can be prepared as shown in Scheme 2. Palladium catalyzed cross-coupling between intermediate 2-1 (wherein $Y^1$ is a suitable halogen (e.g., Cl, Br, I) or pseudohalogen (e.g., OMs or OTf)) and compound 2-2 can be effected under standard Buchwald-Hartwig amination conditions (e.g., in the presence of a palladium catalyst (e.g., tris(dibenzylideneacetone)dipalladium(0)), a suitable ligand (e.g., 9,9-dimethyl-4,5-bis(diphenylphosphino)xanthene), and a suitable base (e.g., Cs₂CO₃ or NaOtBu) in a suitable solvent (e.g., dioxane) at elevated temperature (e.g., 100° C.)) to afford intermediate 2-3. Amine 2-4 can be added to intermediate 2-3 (wherein $Y^3$ is a suitable leaving group such as halogen (e.g., Cl)) via nucleophilic aromatic substitution in the presence of acid (e.g., HCl) in a suitable solvent (e.g., 2-methoxy ethanol) at elevated temperature (e.g., 140° C.) to afford compounds of Formula I, or salts thereof.

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds described herein can inhibit the activity of the V617F variant of the protein-tyrosine kinase JAK2 (i.e., "V617F" or "JAK2V617F"). Compounds which inhibit V617F are useful in providing a means of preventing the growth or inducing apoptosis in tumors, particularly by inhibiting angiogenesis. It is therefore anticipated that the compounds of the disclosure are useful in treating or preventing proliferative disorders such as cancers. In particular tumors with activating mutants of receptor tyrosine kinases or upregulation of receptor tyrosine kinases may be particularly sensitive to the inhibitors.

In certain embodiments, the disclosure provides a method for treating a V617F-related disorder in a patient in need thereof, comprising the step of administering to said patient a compound of the disclosure, or a pharmaceutically acceptable composition thereof.

Myeloproliferative diseases (MPD) are multipotent hematopoietic stem cell disorders characterized by excess production of various blood cells. MPNs include polycythemia vera (PV), essential thrombocythemia (ET), and idiopathic myelofibrosis (IMF). JAK2 V617F mutation is reported in about 95% of patients with PV, in 35% to 70% of patients with ET, and 50% of patients with IMF. Also, JAK2 exon 12 mutations are detected in some of the V617F-negative PV patients (Ma et al., J. Mol. Diagn., 11: 49-53, 2009). In some embodiments, the compounds of the disclosure can be useful in the treatment of myeloproliferative disorders (e.g., myeloproliferative neoplasms) in a patient in need thereof, such as polycythemia vera, essential thrombocythemia, myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like.

In some embodiments, the myeloproliferative disorder is a myeloproliferative neoplasm.

In some embodiments, the myeloproliferative disorder is myelofibrosis (e.g., primary myelofibrosis (PMF) or post polycythemia vera/essential thrombocythemia myelofibrosis (Post-PV/ET MF)).

In some embodiments, the myeloproliferative disorder is primary myelofibrosis (PMF).

In some embodiments, the myeloproliferative disorder is post-essential thrombocythemia myelofibrosis (Post-ET MF).

In some embodiments, the myeloproliferative disorder is post polycythemia vera myelofibrosis (Post-PV MF).

In some embodiments, the myeloproliferative disorder is selected from primary myelofibrosis (PMF), polycythemia vera (PV), and essential thrombocythemia (ET).

In some embodiments, the myeloproliferative neoplasm is primary myelofibrosis (PMF).

In some embodiments, the myeloproliferative neoplasm is polycythemia vera (PV).

In some embodiments, the myeloproliferative neoplasm is essential thrombocythemia (ET).

Myeloproliferative diseases include disorders of a bone marrow or lymph node-derived cell type, such as a white blood cell. A myeloproliferative disease can manifest by abnormal cell division resulting in an abnormal level of a particular hematological cell population. The abnormal cell division underlying a proliferative hematological disorder is typically inherent in the cells and not a normal physiological response to infection or inflammation. Leukemia is a type of myeloproliferative disease. Exemplary myeloproliferative diseases include, but are not limited to, acute myeloid leukemia (AML), acute lymphoblastic leukemia (ALL), chronic lymphocytic leukemia (CLL), myelodysplastic syndrome (MDS), chronic myeloid leukemia (CML), hairy cell leukemia, leukemic manifestations of lymphomas, multiple myeloma, polycythemia vera (PV), essential thrombocythemia (ET), idiopathic myelofibrosis (IMF), hypereosinophilic syndrome (HES), chronic neutrophilic leukemia (CNL), myelofibrosis with myeloid metaplasia (MMM), chronic myelomonocytic leukemia (CMML), juvenile myelomonocytic leukemia, chronic basophilic leukemia, chronic eosinophilic leukemia, systemic mastocytosis (SM), and unclassified myeloproliferative diseases (UMPD or MPD-NC). Lymphoma is a type of proliferative disease that mainly involves lymphoid organs, such as lymph nodes, liver, and spleen. Exemplary proliferative lymphoid disorders include lymphocytic lymphoma (also called chronic lymphocytic leukemia), follicular lymphoma, large cell lymphoma, Burkitt's lymphoma, marginal zone lymphoma, lymphoblastic lymphoma (also called acute lymphoblastic lymphoma).

For example, the compounds of the disclosure are useful in the treatment of cancer. Example cancers include bladder cancer (e.g., urothelial carcinoma, squamous cell carcinoma, adenocarcinoma), breast cancer (e.g., hormone R positive, triple negative), cervical cancer, colorectal cancer, cancer of the small intestine, colon cancer, rectal cancer, cancer of the anus, endometrial cancer, gastric cancer (e.g., gastrointestinal stromal tumors), head and neck cancer (e.g., cancers of the larynx, hypopharynx, nasopharynx, oropharynx, lips, and mouth, squamous head and neck cancers), kidney cancer (e.g., renal cell carcinoma, urothelial carcinoma, sarcoma, Wilms tumor), liver cancer (e.g., hepatocellular carcinoma, cholangiocellular carcinoma (e.g., intrahepatic, hilar or perihilar, distal extrahepatic), liver angiosarcoma, hepatoblastoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, vulvar cancer, esophageal cancer, gall bladder cancer, pancreatic cancer (e.g. exocrine pancreatic carcinoma), stomach cancer, thyroid cancer, parathyroid cancer, neuroendocrine cancer (e.g., pheochromocytoma, Merkel cell cancer, neuroendocrine carcinoma), skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, acute myeloid leukemia (AML), B-cell lymphoma, cutaneous T-cell lymphoma, acute myelogenous leukemia, Hodgkin's or non-Hodgkin's lymphoma, myeloproliferative neoplasms (e.g., 8p11 myeloproliferative syndrome, polycythemia vera (PV), essential thrombocythemia (ET), and primary myelofibrosis (PMF)), myelodysplastic syndrome, chronic eosinophilic leukemia, Waldenstrom's Macroglubulinemia, hairy cell lymphoma, chronic myelogenic lymphoma, acute lymphoblastic lymphoma, AIDS-related lymphomas, and Burkitt's lymphoma.

In certain embodiments, provided herein is a method of treating cancer comprising administering to a patient in need thereof a therapeutically effect amount of a compound of the disclosure. In certain embodiments, the cancer is selected from T lymphoblastic lymphoma, glioblastoma, melanoma, rhabdosarcoma, lymphosarcoma, and osteosarcoma.

Other cancers treatable with the compounds of the disclosure include tumors of the eye, glioblastoma, melanoma, leiomyosarcoma, and urothelial carcinoma (e.g., ureter, urethra, bladder, urachus).

The compounds of the disclosure can also be useful in the inhibition of tumor metastases.

In some embodiments, the compounds of the disclosure as described herein can be used to treat Alzheimer's disease, HIV, or tuberculosis.

In some embodiments, the compounds of the disclosure can be useful in the treatment of myelodysplastic syndrome (MDS) in a patient in need thereof. In some embodiments, said patient having the myelodysplastic syndrome (MDS) is red blood cell transfusion dependent.

As used herein, myelodysplastic syndromes are intended to encompass heterogeneous and clonal hematopoietic disorders that are characterized by ineffective hematopoiesis on one or more of the major myeloid cell lineages. Myelodysplastic syndromes are associated with bone marrow failure, peripheral blood cytopenias, and a propensity to progress to acute myeloid leukemia (AML). Moreover, clonal cytogenetic abnormalities can be detected in about 50% of cases with MDS. In 1997, The World Health Organization (WHO) in conjunction with the Society for Hematopathology (SH) and the European Association of Hematopathology (EAHP) proposed new classifications for hematopoietic neoplasms (Harris, et al., *J Clin Oncol* 1999; 17:3835-3849; Vardiman, et al., *Blood* 2002; 100:2292-2302). For MDS, the WHO utilized not only the morphologic criteria from the French-American-British (FAB) classification but also incorporated available genetic, biologic, and clinical characteristics to define subsets of MDS (Bennett, et al., *Br. J. Haematol.* 1982; 51:189-199). In 2008, the WHO classification of MDS (Table 1) was further refined to allow precise and prognostically relevant subclassification of unilineage dysplasia by incorporating new clinical and scientific information (Vardiman, et al., *Blood* 2009; 114:937-951; Swerdlow, et al., *WHO Classification of Tumours of Haematopoietic and Lymphoid Tissues.* 4th Edition. Lyon France: IARC Press; 2008:88-103; Bunning and Germing, "Myelodysplastic syndromes/neoplasms" in Chapter 5, Swerdlow, et al, eds. *WHO Classification of Tumours of Haematopoietic and Lymphoid Tissues*, (ed. 4th edition): Lyon, France: IARC Press; 2008: 88-103).

TABLE 1

| 2008 WHO Classification for De Novo Myelodysplastic Syndrome | | |
|---|---|---|
| Subtype | Blood | Bone Marrow |
| Refractory cytopenia with unilineage dysplasia (RCUD) | Single or Bicytopenia | Dysplasia in ≥10% of 1 cell line, <5% blasts |
| Refractory anemia with ring sideroblasts (RARS) | Anemia, no blasts | ≥15% of erythroid precursors w/ring sideroblasts, erythroid dysplasia only, <5% blasts |
| Refractory cytopenia with multilineage dysplasia | Cytopenia(s), <1 × 10⁹/L monocytes | Dysplasia in ≥10% of cells in ≥2 hematopoietic lineages, ±15% ring sideroblasts, <5% blasts |
| Refractory anemia with excess blasts-1 (RAEB-1) | Cytopenia(s), ≤2% to 4% blasts, <1 × 10⁹/L monocytes | Unilineage or multilineage dysplasia, No Auer rods, 5% to 9% blasts |
| Refractory anemia with excess blasts-2 (RAEB-2) | Cytopenia(s), ≤5% to 19% blasts, <1 × 10⁹/L monocytes | Unilineage or multilineage dysplasia, ± Auer rods, 10% to 19% blasts |
| Myelodysplastic syndrome, unclassified (MDS-U) | Cytopenias | Unilineage or no dysplasia but characteristic MDS cytogenetics, <5% blasts |
| MDS associated with isolated del(5q) | Anemia, platelets normal or increased | Unilineage erythroid. Isolated del(5q), <5% blasts |

In some embodiments, the myelodysplastic syndrome is refractory cytopenia with unilineage dysplasia (RCUD).

In some embodiments, the myelodysplastic syndrome is refractory anemia with ring sideroblasts (RARS).

In some embodiments, the myelodysplastic syndrome is refractory anemia with ring sideroblasts associated with thrombocytosis (RARS-T).

In some embodiments, the myelodysplastic syndrome is refractory cytopenia with multilineage dysplasia.

In some embodiments, the myelodysplastic syndrome is refractory anemia with excess blasts-1 (RAEB-1).

In some embodiments, the myelodysplastic syndrome is refractory anemia with excess blasts-2 (RAEB-2).

In some embodiments, the myelodysplastic syndrome is myelodysplastic syndrome, unclassified (MDS-U).

In some embodiments, the myelodysplastic syndrome is myelodysplastic syndrome associated with isolated del(5q).

In some embodiments, the myelodysplastic syndrome is refractory to erythropoiesis-stimulating agents.

In some embodiments, the compounds of the disclosure can be useful in the treatment of myeloproliferative disorder/myelodysplastic overlap syndrome (MPD/MDS overlap syndrome).

In some embodiments, the compounds of the disclosure can be useful in the treatment of leukemia.

In some embodiments, the compounds of the disclosure can be useful in the treatment of acute myeloid leukemia (AML).

In addition to oncogenic neoplasms, the compounds of the disclosure can be useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes.

The compounds provided herein may further be useful in the treatment of fibrotic diseases, such as where a disease symptom or disorder is characterized by fibrosis. Example fibrotic diseases include liver cirrhosis, glomerulonephritis, pulmonary fibrosis, systemic fibrosis, rheumatoid arthritis, and wound healing.

In some embodiments, the compounds provided herein can be used in the treatment of a hypophosphatemia disorder such as, for example, X-linked hypophosphatemic rickets, autosomal recessive hypophosphatemic rickets, and autosomal dominant hypophosphatemic rickets, or tumor-induced osteromalacia.

In some embodiments, provided herein is a method of increasing survival or progression-free survival in a patient, comprising administering a compound provided herein to the patient. In some embodiments, the patient has cancer. In some embodiments, the patient has a disease or disorder described herein. As used herein, progression-free survival refers to the length of time during and after the treatment of a solid tumor that a patient lives with the disease but it does not get worse. Progression-free survival can refer to the length of time from first administering the compound until the earlier of death or progression of the disease. Progression of the disease can be defined by RECIST v. 1.1 (Response Evaluation Criteria in Solid Tumors), as assessed by an independent centralized radiological review committee. In some embodiments, administering of the compound results in a progression free survival that is greater than about 1 month, about 2 months, about 3 months, about 4 months, about 5 months, about 6 months, about 8 months, about 9 months, about 12 months, about 16 months, or about 24 months. In some embodiments, the administering of the compound results in a progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months. In some embodiments, the administering of the compound results in an increase of progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months.

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a V617F variant with a compound described herein includes the administration of a compound described herein to an individual or patient, such as a human, having a V617F variant, as well as, for example, introducing a compound described herein into a sample containing a cellular or purified preparation containing the V617F variant.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington; The Science and Practice of Pharmacy,* 21st ed; Lippincott Williams & Wilkins: Philadelphia, Pa., 2005; *Handbook of Pharmaceutical Excipients, 6th ed.*; Rowe et al., Eds.; The Pharmaceutical Press and the American Pharmaceutical Association: 2009; *Handbook of Pharmaceutical Additives, 3rd ed.*; Ash and Ash Eds.; Gower Publishing Company: 2007; *Pharmaceutical Preformulation and Formulation, 2nd ed.*; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

It is appreciated that certain features of the disclosure, which are, for clarity, described in the context of separate embodiments, can also be provided in combination in a single embodiment (while the embodiments are intended to be combined as if written in multiply dependent form). Conversely, various features of the disclosure which are, for brevity, described in the context of a single embodiment, can also be provided separately or in any suitable subcombination.

Combination Therapies

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc), and/or tyrosine kinase inhibitors can be used in combination with compounds described herein for treatment or prevention of V617F-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the solid forms of the inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD19, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, compounds described herein can be used in combination with targeted therapies, including JAK kinase inhibitors (ruxolitinib, additional JAK 1/2 and JAK 1-selective, baricitinib or itacitinib), Pim kinase inhibitors (e.g., LGH447, INCB053914 and SGI-1776), PI3 kinase inhibitors including PI3K-delta selective and broad spectrum PI3K inhibitors (e.g., INCB50465 and INCB50797), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfdzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibitors (e.g., olaparib or rucaparib), and inhibitors of BTK such as ibrutinib.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of: abarelix, abiraterone, afatinib, aflibercept, aldesleukin, alemtuzumab, alitretinoin, allopurinol, altretamine, amidox, amsacrine, anastrozole, aphidicolin, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxaflne, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafarnib, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifarnib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

In some embodiments, compounds described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 μM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012, nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is MGA012. In some embodiments, the anti-PD1 antibody is SHR-1210. Other anti-cancer agent (s) include antibody therapeutics such as 4-1BB (e.g. urelumab, utomilumab.

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO 1, TDO, or arginase. Examples of IDO 1 inhibitors include epacadostat, NLG919, BMS-986205, PF-06840003, IOM2983, RG-70099 and LY338196.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfdzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with inhibitors described herein. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with compounds described herein. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide, ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (e.g., *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel, mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin (see e.g., U.S. Pat. Nos. 9,233,985, 10,065,974, 10,287,303, 8,524,867, the disclosures of which are incorporated by reference herein in their entireties).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like.

In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating V617F in tissue samples, including human, and for identifying V617F inhibitors by binding of a labeled compound. Substitution of one or more of the atoms of the compounds of the present disclosure can also be useful in generating differentiated ADME (Adsorption, Distribution, Metabolism and Excretion.) Accordingly, the present disclosure includes V617F assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula I can be optionally substituted with deuterium atoms, such as —CD$_3$ being substituted for —CH$_3$). In some embodiments, alkyl groups of the disclosed Formulas (e.g., Formula I) can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a C$_{1-6}$ alkyl group can be replaced by deuterium atoms, such as —CD$_3$ being substituted for —CH$_3$). In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of alkyl, alkenyl, alkynyl, aryl, phenyl, cycloalkyl, heterocycloalkyl, or heteroaryl substituents or —C$_{1-4}$ alkyl-, alkylene, alkenylene and alkynylene linking groups, as described herein, are optionally replaced by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances, (see e.g., A. Kerekes et. al. *J. Med Chem.* 2011, 54, 201-210; R. Xu et. al. J. *Label Compd Radiopharm.* 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro V617F labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind V617F by monitoring its concentration variation when contacting with V617F, through tracking of the labeling. For example, a test compound (labeled) can be evaluated for its ability to reduce binding of another compound which is known to bind to V617F (i.e., standard compound). Accordingly, the ability of a test compound to compete with the standard compound for binding to V617F directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of V617F-associated diseases or disorders as described herein, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ C$_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ C$_{18}$ 5 μm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)). Typically, the flow rate used with the 30×100 mm column was 60 mL/minute.

pH=10 purifications: Waters XBridge $C_{18}$ 5 μm, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)). Typically, the flow rate used with 30×100 mm column was 60 mL/minute. The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. N-(4-((2-Methoxy-3-(1H-pyrazol-4-yl)phenyl)amino)-5-oxo-5,6-dihydro-1,6-naphthyridin-2-yl)cyclopropanecarboxamide

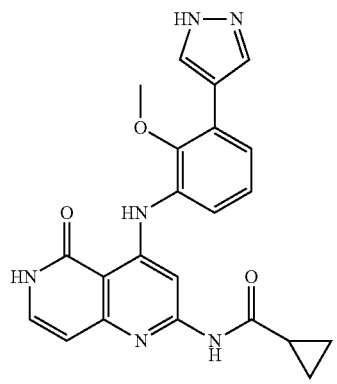 [SMILES: COc1c(Nc2cc(NC(=O)C3CC3)nc3cc[nH]c(=O)c23)cccc1-c1cn[nH]c1]

Step 1. 2,4-Dichloro-1,6-naphthyridin-5(6H)-one

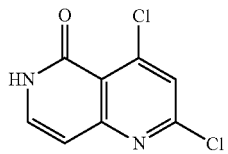 [SMILES: O=c1[nH]ccc2nc(Cl)cc(Cl)c12]

To a suspension of NaH (60% in mineral oil, 1.2 g, 30.0 mmol) in DMF (2.2 mL) and toluene (34 mL) was added a solution of ethyl 4,6-dichloro-2-methylnicotinate (4.0 g, 17 mmol, Ambeed A144974) in DMF (2.2 mL), dropwise. After stirring for 50 min at room temperature, 1,3,5-triazine (1.9 g, 24 mmol, Enamine EN300-73629) in DMF (10.0 mL) was added, and the mixture was heated at 100° C. for 1 hour. Upon cooling to room temperature, the reaction mixture was poured into a saturated $NH_4Cl$ (aq.) solution (40.0 mL). This mixture was diluted with water and EtOAc, and was filtered through Celite®, to collect the dark precipitate. The layers of the filtrate were separated and the aqueous layer was extracted with EtOAc (3×100 mL). The combined organic extracts were dried over $Na_2SO_4$, filtered, combined with the previously obtained dark precipitate, and concentrated. The residue was then purified on a silica gel column, eluting with a gradient of 0-70% EtOAc in hexanes to afford the title compound as a white solid (1.2 g, 32%). LCMS for $C_8H_5Cl_2N_2O$ $(M+H)^+$: calculated m/z=215.0; found 215.0.

Step 2. 2-Methoxy-3-(1-(tetrahydro-2H-pyran-2-yl)-1H-pyrazol-4-yl)aniline

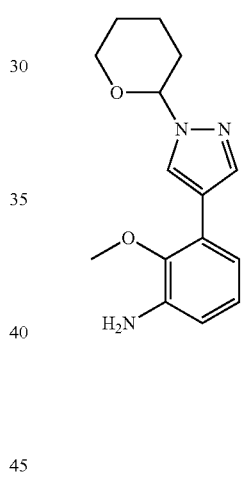

To a mixture of 3-bromo-2-methoxyaniline (2.1 g, 10.0 mmol, Combi-Blocks SS-3791) and 1-(tetrahydro-2H-pyran-2-yl)-4-(4,4,5,5-tetramethyl-1,3,2-dioxaborolan-2-yl)-1H-pyrazole (4.1 g, 15 mmol, AstaTech 82915) in dioxane (60.0 mL) was added $PdCl_2(dppf)$-$CH_2Cl_2$ adduct (0.85 g, 1.0 mmol), and $K_2CO_3$ solution (1.0 M in water, 31 mL, 31 mmol). The mixture was degassed by sparging with $N_2$, then the reaction vessel was sealed and heated to 90° C. for 1.5 hours. Upon cooling to room temperature, the reaction mixture was partitioned between EtOAc and water. The layers were separated, and the aqueous layer was extracted with two further portions of EtOAc. The combined organic extracts were dried over $Na_2SO_4$, filtered, and concentrated. The residue was purified on a silica gel column, eluting with a gradient of 0-60% EtOAc in hexanes to afford a solid (2.6 g, 91%). LCMS for $C_{15}H_{20}N_3O_2$ $(M+H)^+$: calculated m/z=274.2; found 274.1.

Step 3. 2-Chloro-4-((2-methoxy-3-(1-(tetrahydro-2H-pyran-2-yl)-1H-pyrazol-4-yl)phenyl)amino)-1,6-naphthyridin-5(6H)-one

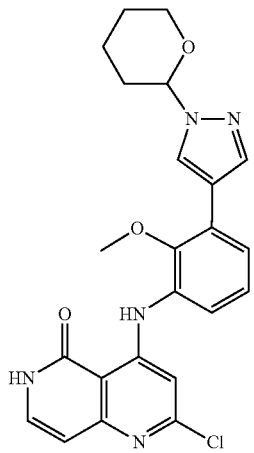 [SMILES: COc1c(Nc2cc(Cl)nc3cc[nH]c(=O)c23)cccc1-c1cnn(C2CCCCO2)c1]

To a solution of 2,4-dichloro-1,6-naphthyridin-5(6H)-one (0.10 g, 0.47 mmol, from Example 1, Step 1) and 2-methoxy-3-(1-(tetrahydro-2H-pyran-2-yl)-1H-pyrazol-4-yl)aniline (0.13 g, 0.47 mmol) in THF (5.0 mL) at 0° C. was added a solution of LiHMDS, dropwise (1.0 M in THF, 1.6 mL, 1.6 mmol). After stirring for 25 min at 0° C., the reaction was quenched by the addition of saturated NH$_4$Cl (aq.) solution (5.0 mL). The mixture was diluted with water (5.0 mL) and extracted with two portions of EtOAc. The combined organic extracts were dried over Na$_2$SO$_4$, filtered, and concentrated. The residue was purified on a silica gel column, eluting with a gradient of 0-100% EtOAc in hexanes to afford the product as a solid (60.0 mg, 29%). LCMS for C$_{23}$H$_{23}$ClN$_5$O$_3$ (M+H)$^+$: calculated m/z=452.1; found 452.2.

Step 4. N-(4-((2-Methoxy-3-(1H-pyrazol-4-yl)phenyl)amino)-5-oxo-5,6-dihydro-1,6-naphthyridin-2-yl)cyclopropanecarboxamide A mixture of 2-chloro-4-((2-methoxy-3-(1-(tetrahydro-2H-pyran-2-yl)-1H-pyrazol-4-yl)phenyl)amino)-1,6-naphthyridin-5(6H)-one (120 mg, 0.27 mmol), cyclopropanecarboxamide (110 mg, 1.3 mmol), 9,9-dimethyl-4,5-bis(diphenylphosphino)xanthene (26 mg, 0.045 mmol), tris(dibenzylideneacetone)dipalladium(0) (24 mg, 0.027 mmol), and Cs$_2$CO$_3$ (220 mg, 0.66 mmol) in dioxane (3.0 mL) was degassed by sparging with N$_2$, then the reaction vessel was sealed and heated at 100° C. for 2 hours. Upon cooling to room temperature, the reaction mixture was diluted with MeOH and DCM, filtered through Celite®, and the filtrate was concentrated. The resulting residue was dissolved in a mixture of DCM and MeOH (1:1, 20.0 mL), then HCl in dioxane (4.0 M, 0.66 mL, 2.7 mmol) was added. The reaction mixture was stirred for 1 hour, then solvents were removed in vacuo. The residue was dissolved in MeOH, and the resulting solution was filtered and purified via preparative HPLC-MS (pH=10) to afford the title compound (48 mg, 43%). LCMS for C$_{22}$H$_{21}$N$_6$O$_3$ (M+H)$^+$: calculated m/z=417.2; found 417.2. $^1$H NMR (500 MHz, DMSO-d$_6$) δ 13.00 (s, 1H), 11.70 (s, 1H), 11.43 (d, J=5.5 Hz, 1H), 10.80 (s, 1H), 8.31-7.90 (br m, 2H), 7.95 (s, 1H), 7.45 (dd, J=7.9, 1.5 Hz, 1H), 7.40-7.32 (m, 2H), 7.19 (t, J=7.9 Hz, 1H), 6.35 (d, J=7.3 Hz, 1H), 3.60 (s, 3H), 2.02 (tt, J=7.3, 5.3 Hz, 1H), 0.83-0.74 (m, 4H).

Example 2. N-(4-((2-Methoxy-3-(2-(tetrahydro-2H-pyran-4-yl)thiazol-5-yl)phenyl)amino)-5-oxo-5,6-dihydro-1,6-naphthyridin-2-yl)cyclopropanecarboxamide Trifluoroacetic Acid Salt

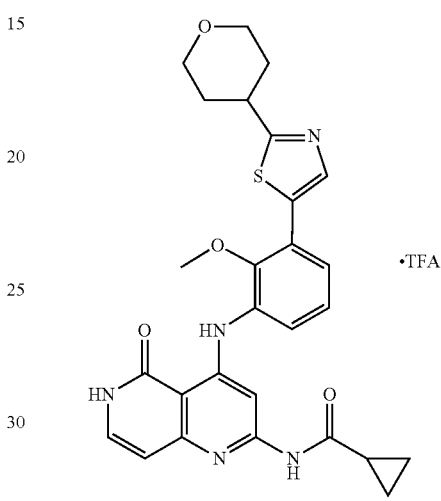

Step 1. 5-Bromo-2-(3,6-dihydro-2H-pyran-4-yl)thiazole

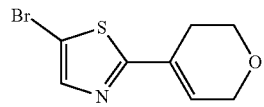 [SMILES: Brc1cnc(C2=CCOCC2)s1]

A mixture of 2-(3,6-dihydro-2H-pyran-4-yl)-4,4,5,5-tetramethyl-1,3,2-dioxaborolane (0.95 g, 4.5 mmol, AstaTech 82912), 2,5-dibromothiazole (1.0 g, 4.1 mmol, Aldrich 524182), Cs$_2$CO$_3$ (1.6 g, 4.9 mmol) and Pd(Ph$_3$P)$_4$ (0.095 g, 0.082 mmol) in dioxane (25 mL) and water (12 mL) was degassed by sparging with N$_2$, then the reaction vessel was sealed and heated at 120° C. for 3.5 hours. Additional Pd(Ph$_3$P)$_4$ (0.048 g, 0.041 mmol) was added, and the mixture was heated for an additional 16.5 hours at 120° C. Upon cooling to room temperature, the reaction mixture was partitioned between EtOAc and water. The organic layer was dried over Na$_2$SO$_4$, filtered, and concentrated. Purification on a silica gel column, eluting with a gradient of 0-10% EtOAc in hexanes afforded the title compound as a white solid (0.34 g, 33%). LCMS for C$_8$H$_9$BrNOS (M+H)$^+$: calculated m/z=246.0; found 245.9.

Step 2. 3-(2-(3,6-dihydro-2H-pyran-4-yl)thiazol-5-yl)-2-methoxyaniline

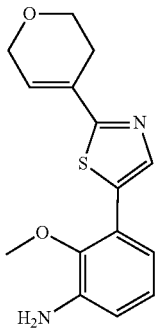 [SMILES: COc1c(N)cccc1-c1cnc(C2=CCOCC2)s1]

To a mixture of 2-methoxy-3-(4,4,5,5-tetramethyl-1,3,2-dioxaborolan-2-yl)aniline (0.34 g, 1.4 mmol, Combi-Blocks PN-1956) and 5-bromo-2-(3,6-dihydro-2H-pyran-4-yl)thiazole (0.34 g, 1.4 mmol) in dioxane (8.0 mL) was added PdCl$_2$(dppf)-CH$_2$Cl$_2$ adduct (0.11 g, 0.14 mmol) and K$_2$CO$_3$ solution (1.0 M in water, 4.1 mL, 4.1 mmol). The mixture was degassed by sparging with N$_2$, then the reaction vessel was sealed and heated at 90° C. for 1 h. Upon cooling to room temperature, the reaction mixture was diluted with EtOAc and water, the biphasic mixture was filtered through Celite®, and the layers of the filtrate were separated. The aqueous layer was extracted with two further portions of EtOAc. The combined organic extracts were dried over Na$_2$SO$_4$, filtered, and concentrated. Purification on silica gel column, eluting with a gradient of 0-40% EtOAc in hexanes, afforded the title compound as a light yellow solid (0.14 g, 36%). LCMS for C$_{15}$H$_{17}$N$_2$O$_2$S (M+H)$^+$: calculated m/z=289.1; found 289.1.

Step 3. 2-Methoxy-3-(2-(tetrahydro-2H-pyran-4-yl)thiazol-5-yl)aniline

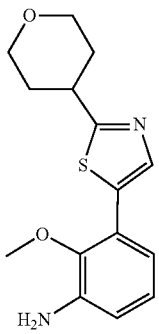 [SMILES: COc1c(N)cccc1-c1cnc(C2CCOCC2)s1]

To a solution of 3-(2-(3,6-dihydro-2H-pyran-4-yl)thiazol-5-yl)-2-methoxyaniline (140 mg, 0.50 mmol) in EtOH (15 mL) was added ammonium formate (1.3 g, 20 mmol) and palladium on carbon (10%, 53 mg, 0.050 mmol). The reaction mixture was heated at 80° C. for 1 h under N$_2$. The mixture was cooled to room temperature, filtered through Celite®, and the solvent was removed in vacuo. The resulting residue was dissolved in DCM and the organic solution was washed with water, followed by brine, dried over Na$_2$SO$_4$, filtered, and concentrated to afford an oil that solidified on standing and was used without further purification (0.11 g, 76%). LCMS for C$_{15}$H$_{19}$N$_2$O$_2$S (M+H)$^+$: calculated m/z=291.1; found 291.1.

Step 4. 2-Chloro-4-((2-methoxy-3-(2-(tetrahydro-2H-pyran-4-yl)thiazol-5-yl)phenyl)amino)-1,6-naphthyridin-5(6H)-one

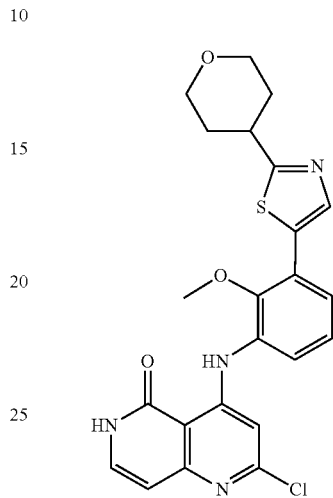

To a solution of 2,4-dichloro-1,6-naphthyridin-5(6H)-one (30.0 mg, 0.140 mmol, prepared as in Example 1, Step 1) and 2-methoxy-3-(2-(tetrahydro-2H-pyran-4-yl)thiazol-5-yl)aniline (28 mg, 0.098 mmol) in THF (1.0 mL) at 0° C. was added a solution of LiHMDS (1.0 M in THF, 0.49 mL, 0.49 mmol) in a dropwise manner. After stirring for 30 min at 0° C., the reaction mixture was quenched by the addition of saturated NH$_4$Cl solution (2.0 mL). Water (5.0 mL) was added, and the mixture was extracted twice with EtOAc. The combined organic extracts were dried over MgSO$_4$, filtered and concentrated to afford the title compound as a solid which was used without further purification (theoretical yield assumed). LCMS for C$_{23}$H$_{22}$ClN$_4$O$_3$S (M+H)$^+$: calculated m/z=469.1; found 469.3.

Step 5. N-(4-((2-Methoxy-3-(2-(tetrahydro-2H-pyran-4-yl)thiazol-5-yl)phenyl)amino)-5-oxo-5,6-dihydro-1,6-naphthyridin-2-yl)cyclopropanecarboxamide Trifluoroacetic Acid Salt A mixture of 2-chloro-4-((2-methoxy-3-(2-(tetrahydro-2H-pyran-4-yl)thiazol-5-yl)phenyl)amino)-1,6-naphthyridin-5(6H)-one (45 mg, 0.096 mmol), cyclopropanecarboxamide (25 mg, 0.29 mmol), 9,9-dimethyl-4,5-bis(diphenylphosphino)xanthene (9.4 mg, 0.016 mmol), tris(dibenzylideneacetone)dipalladium(0) (8.8 mg, 9.6 µmol) and Cs$_2$CO$_3$ (78 mg, 0.24 mmol) in dioxane (1.0 mL) was degassed by sparging with N$_2$. The mixture was then heated at 110° C. for 40 min. Upon cooling to room temperature, the reaction mixture was diluted with MeOH and the solution was filtered and was purified via preparative HPLC-MS (pH=2) to afford the title compound as a white solid (9.4 mg, 16%). LCMS for C$_{27}$H$_{28}$N$_5$O$_4$S (M+H)$^+$: calculated m/z=518.2; found 518.2.

Example 3. N-(4-((3-(1-Cyclopentyl-1H-pyrazol-4-yl)-2-methoxyphenyl)amino)-5-oxo-5,6-dihydro-1,6-naphthyridin-2-yl)cyclopropanecarboxamide Trifluoroacetic Acid Salt

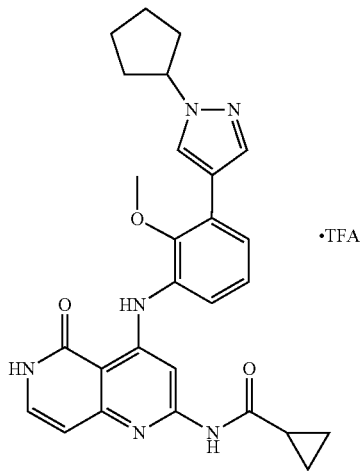 [SMILES: COc1c(Nc2cc(NC(=O)C3CC3)nc3cc[nH]c(=O)c23)cccc1-c1cnn(C2CCCC2)c1]

Step 1.
3-(1-Cyclopentyl-1H-pyrazol-4-yl)-2-methoxyaniline

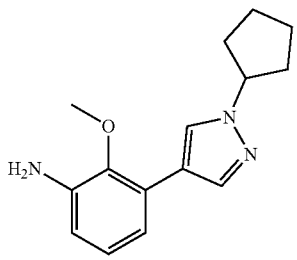 [SMILES: COc1c(N)cccc1-c1cnn(C2CCCC2)c1]

A degassed mixture of 1-cyclopentyl-4-(4,4,5,5-tetramethyl-1,3,2-dioxaborolan-2-yl)-1H-pyrazole (0.28 g, 1.1 mmol, AstaTech 86491), 3-bromo-2-methoxyaniline (0.21 g, 1.1 mmol, Combi-Blocks SS-3791), Na$_2$CO$_3$ solution (1.0 M, 2.6 mL, 2.6 mmol) and PdCl$_2$(dppf)-CH$_2$Cl$_{1-2}$ adduct (0.043 g, 0.053 mmol) in dioxane (11 mL) was heated to 110° C. for 2 hours, then was stirred overnight at room temperature. The reaction mixture was diluted with EtOAc, and the mixture was filtered and evaporated. Purification via silica gel chromatography, eluting with a gradient of 0-100% EtOAc in hexanes afforded the title compound (0.14 g, 50%). LCMS for C$_{15}$H$_{20}$N$_3$O (M+H)$^+$: calculated m/z=258.2; found 258.0.

Step 2. 2-Chloro-4-((3-(1-cyclopentyl-1H-pyrazol-4-yl)-2-methoxyphenyl)amino)-1,6-naphthyridin-5(6H)-one

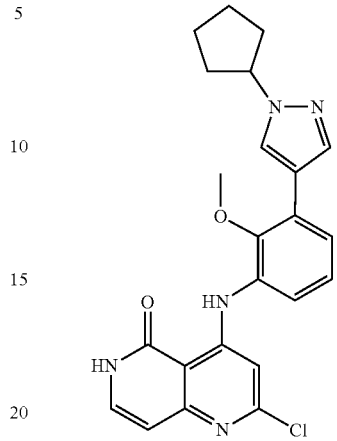

The title compound was prepared according to the procedures described for Example 2, Step 4, using 3-(1-cyclopentyl-1H-pyrazol-4-yl)-2-methoxyaniline (25 mg, 0.098 mmol) in place of 2-methoxy-3-(2-(tetrahydro-2H-pyran-4-yl)thiazol-5-yl)aniline. LCMS for C$_{23}$H$_{23}$ClN$_5$O$_2$ (M+H)$^+$: calculated m/z=436.2; found 436.4.

Step 3. N-(4-((3-(1-Cyclopentyl-1H-pyrazol-4-yl)-2-methoxyphenyl)amino)-5-oxo-5,6-dihydro-1,6-naphthyridin-2-yl)cyclopropanecarboxamide Trifluoroacetic Acid Salt The title compound was prepared according to the procedures described for Example 2, Step 5, using 2-chloro-4-((3-(1-cyclopentyl-1H-pyrazol-4-yl)-2-methoxyphenyl)amino)-1,6-naphthyridin-5(6H)-one (43 mg, 0.099 mmol) in place of 2-chloro-4-((2-methoxy-3-(2-(tetrahydro-2H-pyran-4-yl)thiazol-5-yl)phenyl)amino)-1,6-naphthyridin-5(6H)-one. Purification via preparative HPLC-MS (pH=2) afforded the title compound as a white solid (7.4 mg, 13%). LCMS for C$_{27}$H$_{29}$N$_6$O$_3$ (M+H)$^+$: calculated m/z=485.2; found 485.2.

Example 4. N-(4-((3-(4-(Cyclopropylsulfonyl)piperazin-1-yl)-2-methoxyphenyl)amino)-5-oxo-5,6-dihydro-1,6-naphthyridin-2-yl)cyclopropanecarboxamide Trifluoroacetic Acid Salt

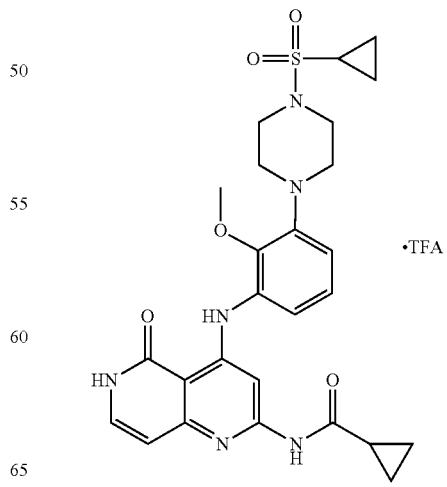

Step 1. tert-Butyl 4-(2-methoxy-3-nitrophenyl)piperazine-1-carboxylate

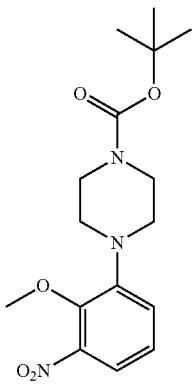 [SMILES: COc1c(N2CCN(C(=O)OC(C)(C)C)CC2)cccc1[N+](=O)[O-]]

A mixture of 1-bromo-2-methoxy-3-nitrobenzene (0.50 g, 2.2 mmol, Combi-Blocks HC-6745), tert-butyl piperazine-1-carboxylate (0.60 g, 3.2 mmol, Aldrich 343536), $Cs_2CO_3$ (1.4 g, 4.3 mmol), $Pd_2(dba)_3$ (0.37 g, 0.40 mmol) and xantphos (0.36 g, 0.62 mmol) in dioxane (15 mL) was degassed by sparging with $N_2$, then the mixture was heated at 110° C. for 3 hours. Upon cooling to room temperature, the reaction mixture was diluted with EtOAc, the mixture was filtered through Celite®, and the filtrate was concentrated. Purification on a 120 g silica gel column, eluting with a gradient of 0-20% EtOAc in hexanes, afforded the title compound as a yellow solid (0.64 g, 88%). LCMS for $C_{16}H_{24}N_3O_5$ (M+H)$^+$: calculated m/z=338.2; found 338.1.

Step 2. 1-(2-Methoxy-3-nitrophenyl)piperazine Hydrochloric Acid Salt

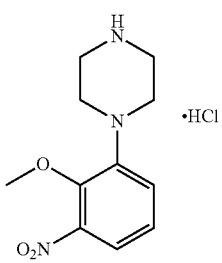 [SMILES: COc1c(N2CCNCC2)cccc1[N+](=O)[O-] ; Cl]

To a solution of tert-butyl 4-(2-methoxy-3-nitrophenyl)piperazine-1-carboxylate (0.10 g, 0.30 mmol) in DCM (5.0 mL) was added HCl in dioxane (4.0 M, 0.74 mL, 3.0 mmol). The mixture was stirred for 2 hours, then volatiles were removed in vacuo to afford the title compound as a solid, which was used without further purification. LCMS for $C_{11}H_{16}N_3O_3$ (M+H)$^+$: calculated m/z=238.1; found 238.1.

Step 3. 1-(Cyclopropylsulfonyl)-4-(2-methoxy-3-nitrophenyl)piperazine

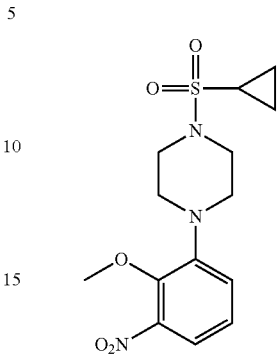

To 1-(2-methoxy-3-nitrophenyl)piperazine hydrochloric acid salt (81 mg, 0.30 mmol) in DCM (3.0 mL) was added triethylamine (0.12 mL, 0.89 mmol). The mixture was cooled to 0° C., then cyclopropanesulfonyl chloride (45 µL, 0.44 mmol) was added. The reaction mixture was warmed to room temperature and allowed to stir for 2 hours. Volatiles were removed in vacuo. Purification on a 40 g silica gel column, eluting with a gradient of 0-50% EtOAc in hexanes, afforded the title compound as an oil (74 mg, 73%). LCMS for $C_{14}H_{20}N_3O_5S$ (M+H)$^+$: calculated m/z=342.1; found 342.1.

Step 4. 3-(4-(Cyclopropylsulfonyl)piperazin-1-yl)-2-methoxyaniline

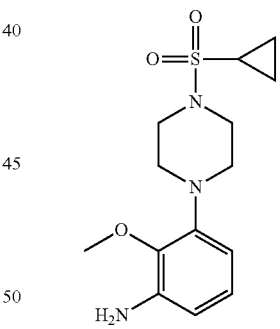

A mixture of 1-(cyclopropylsulfonyl)-4-(2-methoxy-3-nitrophenyl)piperazine (74 mg, 0.22 mmol), zinc (dust, 140 mg, 2.2 mmol) and $NH_4Cl$ (120 mg, 2.2 mmol) in ethanol (4.0 mL) and water (0.60 mL) was stirred at room temperature for 1 h. The mixture was diluted with DCM (30 mL) and filtered. The filtrate was washed with brine. The aqueous layer was back extracted with DCM. The combined organic extracts were dried over $Na_2SO_4$, filtered and concentrated to afford the product as an off-white solid (65 mg, 96%). LCMS for $C_{14}H_{22}N_3O_3S$ (M+H)$^+$: calculated m/z=312.1; found 312.1.

Step 5. 2-Chloro-4-((3-(4-(cyclopropylsulfonyl)piperazin-1-yl)-2-methoxyphenyl)amino)-1,6-naphthyridin-5(6H)-one

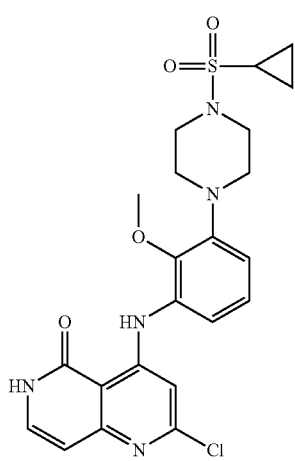 [SMILES: COc1c(Nc2cc(Cl)nc3cc[nH]c(=O)c23)cccc1N1CCN(S(=O)(=O)C2CC2)CC1]

The title compound was prepared according to the procedures described for Example 2, Step 4, using 3-(4-(cyclopropylsulfonyl)piperazin-1-yl)-2-methoxyaniline (30.0 mg, 0.098 mmol) in place of 2-methoxy-3-(2-(tetrahydro-2H-pyran-4-yl)thiazol-5-yl)aniline. LCMS for $C_{22}H_{25}ClN_5O_4S$ (M+H)$^+$: calculated m/z=490.1; found 490.2.

Step 6. N-(4-((3-(4-(Cyclopropylsulfonyl)piperazin-1-yl)-2-methoxyphenyl)amino)-5-oxo-5,6-dihydro-1,6-naphthyridin-2-yl)cyclopropanecarboxamide Trifluoroacetic Acid Salt The title compound was prepared according to the procedures described for Example 2, Step 5, using 2-chloro-4-((3-(4-(cyclopropylsulfonyl)piperazin-1-yl)-2-methoxyphenyl)amino)-1,6-naphthyridin-5(6H)-one (48 mg, 0.097 mmol) in place of 2-chloro-4-((2-methoxy-3-(2-(tetrahydro-2H-pyran-4-yl)thiazol-5-yl)phenyl)amino)-1,6-naphthyridin-5(6H)-one. Purification via preparative HPLC-MS (pH=2) afforded the title compound as a white solid (15 mg, 23%). LCMS for $C_{26}H_{31}N_6O_5S$ (M+H)$^+$: calculated m/z=539.2; found 539.2.

Example 5. N-(4-((2-Methoxy-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide Trifluoroacetic Acid Salt

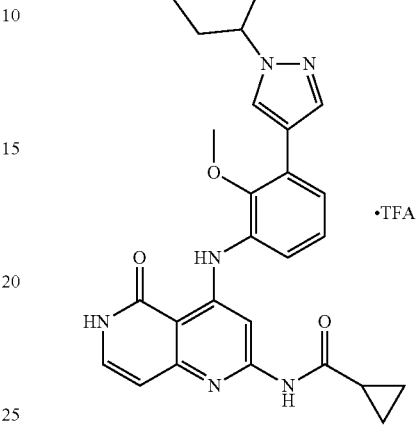

Step 1. 2-Methoxy-3-(1-(tetrahydro-2H-pyran-4-yl)-1H-pyrazol-4-yl)aniline

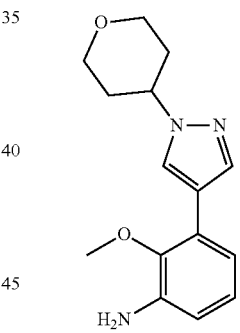

To a mixture of 3-bromo-2-methoxyaniline (130 mg, 0.64 mmol, Combi-Blocks SS-3791) and 1-(tetrahydro-2H-pyran-4-yl)-4-(4,4,5,5-tetramethyl-1,3,2-dioxaborolan-2-yl)-1H-pyrazole (270 mg, 0.97 mmol, AstaTech 81632) in dioxane (3.0 mL) was added PdCl$_2$(dppf)-CH$_2$Cl$_2$ adduct (53 mg, 0.064 mmol) and K$_2$CO$_3$ solution (1.0 M in water, 1.9 mL, 1.9 mmol). The mixture was degassed by sparging with N$_2$, and was heated to 90° C. for 1.5 hours. Upon cooling to room temperature, the reaction mixture was partitioned between water and EtOAc. The aqueous layer was extracted with two further portions of EtOAc. The combined organic extracts were dried over Na$_2$SO$_4$, filtered and concentrated. The residue was purified via preparative HPLC-MS (pH=10) to afford the title compound (160 mg, 92%). LCMS for $C_{15}H_{20}N_3O_2$ (M+H)$^+$: calculated m/z=274.2; found 274.1.

Step 2. 2-Chloro-4-((2-methoxy-3-(1-(tetrahydro-2H-pyran-4-yl)-1H-pyrazol-4-yl)phenyl)amino)-1,6-naphthyridin-5(6H)-one

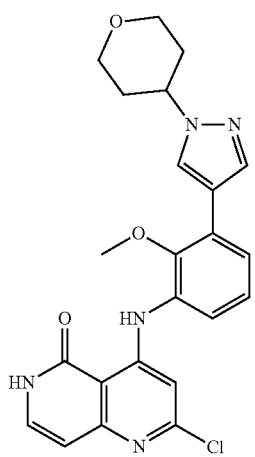 [SMILES: COc1c(Nc2cc(Cl)nc3cc[nH]c(=O)c23)cccc1-c1cnn(C2CCOCC2)c1]

The title compound was prepared according to the procedures described for Example 2, Step 4, using 2-methoxy-3-(1-(tetrahydro-2H-pyran-4-yl)-1H-pyrazol-4-yl)aniline (13 mg, 0.049 mmol) in place of 2-methoxy-3-(2-(tetrahydro-2H-pyran-4-yl)thiazol-5-yl)aniline. LCMS for $C_{23}H_{23}ClN_5O_3$ (M+H)$^+$: calculated m/z=452.1; found 452.1.

Step 3. N-(4-((2-Methoxy-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide Trifluoroacetic Acid Salt The title compound was prepared according to the procedures described for Example 2, Step 5, using 2-chloro-4-((2-methoxy-3-(1-(tetrahydro-2H-pyran-4-yl)-1H-pyrazol-4-yl)phenyl)amino)-1,6-naphthyridin-5(6H)-one (22 mg, 0.049 mmol) in place of 2-chloro-4-((2-methoxy-3-(2-(tetrahydro-2H-pyran-4-yl)thiazol-5-yl)phenyl)amino)-1,6-naphthyridin-5(6H)-one. Purification via preparative HPLC-MS (pH=2) afforded the title compound as a white solid (6.0 mg, 20%). LCMS for $C_{27}H_{29}N_6O_4$ (M+H)$^+$: calculated m/z=501.2; found 501.2.

Example 6. N-(5-oxo-4-((3-(1-(tetrahydro-2H-pyran-4-yl)-1H-pyrazol-4-yl)phenyl)amino)-5,6-dihydro-1,6-naphthyridin-2-yl)cyclopropanecarboxamide Trifluoroacetic Acid Salt

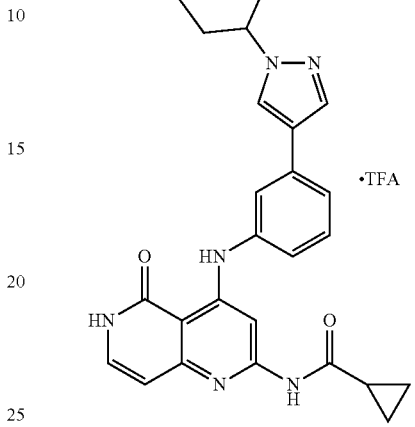

The title compound was prepared according to the procedures described for Example 5, using 3-bromoaniline (0.10 g, 0.58 mmol, Aldrich 180025) in place of 3-bromo-2-methoxyaniline in Step 1. Purification via preparative HPLC-MS (pH=2) afforded the title compound as a white solid (4.5 mg, 23%). LCMS for $C_{26}H_{27}N_6O_3$ (M+H)$^+$: calculated m/z=471.2; found 471.2.

Example 7. N-(4-((2-Methoxy-4-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide Trifluoroacetic Acid Salt

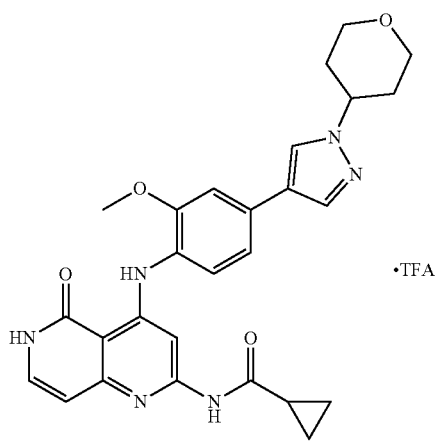 [SMILES: COc1cc(-c2cnn(C3CCOCC3)c2)ccc1Nc1cc(NC(=O)C2CC2)nc2cc[nH]c(=O)c12]

The title compound was prepared according to the procedures described for Example 5, using 4-bromo-2-methoxyaniline (0.10 g, 0.50 mmol, Enamine EN300-121196) in place of 3-bromo-2-methoxyaniline in Step 1. Purification via preparative HPLC-MS (pH=2) afforded the title compound as a solid (5.9 mg, 23%). LCMS for $C_{27}H_{29}N_6O_4$ (M+H)$^+$: calculated m/z=501.2; found 501.2.

Example 8. N-(4-((3-(1-(1-Amino-1-oxopropan-2-yl)-1H-pyrazol-4-yl)-2-methoxyphenyl)amino)-5-oxo-5,6-dihydro-1,6-naphthyridin-2-yl)cyclopropanecarboxamide Trifluoroacetic Acid Salt

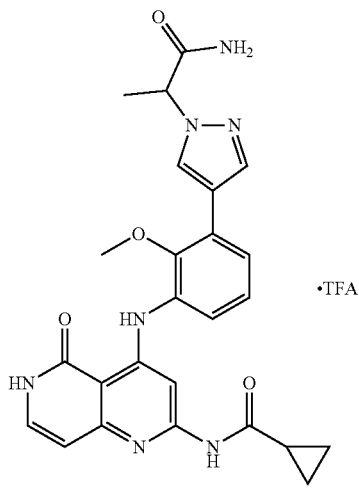 [SMILES: COc1c(Nc2cc(NC(=O)C3CC3)nc3cc[nH]c(=O)c23)cccc1-c1cnn(C(C)C(N)=O)c1]

Step 1. 2-(4-(3-Amino-2-methoxyphenyl)-1H-pyrazol-1-yl)propanamide

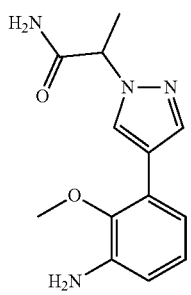 [SMILES: COc1c(N)cccc1-c1cnn(C(C)C(N)=O)c1]

To 2-methoxy-3-(1-(tetrahydro-2H-pyran-2-yl)-1H-pyrazol-4-yl)aniline (50.0 mg, 0.18 mmol, prepared as in Example 1, Step 2) was added TFA (0.14 mL, 1.8 mmol). The mixture was stirred for one hour, then volatiles were removed in vacuo. The residue was dissolved in DMF (0.40 mL), then 2-bromopropionamide (33 mg, 0.22 mmol, Aldrich 308595) and $Cs_2CO_3$ (360 mg, 1.1 mmol) were added. The suspension was heated at 50° C. for 1.5 hours. Upon cooling to room temperature, the reaction mixture was diluted with MeCN, and the mixture was filtered and purified via preparative HPLC-MS (pH=10) to afford the title compound (27 mg, 57%). LCMS for $C_{13}H_{17}N_4O_2$ $(M+H)^+$: calculated m/z=261.1; found 261.1.

Step 2. 2-(4-(3-((2-Chloro-5-oxo-5,6-dihydro-1,6-naphthyridin-4-yl)amino)-2-methoxyphenyl)-1H-pyrazol-1-yl)propanamide

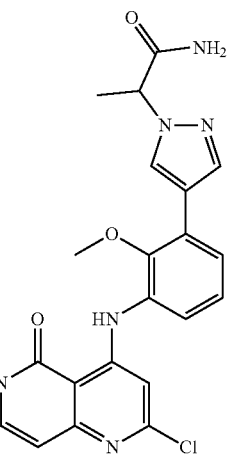

The title compound was prepared according to the procedures described for Example 2, Step 4, using 2-(4-(3-amino-2-methoxyphenyl)-1H-pyrazol-1-yl)propanamide (28 mg, 0.11 mmol) in place of 2-methoxy-3-(2-(tetrahydro-2H-pyran-4-yl)thiazol-5-yl)aniline. Purification via preparative HPLC-MS (pH=10) afforded the title compound (19 mg, 41%). LCMS for $C_{21}H_{20}ClN_6O_3$ $(M+H)^+$: calculated m/z=439.1; found 439.2. $^1H$ NMR (500 MHz, DMSO-$d_6$) δ 11.81 (s, 1H), 11.78 (s, 1H), 8.28 (s, 1H), 7.98 (s, 1H), 7.57 (dd, J=1.9, 1.6 Hz, 1H), 7.52-7.45 (m, 2H), 7.40 (dd, J=1.9, 1.5 Hz, 1H), 7.28-7.20 (m, 2H), 6.70 (s, 1H), 6.47 (d, J=7.2 Hz, 1H), 5.04 (q, J=7.1 Hz, 1H), 3.62 (s, 3H), 1.66 (d, J=1.2 Hz, 3H).

Step 3. N-(4-((3-(1-(1-Amino-1-oxopropan-2-yl)-1H-pyrazol-4-yl)-2-methoxyphenyl)amino)-5-oxo-5,6-dihydro-1,6-naphthyridin-2-yl)cyclopropanecarboxamide Trifluoroacetic Acid Salt The title compound was prepared according to the procedures described for Example 2, Step 5, using 2-(4-(3-((2-chloro-5-oxo-5,6-dihydro-1,6-naphthyridin-4-yl)amino)-2-methoxyphenyl)-1H-pyrazol-1-yl)propanamide (9.0 mg, 0.021 mmol) in place of 2-chloro-4-((2-methoxy-3-(2-(tetrahydro-2H-pyran-4-yl)thiazol-5-yl)phenyl)amino)-1,6-naphthyridin-5(6H)-one. Purification via preparative HPLC-MS (pH=2) afforded the title compound as a white solid (4.1 mg, 33%). LCMS for $C_{25}H_{26}N_7O_4$ $(M+H)^+$: calculated m/z=488.2; found 488.2.

Example 9. N-(4-((1-Ethyl-1H-indol-7-yl)amino)-5-oxo-5,6-dihydro-1,6-naphthyridin-2-yl)cyclopropanecarboxamide Trifluoroacetic Acid Salt

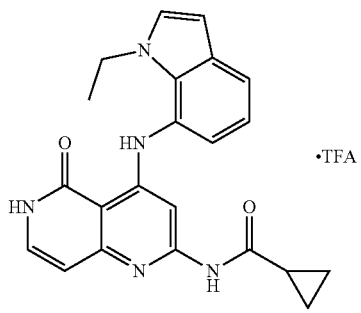 [SMILES: CCn1ccc2cccc(Nc3cc(NC(=O)C4CC4)nc4cc[nH]c(=O)c34)c21]

Step 1. 1-Ethyl-7-nitro-1H-indole

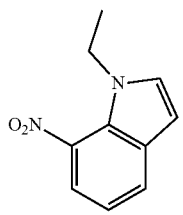

To a solution of 7-nitro-1H-indole (1.5 g, 9.2 mmol, Enamine EN300-118948) in DMF (9.3 mL) at 0° C. was added NaH (60% in mineral oil, 0.74 g, 18 mmol) in portions. The reaction was allowed to warm to room temperature and stir for 30 min. Iodoethane (1.1 mL, 14 mmol) was then added. After stirring for 5 hours, the reaction mixture was quenched by the addition of H$_2$O, and was extracted with EtOAc (2×). The combined organic extracts were twice washed with brine, dried over anhydrous Na$_2$SO$_4$, filtered and concentrated. The product was purified on a 120 g silica gel column, eluting with a gradient of 0-20% EtOAc in hexanes to afford the title compound as an oil (1.8 g, 100%). LCMS for C$_{10}$H$_{11}$N$_2$O$_2$ (M+H)$^+$: calculated m/z=191.1; found 191.1.

Step 2. 1-Ethyl-1H-indol-7-amine

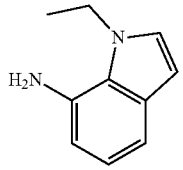

A mixture of 1-ethyl-7-nitro-1H-indole (0.10 g, 0.53 mmol), zinc (340 mg, 5.3 mmol) and NH$_4$Cl (280 mg, 5.3 mmol) in ethanol (3.0 mL) and water (0.45 mL) was stirred at room temperature for 40 min. The reaction was diluted with 20 mL DCM and the mixture was filtered. The filtrate was washed with brine. The aqueous layer was back extracted with DCM. The combined organic extracts were dried over Na$_2$SO$_4$, filtered and concentrated to afford the title compound as an oil, which was used without further purification (theoretical yield assumed). LCMS for C$_{10}$H$_{13}$N$_2$ (M+H)$^+$: calculated m/z=161.1; found 161.0.

Step 3. 2-Chloro-4-((1-ethyl-1H-indol-7-yl)amino)-1,6-naphthyridin-5(6H)-one

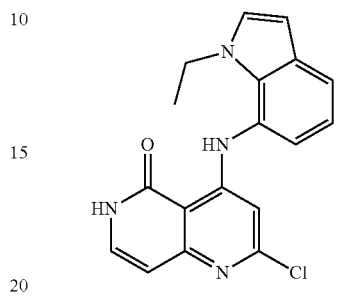

The title compound was prepared according to the procedures described for Example 2, Step 4, using 1-ethyl-1H-indol-7-amine (15 mg, 0.093 mmol) in place of 2-methoxy-3-(2-(tetrahydro-2H-pyran-4-yl)thiazol-5-yl)aniline. LCMS for C$_{18}$H$_{16}$ClN$_4$O (M+H)$^+$: calculated m/z=339.1; found 338.9.

Step 4. N-(4-((1-Ethyl-1H-indol-7-yl)amino)-5-oxo-5,6-dihydro-1,6-naphthyridin-2-yl)cyclopropanecarboxamide Trifluoroacetic Acid Salt The title compound was prepared according to the procedures described for Example 2, Step 5, using 2-chloro-4-((1-ethyl-1H-indol-7-yl)amino)-1,6-naphthyridin-5(6H)-one (32 mg, 0.094 mmol) in place of 2-chloro-4-((2-methoxy-3-(2-(tetrahydro-2H-pyran-4-yl)thiazol-5-yl)phenyl)amino)-1,6-naphthyridin-5(6H)-one. Purification via preparative HPLC-MS (pH=2) afforded the title compound as a solid. LCMS for C$_{22}$H$_{22}$N$_5$O$_2$ (M+H)$^+$: calculated m/z=388.2; found 388.1.

Example 10. N-(4-((2-Methoxy-3-(2-(tetrahydro-2H-pyran-4-yl)thiazol-5-yl)phenyl)amino)-6-methyl-5-oxo-5,6-dihydro-1,6-naphthyridin-2-yl)cyclopropanecarboxamide Trifluoroacetic Acid Salt

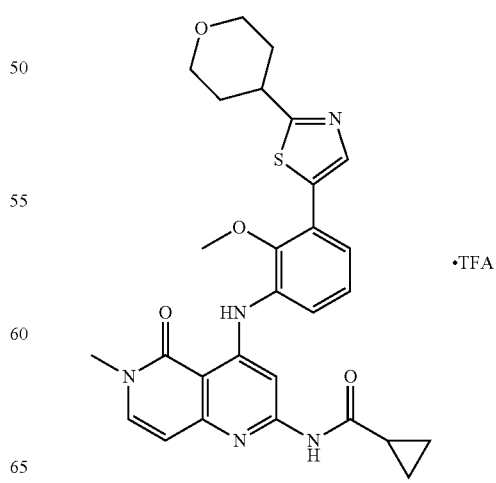

To a mixture of N-(4-((2-methoxy-3-(2-(tetrahydro-2H-pyran-4-yl)thiazol-5-yl)phenyl)amino)-5-oxo-5,6-dihydro-1,6-naphthyridin-2-yl)cyclopropanecarboxamide, trifluoroacetic acid salt (4.0 mg, 6.3 µmol, Example 2) and $K_2CO_3$ (2.3 mg, 0.016 mmol) in DMF (0.20 mL) was added methyl iodide (0.24 µl, 3.8 µmol) in DMF (0.10 mL) as an aliquot from a prepared stock solution. After stirring for 35 min, the reaction mixture was diluted with MeCN and MeOH, then was filtered and purified via preparative HPLC-MS (pH=2) to afford the title compound as a white solid (2.4 mg, 59%). LCMS for $C_{28}H_{30}N_5O_4S$ (M+H)$^+$: calculated m/z=532.2; found 532.2.

Example 11. 3-((2-(Cyclopropanecarboxamido)-5-oxo-5,6-dihydro-1,6-naphthyridin-4-yl)amino)-2-methoxy-N-((tetrahydro-2H-pyran-4-yl)methyl)benzamide Trifluoroacetic Acid Salt

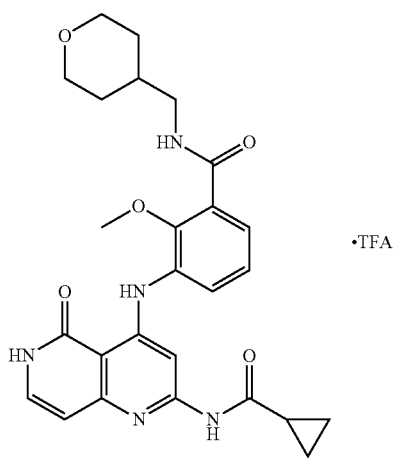 [SMILES: COc1c(Nc2cc(NC(=O)C3CC3)nc3cc[nH]c(=O)c23)cccc1C(=O)NCC1CCOCC1]

Step 1. N-(4-Chloro-5-oxo-5,6-dihydro-1,6-naphthyridin-2-yl)cyclopropanecarboxamide

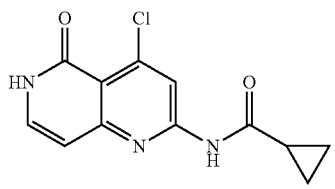 [SMILES: O=C(Nc1cc(Cl)c2c(=O)[nH]ccc2n1)C1CC1]

A mixture of 2,4-dichloro-1,6-naphthyridin-5(6H)-one (0.50 g, 2.3 mmol, from Example 1, Step 1), cyclopropanecarboxamide (0.20 g, 2.3 mmol), 9,9-dimethyl-4,5-bis(diphenylphosphino)xanthene (0.13 g, 0.23 mmol), tris(dibenzylideneacetone)dipalladium(0) (0.13 g, 0.14 mmol) and $Cs_2CO_3$ (1.9 g, 5.8 mmol) in dioxane (25 mL) was degassed by sparging with $N_2$. The reaction mixture was then heated at 80° C. for 4 hours. Additional cyclopropanecarboxamide (99 mg, 1.2 mmol), 9,9-dimethyl-4,5-bis(diphenylphosphino)xanthene (67 mg, 0.12 mmol) and tris(dibenzylideneacetone)dipalladium(0) (53 mg, 0.058 mmol) were added. The mixture was stirred at 80° C. for an additional 2 hours. Upon cooling to room temperature, the reaction mixture was diluted with EtOAc, MeOH and MeCN and filtered to remove insoluble material. The filtrate was evaporated, and the residue was purified on a 120 g silica gel column, eluting with a slow gradient of 0-100% EtOAc in hexanes to afford the title compound as a yellow solid (0.40 g, 65%). LCMS for $C_{12}H_{11}ClN_3O_2$ (M+H)$^+$: calculated m/z=264.0; found 264.0. $^1$H NMR (400 MHz, DMSO-d$_6$) δ 11.43 (s, 1H), 11.35 (s, 1H), 8.21 (s, 1H), 7.51-7.39 (m, 1H), 6.39 (d, J=7.3 Hz, 1H), 2.10-2.02 (m, 1H), 0.88 (m, 4H).

Step 2. Methyl 3-((2-(cyclopropanecarboxamido)-5-oxo-5,6-dihydro-1,6-naphthyridin-4-yl)amino)-2-methoxybenzoate

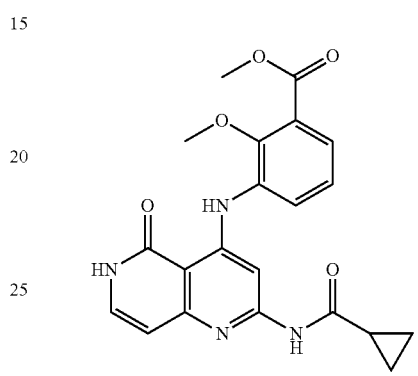

A mixture of N-(4-chloro-5-oxo-5,6-dihydro-1,6-naphthyridin-2-yl)cyclopropanecarboxamide (0.44 g, 1.7 mmol) and methyl 3-amino-2-methoxybenzoate, HCl salt (0.36 g, 1.7 mmol, Enamine EN300-263778) in 2-methoxyethanol (13 mL) was sealed and heated in the microwave at 140° C. for 20 min. Upon cooling, the reaction mixture was diluted with EtOAc and washed successively with saturated $NaHCO_3$ and brine. The organic layer was dried over $Na_2SO_4$, filtered and concentrated. The residue was purified on a 120 g silica gel column, eluting with a gradient of 0-5% MeOH in DCM to afford the title compound as a yellow solid (0.27 g, 40%). LCMS for $C_{21}H_{21}N_4O_5$ (M+H)$^+$: calculated m/z=409.1; found 409.1.

Step 3. 3-((2-(Cyclopropanecarboxamido)-5-oxo-5,6-dihydro-1,6-naphthyridin-4-yl)amino)-2-methoxybenzoic Acid

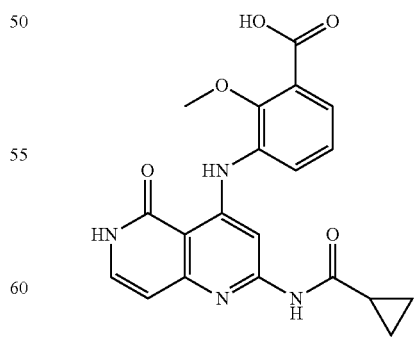

To a mixture of methyl 3-((2-(cyclopropanecarboxamido)-5-oxo-5,6-dihydro-1,6-naphthyridin-4-yl)amino)-2-methoxybenzoate (0.27 g, 0.66 mmol) in MeOH (15 mL) and THF (9.0 mL) was added NaOH solution (1.0 N in water, 2.6 mL, 2.6 mmol). The mixture was stirred at room temperature overnight. Additional NaOH solution (1.0 N in water, 0.66 mL, 0.66 mmol) was added and the solution was heated to 35° C. for 3 hours. Organic solvents were removed in vacuo. The resulting aqueous mixture was treated with 1.0 N HCl to achieve pH=3 to afford a precipitate that was isolated by filtration, washed with water and air-dried to afford the title compound as a yellow solid (0.20 g, 76%). LCMS for $C_{20}H_{19}N_4O_5$ (M+H)$^+$: calculated m/z=395.1; found 395.1.

Step 4. 3-((2-(Cyclopropanecarboxamido)-5-oxo-5,6-dihydro-1,6-naphthyridin-4-yl)amino)-2-methoxy-N-((tetrahydro-2H-pyran-4-yl)methyl)benzamide Trifluoroacetic Acid Salt To a solution of 3-((2-(cyclopropanecarboxamido)-5-oxo-5,6-dihydro-1,6-naphthyridin-4-yl)amino)-2-methoxybenzoic acid (7.0 mg, 0.018 mmol) in DMF (0.20 mL) was added HATU (6.8 mg, 0.018 mmol), triethylamine (12 µL, 0.089 mmol), and 4-aminomethyltetrahydropyran (6.1 mg, 0.053 mmol, AstaTech AB1593). The mixture was stirred for 30 min, then was diluted with MeOH, filtered and purified via preparative HPLC-MS (pH=2) to afford the title compound as a white solid (5.0 mg, 47%). LCMS for $C_{26}H_{30}N_5O_5$ (M+H)$^+$: calculated m/z=492.2; found 492.2.

Example 12. N-(4-((2-(Methylthio)-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide Trifluoroacetic Acid Salt

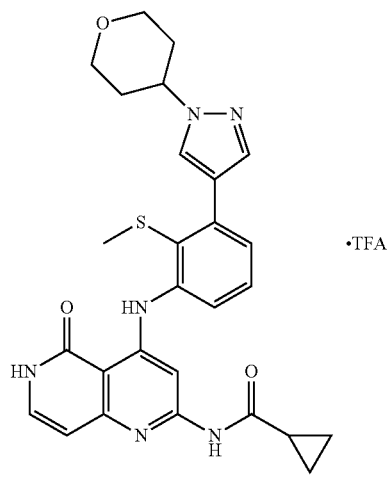 [SMILES: CSc1c(Nc2cc(NC(=O)C3CC3)nc3cc[nH]c(=O)c23)cccc1-c1cnn(C2CCOCC2)c1]

Step 1. (2-Bromo-6-nitrophenyl)(methyl)sulfane

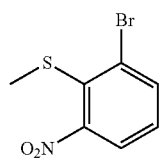

A solution of sodium thiomethoxide (1.2 g, 18 mmol) in water (5.0 mL) was added dropwise to a solution of 1-bromo-2-fluoro-3-nitrobenzene (3.0 g, 14 mmol, Enamine EN300-104712) in DMF (15 mL) at 0° C. After stirring for 1.5 hours at room temperature, the reaction mixture was added dropwise into water (60 mL) and was stirred for 30 min. The resulting light yellow solid was isolated by filtration and air-dried to afford the title compound (3.2 g, 95%).

Step 2. 4-(2-(Methylthio)-3-nitrophenyl)-1-(tetrahydro-2H-pyran-4-yl)-1H-pyrazole

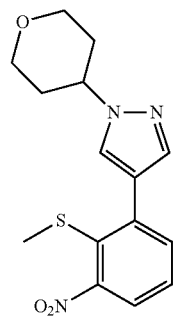 [SMILES: CSc1c(-c2cnn(C3CCOCC3)c2)cccc1[N+](=O)[O-]]

The title compound was prepared according to the procedures described for Example 5, Step 1, using (2-bromo-6-nitrophenyl)(methyl)sulfane (140 mg, 0.56 mmol) in place of 3-bromo-2-methoxyaniline, with the following modifications: the reaction mixture was heated at 90° C. overnight, and after workup, the residue was purified on a 40 g silica gel column, eluting with a gradient of 0-70% EtOAc in hexanes to afford the title compound as an oil (62 mg, 34%). LCMS for $C_{15}H_{18}N_3O_3S$ (M+H)$^+$: calculated m/z=320.1; found 320.1.

Step 3. 2-(Methylthio)-3-(1-(tetrahydro-2H-pyran-4-yl)-1H-pyrazol-4-yl)aniline

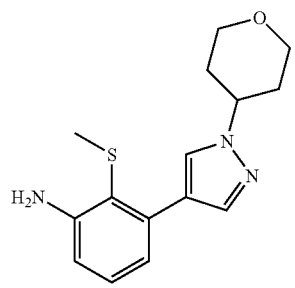 [SMILES: CSc1c(N)cccc1-c1cnn(C2CCOCC2)c1]

The title compound was prepared according to the procedures described for Example 9, Step 2, using 4-(2-(methylthio)-3-nitrophenyl)-1-(tetrahydro-2H-pyran-4-yl)-1H-pyrazole (62 mg, 0.19 mmol) in place of 1-ethyl-7-nitro-1H-indole. Workup as described afforded the title compound as an oil, which was used without further purification (55 mg, 98%). LCMS for $C_{15}H_{20}N_3OS$ (M+H)$^+$: calculated m/z=290.1; found 290.1.

Step 4. N-(4-((2-(Methylthio)-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide Trifluoroacetic Acid Salt To a mixture of N-(4-chloro-5-oxo-5,6-dihydro-1,6-naphthyridin-2-yl)cyclopropanecarboxamide (20.0 mg, 0.076 mmol, from Example 11, Step 1) and 2-(methylthio)-3-(1-(tetrahydro-2H-pyran-4-yl)-1H-pyrazol-4-yl)aniline (22 mg, 0.076 mmol) in 2-methoxyethanol (0.60 mL) was added HCl (4.0 M in dioxane, 19 μL, 0.076 mmol). The reaction vessel was sealed and heated at 140° C. in a microwave reactor for 20 min. Additional N-(4-chloro-5-oxo-5,6-dihydro-1,6-naphthyridin-2-yl)cyclopropanecarboxamide (30.0 mg, 0.11 mmol) was added, and the mixture was sealed and heated at 140° C. in the microwave for an additional 20 min. The reaction mixture was diluted with MeOH, filtered, and purified via preparative HPLC-MS (pH=2) to afford the title compound as a white solid (9.1 mg, 19%). LCMS for $C_{27}H_{29}N_6O_3S$ (M+H)⁺: calculated m/z=517.2; found 517.2.

Example 13. N-(4-((2-(Methylsulfonyl)-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide Trifluoroacetic Acid Salt

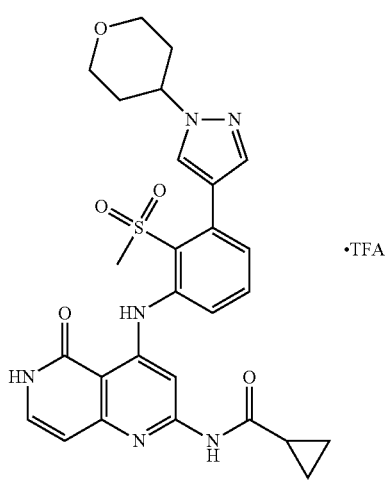 [SMILES: CS(=O)(=O)c1c(Nc2cc(NC(=O)C3CC3)nc3cc[nH]c(=O)c23)cccc1-c1cnn(C2CCOCC2)c1]

To a mixture of N-(4-((2-(methylthio)-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide trifluoroacetic acid salt (8.0 mg, 0.013 mmol, Example 12) in acetic acid (0.60 mL) was added hydrogen peroxide (30% (w/w) in water, 13 μL, 0.13 mmol), followed by sodium tungstate dihydrate (8.4 mg, 0.025 mmol). The reaction mixture was stirred for one hour. Additional hydrogen peroxide (30% (w/w) in water, 13 μL, 0.13 mmol) was added, and the reaction mixture was stirred for an additional 2.5 hours. Volatiles were removed in vacuo, and the residue was dissolved in a mixture of MeOH and water. The solution was filtered and purified via preparative HPLC-MS (pH=2) to afford the title compound as a white solid (4.9 mg, 58%). LCMS for $C_{27}H_{29}N_6O_5S$ (M+H)⁺: calculated m/z=549.2; found 549.2.

Example 14. N-(4-((2-Methoxy-3-(trifluoromethyl)phenyl)amino)-5-oxo-5,6-dihydro-1,6-naphthyridin-2-yl)cyclopropanecarboxamide Trifluoroacetic Acid Salt

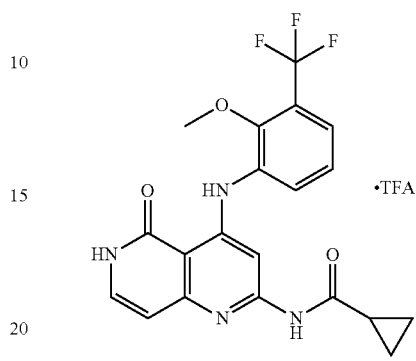

To a mixture of N-(4-chloro-5-oxo-5,6-dihydro-1,6-naphthyridin-2-yl)cyclopropanecarboxamide (10.0 mg, 0.038 mmol, from Example 11, Step 1) and 2-methoxy-3-(trifluoromethyl)aniline (7.3 mg, 0.038 mmol, Combi-Blocks QG-0595) in 2-methoxyethanol (0.20 mL) was added a solution of HCl in dioxane (4.0 M, 19 μL 0.076 mmol). The reaction vessel was sealed and heated at 140° C. for 10 minutes in the microwave. Upon cooling, the reaction mixture was diluted with MeOH, filtered and purified via preparative HPLC-MS (pH=2) to afford the title compound as a white solid (6.2 mg, 30%). LCMS for $C_{20}H_{18}F_3N_4O_3$ (M+H)⁺: calculated m/z=419.1; found 419.1.

Example 15. N-(4-((2,3-Dimethoxyphenyl)amino)-5-oxo-5,6-dihydro-1,6-naphthyridin-2-yl)cyclopropanecarboxamide Trifluoroacetic Acid Salt

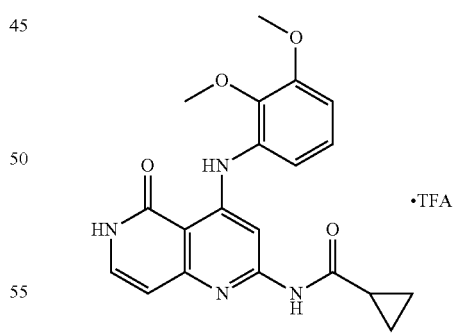

The title compound was prepared according to the procedures described for Example 14, using 2,3-dimethoxyaniline (5.8 mg, 0.038 mmol) in place of 2-methoxy-3-(trifluoromethyl)aniline. Purification via preparative HPLC-MS (pH=2) afforded the title compound as a white solid (7.5 mg, 41%). LCMS for $C_{20}H_{21}N_4O_4$ (M+H)⁺: calculated m/z=381.2; found 381.2.

Example 16. N-(4-((3-Chloro-2-(1H-pyrazol-4-yl)phenyl)amino)-5-oxo-5,6-dihydro-1,6-naphthyridin-2-yl)cyclopropanecarboxamide Trifluoroacetic Acid Salt

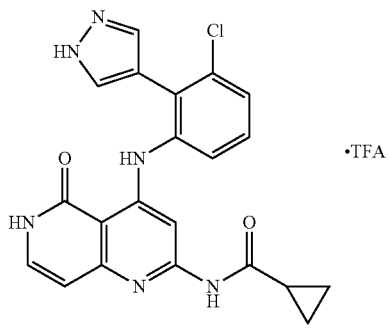 [SMILES: O=C(Nc1cc(Nc2cccc(Cl)c2-c2cn[nH]c2)c2c(=O)[nH]ccc2n1)C1CC1]

Step 1. 3-Chloro-2-(1H-pyrazol-4-yl)aniline

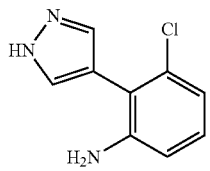

To a mixture of 2-bromo-3-chloroaniline (0.20 g, 0.97 mmol, AstaTech 36016) and 4-(4,4,5,5-tetramethyl-1,3,2-dioxaborolan-2-yl)-1H-pyrazole (190 mg, 0.97 mmol, AstaTech 65468) in dioxane (10.0 mL) was added $K_2CO_3$ solution (1.0 M in water, 2.9 mL, 2.9 mmol) and $PdCl_2$(dppf)-$CH_2Cl_2$ adduct (79 mg, 0.097 mmol). The mixture was degassed by sparging with $N_2$ and heated to 100° C. overnight. Upon cooling to room temperature, the reaction mixture was diluted with brine and extracted with EtOAc (2×). The combined organic extracts were dried over $Na_2SO_4$, filtered and concentrated. The product was purified via preparative HPLC-MS (pH=10) to afford the title compound as a light yellow solid (23 mg, 12%). LCMS for $C_9H_9ClN_3$ (M+H)+: calculated m/z=194.0; found 194.1.

Step 2. N-(4-((3-Chloro-2-(1H-pyrazol-4-yl)phenyl)amino)-5-oxo-5,6-dihydro-1,6-naphthyridin-2-yl)cyclopropanecarboxamide Trifluoroacetic Acid Salt The title compound was prepared according to the procedures described for Example 14, using 3-chloro-2-(1H-pyrazol-4-yl)aniline (5.9 mg, 0.030 mmol) in place of 2-methoxy-3-(trifluoromethyl)aniline. Purification via preparative HPLC-MS (pH=2) afforded the title compound as a white solid (3.1 mg, 19%). LCMS for $C_{21}H_{18}ClN_6O_2$ (M+H)+: calculated m/z=421.1; found 421.1.

Example 17. N-(4-((3-Chloro-2-(5-methyl-1H-pyrazol-4-yl)phenyl)amino)-5-oxo-5,6-dihydro-1,6-naphthyridin-2-yl)cyclopropanecarboxamide Trifluoroacetic Acid Salt

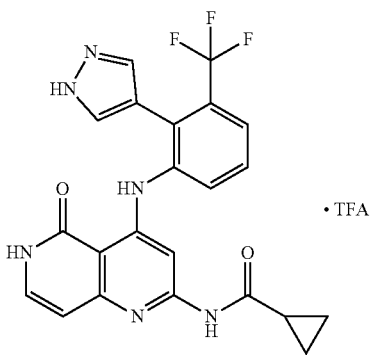 [SMILES: O=C(Nc1cc(Nc2cccc(C(F)(F)F)c2-c2cn[nH]c2)c2c(=O)[nH]ccc2n1)C1CC1]

The title compound was prepared according to the procedures described for Example 16, using 3-methyl-4-(4,4,5,5-tetramethyl-1,3,2-dioxaborolan-2-yl)-1H-pyrazole (0.20 g, 0.97 mmol, AstaTech 82902) in place of 4-(4,4,5,5-tetramethyl-1,3,2-dioxaborolan-2-yl)-1H-pyrazole in Step 1. Purification via preparative HPLC-MS (pH=2) afforded the title compound as a white solid (4.6 mg, 23%). LCMS for $C_{22}H_{20}ClN_6O_2$ (M+H)+: calculated m/z=435.1; found 435.2.

Example 18. N-(4-((2-(1H-pyrazol-4-yl)-3-(trifluoromethyl)phenyl)amino)-5-oxo-5,6-dihydro-1,6-naphthyridin-2-yl)cyclopropanecarboxamide Trifluoroacetic Acid Salt The title compound was prepared according to the procedures described for Example 16, using 2-bromo-3-(trifluoromethyl)aniline (150 mg, 0.63 mmol, Enamine EN300-119908) in place of 2-bromo-3-chloroaniline in Step 1. Purification via preparative HPLC-MS (pH=2) afforded the title compound as a white solid (2.8 mg, 13%). LCMS for $C_{22}H_{18}F_3N_6O_2$ (M+H)+: calculated m/z=455.1; found 455.1.

Example 19. N-(4-((2-(5-Methyl-1H-pyrazol-4-yl)-3-(trifluoromethyl)phenyl)amino)-5-oxo-5,6-dihydro-1,6-naphthyridin-2-yl)cyclopropanecarboxamide Trifluoroacetic Acid Salt

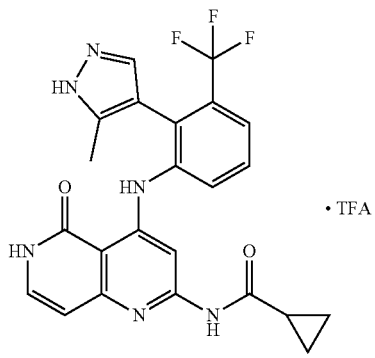 [SMILES: Cc1[nH]ncc1-c1c(Nc2cc(NC(=O)C3CC3)nc3cc[nH]c(=O)c23)cccc1C(F)(F)F]

The title compound was prepared according to the procedures described for Example 16, using 2-bromo-3-(trifluoromethyl)aniline (150 mg, 0.63 mmol, Enamine EN300-119908) in place of 2-bromo-3-chloroaniline and 3-methyl-4-(4,4,5,5-tetramethyl-1,3,2-dioxaborolan-2-yl)-1H-pyrazole (0.20 g, 0.94 mmol, AstaTech 82902) in place of 4-(4,4,5,5-tetramethyl-1,3,2-dioxaborolan-2-yl)-1H-pyrazole in Step 1. Purification via preparative HPLC-MS (pH=2) afforded the title compound as a white solid (3.3 mg, 13%). LCMS for $C_{23}H_{20}F_3N_6O_2$ (M+H)$^+$: calculated m/z=469.2; found 469.1.

Example 20. N-(4-((2-(Difluoromethoxy)phenyl)amino)-5-oxo-5,6-dihydro-1,6-naphthyridin-2-yl)cyclopropanecarboxamide Trifluoroacetic Acid Salt

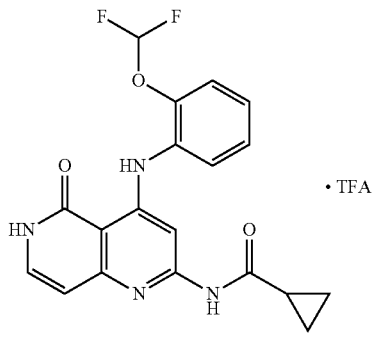 [SMILES: O=C(Nc1cc(Nc2ccccc2OC(F)F)c2c(=O)[nH]ccc2n1)C1CC1]

Step 1. 2-Chloro-4-((2-(difluoromethoxy)phenyl)amino)-1,6-naphthyridin-5(6H)-one

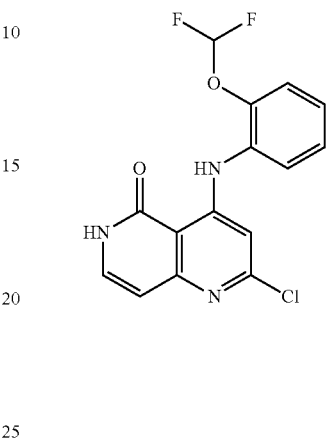

To a solution of 2,4-dichloro-1,6-naphthyridin-5(6H)-one (40.0 mg, 0.19 mmol, from Example 1, Step 1) and 2-(difluoromethoxy)aniline (30.0 mg, 0.19 mmol, Aldrich 470120) in THF (2.0 mL) at 0° C. was added a solution of LiHMDS (1.0 M in THF, 0.56 mL, 0.56 mmol) in a dropwise manner. The reaction was stirred for 25 min, then was quenched by the addition of saturated NH$_4$Cl solution (1 mL) at 0° C. The reaction was diluted with water (5.0 mL) and the layers were separated. The aqueous layer was extracted with EtOAc (2×). The combined organic extracts were dried over Na$_2$SO$_4$, filtered and concentrated. The residue was purified on a 12 g silica gel column, eluting with a gradient of 0-100% EtOAc in hexanes, to afford the title compound as an oil (50.0 mg, 80%). LCMS for $C_{15}H_{11}ClF_2N_3O_2$ (M+H)$^+$: calculated m/z=338.1; found 338.0.

Step 2. N-(4-((2-(Difluoromethoxy)phenyl)amino)-5-oxo-5,6-dihydro-1,6-naphthyridin-2-yl)cyclopropanecarboxamide Trifluoroacetic Acid Salt A mixture of 2-chloro-4-((2-(difluoromethoxy)phenyl)amino)-1,6-naphthyridin-5(6H)-one (50.0 mg, 0.15 mmol), cyclopropanecarboxamide (0.10 g, 1.2 mmol), 9,9-dimethyl-4,5-bis(diphenylphosphino)xanthene (15 mg, 0.025 mmol), tris(dibenzylideneacetone)dipalladium(0) (16 mg, 0.018 mmol), and Cs$_2$CO$_3$ (140 mg, 0.44 mmol) in dioxane (3.0 mL) was degassed by sparging with N$_2$, then the reaction vessel was sealed and heated at 120° C. for 3 hours. Upon cooling to room temperature, the reaction mixture was diluted with MeOH, filtered and purified via preparative HPLC-MS (pH=2) to afford the title compound as a white solid (17 mg, 30%). LCMS for $C_{19}H_{17}F_2N_4O_3$ (M+H)$^+$: calculated m/z=387.2; found 387.2. $^1$H NMR (400 MHz, DMSO-d$_6$) δ 11.86 (s, 1H), 11.84 (s, 1H), 11.28 (s, 1H), 7.63 (dd, J=7.7, 2.1 Hz, 1H), 7.54 (t, J=6.7 Hz, 1H), 7.44-7.30 (m, 4H), 7.24 (t, $^2J_{FH}$=73.5 Hz), 6.56 (d, J=7.3 Hz, 1H), 1.95 (m, 1H), 0.86 (m, 4H).

Example 21. N-(4-((2-Methoxyphenyl)amino)-5-oxo-5,6-dihydro-1,6-naphthyridin-2-yl)cyclopropanecarboxamide

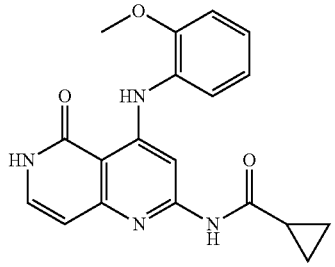 [SMILES: COc1ccccc1Nc1cc(NC(=O)C2CC2)nc2cc[nH]c(=O)c12]

The title compound was prepared according to the procedures described for Example 20, utilizing 2-methoxyaniline (Aldrich A88182) in place of 2-(difluoromethoxy)aniline in Step 1. Purification via preparative HPLC-MS (pH=10) afforded the title compound. LCMS for $C_{19}H_{19}N_4O_3$ (M+H)$^+$: calculated m/z=351.1; found 351.1.

Example 22. N-(4-((2-(Methylamino)phenyl)amino)-5-oxo-5,6-dihydro-1,6-naphthyridin-2-yl)cyclopropanecarboxamide Trifluoroacetic Acid Salt

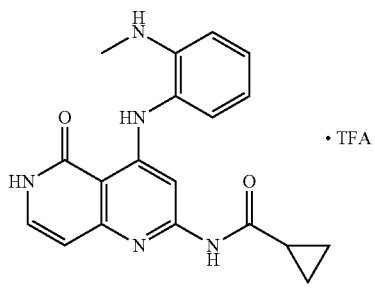 [SMILES: CNc1ccccc1Nc1cc(NC(=O)C2CC2)nc2cc[nH]c(=O)c12]

The title compound was prepared according to the procedures described for Example 20, utilizing M-methylbenzene-1,2-diamine (Combi-Blocks AN-3737) in place of 2-(difluoromethoxy)aniline in Step 1. Purification via preparative HPLC-MS (pH=2) afforded the title compound. LCMS for $C_{19}H_{20}N_5O_2$ (M+H)$^+$: calculated m/z=350.1; found 350.1. $^1$H NMR (400 MHz, DMSO-d$_6$) δ 12.19 (s, 1H), 11.54 (s, 1H), 11.43 (s, 1H), 7.68 (t, J=6.9 Hz, 1H), 7.31-7.21 (m, 1H), 7.14 (dd, J=7.7, 1.5 Hz, 1H), 6.77-6.66 (m, 3H), 6.47 (s, 1H), 2.70 (s, 3H), 2.02-1.58 (m, 1H), 1.09-0.64 (m, 4H).

Example 23. N-(4-((2-(Hydroxymethyl)phenyl)amino)-5-oxo-5,6-dihydro-1,6-naphthyridin-2-yl)cyclopropanecarboxamide Trifluoroacetic Acid Salt

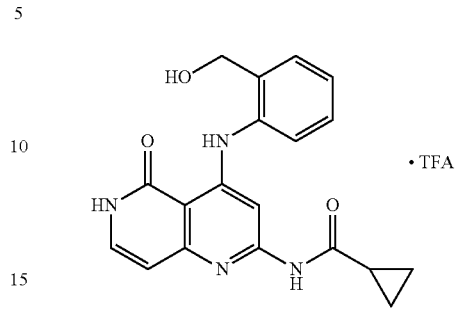

The title compound was prepared according to the procedures described for Example 20, utilizing (2-aminophenyl)methanol (Aldrich 122831) in place of 2-(difluoromethoxy)aniline in Step 1. Purification via preparative HPLC-MS (pH=2) afforded the title compound. LCMS for $C_{19}H_{19}N_4O_3$ (M+H)$^+$: calculated m/z=351.1; found 350.9. $^1$H NMR (500 MHz, 330 K, DMSO-d$_6$) δ 11.46 (s, 2H), 10.78 (s, 1H), 7.56 (d, J=7.6 Hz, 1H), 7.45-7.34 (m, 3H), 7.30 (t, J=7.3 Hz, 1H), 7.25 (s, 1H), 6.45 (d, J=7.3 Hz, 1H), 4.49 (s, 2H), 2.00-1.91 (m, 1H), 0.83-0.77 (m, 4H).

Example 24. N-(4-((2-Cyclopropoxyphenyl)amino)-5-oxo-5,6-dihydro-1,6-naphthyridin-2-yl)cyclopropanecarboxamide Trifluoroacetic Acid Salt

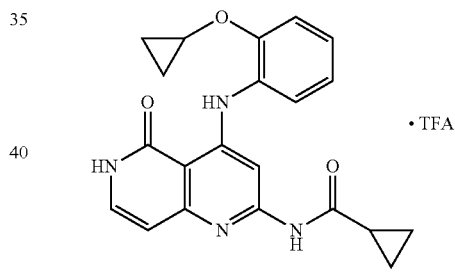

Step 1. 1-Cyclopropoxy-2-nitrobenzene

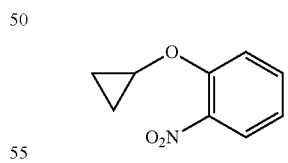

A mixture of 1-fluoro-2-nitrobenzene (350 mg, 2.5 mmol, Aldrich F10802), cyclopropanol (170 mg, 3.0 mmol, Combi-Blocks OT-0899) and Cs$_2$CO$_3$ (1.6 g, 5.0 mmol) in DMF (5.0 mL) was heated at 70° C. overnight. Upon cooling to room temperature, the reaction mixture was diluted with water and extracted with EtOAc. The organic layer was washed with brine, dried over MgSO$_4$, filtered and concentrated. The residue was purified on a 24 g silica gel column, eluting with a gradient of 0-80% EtOAc in hexanes, to afford the title compound as a clear oil (0.40 g, 90%). LCMS for $C_9H_{10}NO_3$ (M+H)$^+$: calculated m/z=180.1; found 180.0.

Step 2. 2-Cyclopropoxyaniline

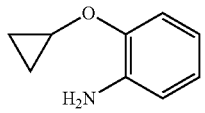 [SMILES: O=[N+]([O-])c1ccccc1OC1CC1]

A mixture of 1-cyclopropoxy-2-nitrobenzene (0.20 g, 1.1 mmol), zinc (730 mg, 11 mmol) and ammonium chloride (0.60 g, 11 mmol) in ethanol (4.0 mL) and water (1.0 mL) was stirred at room temperature for 1 h, then was heated to 70° C. for 1 h. Upon cooling to room temperature, the reaction mixture was diluted with DCM (10.0 mL) and filtered. The filtrate was washed with brine. The aqueous layer was back extracted with DCM. The combined organic extracts were dried over $Na_2SO_4$, filtered, and concentrated to afford the title compound as a white semi solid, which was used without further purification (0.10 g, 60%). LCMS for $C_9H_{12}NO$ $(M+H)^+$: calculated m/z=150.1; found 150.0.

Step 3. N-(4-((2-Cyclopropoxyphenyl)amino)-5-oxo-5,6-dihydro-1,6-naphthyridin-2-yl)cyclopropanecarboxamide Trifluoroacetic Acid Salt The title compound was prepared according to the procedures described for Example 20, utilizing 2-cyclopropoxyaniline in place of 2-(difluoromethoxy)aniline in Step 1. Purification via preparative HPLC-MS (pH=2) afforded the title compound. LCMS for $C_{21}H_{21}N_4O_3$ $(M+H)^+$: calculated m/z=377.1; found 377.1. $^1H$ NMR (400 MHz, DMSO-$d_6$) δ 11.88 (s, 1H), 11.69 (s, 1H), 11.25 (s, 1H), 7.59-7.49 (m, 1H), 7.48-7.42 (m, 2H), 7.29 (t, J=7.8 Hz, 1H), 7.24 (br, 1H), 7.12-7.03 (m, 1H), 6.57 (d, J=7.3 Hz, 1H), 3.95 (tt, J=6.0, 2.9 Hz, 1H), 1.93 (tt, J=7.5, 4.2 Hz, 1H), 0.97-0.83 (m, 4H), 0.83-0.75 (m, 2H), 0.70-0.60 (m, 2H).

Example A. JAK2 LanthaScreen JH1 Binding Assay

JAK2 JH1 binding assay utilizes catalytic domain (JH1, amino acids 826-1132) of human JAK2 expressed as N-terminal FLAG-tagged, biotinylated protein in a baculovirus expression system (Carna Biosciences, Product #08-445-20N). The assay was conducted in black 384-well polystyrene plates in a final reaction volume of 20 μL. JAK2 JH1 (1.5 nM) was incubated with compounds (100 nL serially diluted in DMSO) in the presence of 50 nM fluorescent JAK2-JH1 tracer and 0.5 nM Streptavidin-Tb cryptate (Cisbio Part #610SATLB) in assay buffer (50 mM Tris, pH=7.5, 10 mM $MgCl_2$, 0.01% Brij-35, 0.1% BSA, 1 mM EGTA, 5% Glycerol and 5 mM DTT). Non-specific binding was accessed in the presence of 2 mM ATP. After incubation for 2 hours at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example B. JAK2 LanthaScreen JH2-WT Binding Assay

JAK2 JH2-WT binding assay utilizes pseudo-kinase domain (JH2, amino-acids 536-812 with 3 surface mutations W659A, W777A, F794H) of human Wild Type JAK2 expressed as C-terminal His-Avi-tagged, biotinylated protein in a baculovirus expression system (BPS Bioscience, Catalog #79463). The assay was conducted in black 384-well polystyrene plates in a final reaction volume of 20 μL. JAK2 JH2-WT (0.145 nM) was incubated with compounds (100 nL serially diluted in DMSO) in the presence of 50 nM Fluorescent JAK2-JH2 Tracer (MedChem Express Catalog #HY-102055) and 0.25 nM Streptavidin-Tb cryptate (Cisbio Part #610SATLB) in assay buffer (50 mM Tris, pH=7.5, 10 mM $MgCl_2$, 0.01% Brij-35, 0.1% BSA, 1 mM EGTA, 5% Glycerol and 5 mM DTT). Non-specific binding was accessed in the presence of 2 mM ATP. After incubation for 1 hour at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example C. JAK2 LanthaScreen JH2-V617F Binding Assay

JAK2 JH2-V617F binding assay utilizes pseudo-kinase domain (JH2, amino-acids 536-812 with 3 surface mutations W659A, W777A, F794H) of human V617F mutant JAK2 expressed as C-terminal His-Avi-tagged, biotinylated protein in a baculovirus expression system (BPS Bioscience, Catalog #79498). The assay was conducted in black 384-well polystyrene plates in a final reaction volume of 20 μL. JAK2 JH2-V617F (0.26 nM) was incubated with compounds (100 nL serially diluted in DMSO) in the presence of 50 nM Fluorescent JAK2-JH2 Tracer (MedChem Express Catalog #HY-102055) and 0.25 nM Streptavidin-Tb cryptate (Cisbio Part #610SATLB) in assay buffer (50 mM Tris, pH=7.5, 10 mM $MgCl_2$, 0.01% Brij-35, 0.1% BSA, 1 mM EGTA, 5% Glycerol and 5 mM DTT). Non-specific binding was accessed in the presence of 2 mM ATP. After incubation for 1 hour at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example D. JAK2 HTRF Enzyme Activity Assay

JAK2 enzyme activity assays utilize catalytic domain (JH1, amino acids 808-1132) of human JAK2 expressed as N-terminal His-tagged protein in a baculovirus expression system (BPS Bioscience, Catalog #40450). The assays was conducted in black 384-well polystyrene plates in a final reaction volume of 20 μL. JAK2 (0.015 nM) was incubated with compounds (100 nL serially diluted in DMSO) in the presence of ATP (30 μM or 1 mM) and 500 nM Biotin-labeled EQEDEPEGDYFEWLE (SEQ ID NO.: 1) peptide (BioSource International, custom synthesis) in assay buffer (50 mM Tris, pH=7.5, 10 mM $MgCl_2$, 0.01% Brij-35, 0.1% BSA, 1 mM EGTA, 5% Glycerol and 5 mM DTT) for 60 minutes at 25° C. The reactions were stopped by the addition of 10 μL of detection buffer (50 mM Tris, pH 7.8, 0.5 mg/mL BSA, 150 mM NaCl), supplemented with EDTA, LANCE Eu-W1024 anti-phosphotyrosine (PY20), (PerkinElmer, Catalog #AD0067) and Streptavidin SureLight APC (PerkinElmer Catalog #CR130-100), for a final concentration of 15 mM, 1.5 nM and 75 nM, respectively. HTRF signals were read after 30 minutes incubation at room temperature on a PHERAstar FS plate reader (BMG LABTECH). Data was analyzed with IDBS XLfit and GraphPad Prism 5.0 software using a four parameter dose response curve to determine IC50 for each compound.

The compounds of the disclosure were tested in one or more of the assays described in Examples N-D, and the resulting data are shown in Table A.

TABLE A

| Ex. No. | JH1BIND $IC_{50}$ (nM) | JH2BIND_WT $IC_{50}$ (nM) | JH2BINDING_V617F $IC_{50}$ (nM) | ENZ 30UMATP $IC_{50}$ (nM) |
|---|---|---|---|---|
| 1 | ++++ | + | ++ | ++++ |
| 2 | +++++ | + | + | +++++ |
| 3 | +++++ | ++ | ++ | +++++ |
| 4 | ++++ | ++ | ++ | +++++ |
| 5 | +++++ | + | + | +++++ |
| 6 | ++++ | +++++ | +++++ | ++++ |
| 7 | ++++ | ++++ | +++++ | ++++ |
| 8 | ++++ | + | + | ++ |
| 9 | +++++ | ++++ | ++++ | +++++ |
| 10 | +++++ | ++++ | ++++ | +++++ |
| 11 | +++++ | ++++ | ++++ | +++++ |
| 12 | +++++ | +++ | +++ | +++++ |
| 13 | +++++ | ++++ | ++++ | +++++ |
| 14 | +++++ | ++ | ++ | +++++ |
| 15 | ++++ | ++ | +++ | ++++ |
| 16 | ++++ | +++ | +++ | ++++ |
| 17 | ++++ | +++ | ++++ | ++++ |
| 18 | +++++ | +++ | +++ | +++++ |
| 19 | +++++ | ++++ | ++++ | +++++ |
| 20 | ++++ | ++++ | ++++ | ++++ |
| 21 | ++++ | ++++ | +++++ | ++++ |
| 22 | +++++ | +++++ | +++++ | +++++ |
| 23 | ++++ | ++++ | +++++ | ++++ |
| 24 | ++++ | ++++ | ++++ | +++ |

+ refers to $IC_{50}$ of ≤100 nM
++ refers to $IC_{50}$ of >100 nM to ≤500 nM
+++ refers to $IC_{50}$ of >500 nM to ≤1000 nM
++++ refers to $IC_{50}$ of >1000 nM to ≤10000 nM
+++++ refers to $IC_{50}$ of >10000 nM

Example E. Cell Culture and STAT5 (Tyr694) Phosphorylation Cell Based Assay

Ba/F3 cells expressing human JAK2 V617F/EPOR (mouse JAK2 WT knocked out by CRISPR) are cultured in RPMI media with 10% FBS, 1 μg/mL Puromycin, 1 mg/mL Geneticin (Thermo Fisher). Ba/F3 cells expressing human JAK2 WT/EPOR are cultured in RPMI media with 10% FBS, 1 μg/mL Puromycin, 1 mg/mL Geneticin and 2 ng/mL EPO. 24 hours before the assay, the culture medium for JAK2 V617F/EPOR Ba/F3 cells are changed to RPMI with 10% FBS without antibiotic (assay medium 1). Culture medium for Ba/F3 cells expressing human JAK2 WT/EPOR are changed to RPMI with 10% FBS and 2 ng/mL EPO (R&D systems) without antibiotic (assay medium 2). 50 nL/well test compounds in DMSO are transferred to the 384 white low volume cell culture plate (Greiner Bio-one) by ECHO liquid handler (Labcyte). The cells are centrifuged, resuspended in the corresponding fresh assay medium and dispensed at 10 μL/well ($6\times10^6$ cells/mL) with 0.5% DMSO in the final assay. After the treated cells are incubated at 37° C., 5% $CO_2$ for 2 hours, 4 μl/well supplemented lysis buffer (100× blocking buffer diluted 25 fold in 4× lysis buffer, Perkin-Elmer) are added and incubated at room temperature for 60 min with gentle shaking on orbital shaker at 600 rpm. Phospho-STAT5 Cryptate antibody and Phospho-STAT5 d2 antibody (1:1 vol/vol, Perkin-Elmer) are premixed and diluted 20 fold within the detection buffer. 4 μL of the premixed antibody solution are added to each well followed with 16 hours incubation at room temperature. The product activity is determined by measuring the fluorescence at 620 nm and 665 nm on Pherastar microplate reader (BMG Labtech). A ratio is calculated (665/620 nm) for each well. Wells with DMSO serve as the positive controls and wells containing high concentration of control compound are used as negative controls. $IC_{50}$ determination is performed by fitting the curve of percent control activity versus the log of the compound concentration using the Genedata Screener software.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula I:

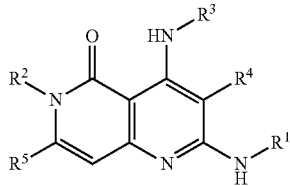

or a pharmaceutically acceptable salt thereof, wherein:
$R^1$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a1}$, $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{1A}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{c1}$ and $R^{d1}$ are each optionally substituted with 1, 2, 3, 4, 5, 6, 7, or 8 independently selected $R^{1A}$ substituents;

or, any $R^{c1}$ and $R^{d1}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{1A}$ substituents;

each $R^{b1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b1}$ are each optionally substituted with 1, 2, 3, 4, 5, 6, 7, or 8 independently selected $R^{1A}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{1A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)R^{b11}$, $NR^{c11}S(O)NR^{c11}R^{d11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, $OS(O)_2R^{b11}$, $SF_5$, $P(O)R^{f11}R^{g11}$, $OP(O)(OR^{h11})(OR^{i11})$, $P(O)(OR^{h11})(OR^{i11})$, and $BR^{j11}R^{k11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, 4, 5, 6, 7, or 8 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{c11}$ and $R^{d11}$ are each optionally substituted with 1, 2, 3, 4, 5, 6, 7, or 8 independently selected $R^{1B}$ substituents;

or, any $R^{c11}$ and $R^{d11}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{1B}$ substituents;

each $R^{b11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b11}$ are each optionally substituted with 1, 2, 3, 4, 5, 6, 7, or 8 independently selected $R^{1B}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f11}$ and $R^{g11}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h11}$ and $R^{i11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j11}$ and $R^{k11}$ is independently selected from OH, $C_{1-6}$ alkoxy, and $C_{1-6}$ haloalkoxy;

or any $R^{j11}$ and $R^{k11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1B}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)NR^{c12}R^{d12}$, $C(=NR^{e12})R^{b12}$, $C(=NR^{e12})NR^{c12}R^{d12}$, $NR^{c12}C(=NR^{e12})NR^{c12}R^{d12}$, $NR^{c12}C(=NR^{e12})R^{b12}$, $NR^{c12}S(O)R^{b12}$, $NR^{c12}S(O)NR^{c12}R^{d12}$, $NR^{c12}S(O)_2R^{b12}$, $NR^{c12}S(O)(=NR^{e12})R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, $OS(O)(=NR^{e12})R^{b12}$, and $OS(O)_2R^{b12}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{1B}$ are each optionally substituted with 1, 2, 3, or 4 independently selected $R^M$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{a12}$, $R^{c12}$ and $R^{d12}$ are each optionally substituted with 1, 2, 3, or 4 independently selected $R^M$ substituents;

or, any $R^{c12}$ and $R^{d12}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b12}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{b12}$ are each optionally substituted with 1, 2, 3, or 4 independently selected $R^M$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

$R^2$ is selected from H, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $C(=NR^{e2})R^{b2}$, $C(=NR^{e2})NR^{c2}R^{d2}$, $NR^{c2}R^{d2}$, $S(O)R^{b2}$, $S(O)NR^{c2}R^{d2}$, $S(O)_2R^{b2}$, and $S(O)_2NR^{c2}R^{d2}$, wherein the $C_{1-6}$ alkyl, $C_{2-6}$ alkenyl, and $C_{2-6}$ alkynyl of $R^2$ are each optionally substituted with 1, 2, 3, 4, 5, 6, 7, or 8 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, of $R^{a2}$, $R^{c2}$ and $R^{d2}$ are each optionally substituted with 1, 2, 3, 4, 5, 6, 7, or 8 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{2A}$ is independently selected from D, halo, oxo, $C_{1-6}$ alkyl, $C_{1-6}$ haloalkyl, $C_{2-6}$ alkenyl, $C_{2-6}$ alkynyl, CN, $NO_2$, $OR^{a21}$, $C(O)R^{b21}$, $C(O)NR^{c21}R^{d21}$, $C(O)OR^{a21}$, $C(=NR^{e21})R^{b21}$, $C(=NR^{e21})NR^{c21}R^{d21}$, $S(O)R^{b21}$, $S(O)NR^{c21}R^{d21}$, $S(O)_2R^{b21}$, and $S(O)_2NR^{c21}R^{d21}$, wherein the $C_{1-6}$ alkyl, $C_{2-6}$ alkenyl, and $C_{2-6}$ alkynyl of $R^{2A}$ are each optionally substituted with 1, 2, 3, or 4 independently selected $R^M$ substituents;

each $R^{a21}$, $R^{b21}$, $R^{c21}$, and $R^{d21}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl, of $R^{a21}$, $R^{c21}$ and $R^{d21}$ are each optionally substituted with 1, 2, 3, or 4 independently selected $R^M$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

$R^3$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a3}$, $C(O)R^{b3}$, $C(O)NR^{c3}R^{d3}$, $C(O)OR^{a3}$, $C(=NR^{e3})R^{b3}$, $C(=NR^{e3})NR^{c3}R^{d3}$, $S(O)R^{b3}$, $S(O)NR^{c3}R^{d3}$, $S(O)_2R^{b3}$, and $S(O)_2NR^{c3}R^{d3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, 4, 5, 6, 7, or 8 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, 4, 5, 6, 7, or 8 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, 4, 5, 6, 7, or 8 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $NHOR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}NR^{c31}R^{d31}$, $NR^{c31}C(O)R^{b31}$, $NR^{c31}C(O)OR^{a31}$, $NR^{c31}C(O)NR^{c31}R^{d31}$, $C(=NR^{e31})R^{b31}$, $C(=NR^{e31})NR^{c31}R^{d31}$, $NR^{c31}C(=NR^{e31})NR^{c31}R^{d31}$, $NR^{c31}C(=NR^{e31})R^{b31}$, $NR^{c31}S(O)R^{b31}$, $NR^{c31}S(O)NR^{c31}R^{d31}$, $NR^{c31}S(O)_2R^{b31}$, $NR^{c31}S(O)(=NR^{e31})R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, $OS(O)(=NR^{e31})R^{b31}$, $OS(O)_2R^{b31}$, $SF_5$, $P(O)R^{f31}R^{g31}$, $OP(O)(OR^{h31})(OR^{i31})$, $P(O)(OR^{h31})(OR^{i31})$, and $BR^{j31}R^{k31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, 4, 5, 6, 7, or 8 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, 4, 5, 6, 7, or 8 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, 4, 5, 6, 7, or 8 independently selected $R^{3B}$ substituents;

each $R^{e31}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f31}$ and $R^{g31}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h31}$ and $R^{i31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j31}$ and $R^{k31}$ is independently selected from OH, $C_{1-6}$ alkoxy, and $C_{1-6}$ haloalkoxy;

or any $R^{j31}$ and $R^{k31}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{3B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $NHOR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}NR^{c32}R^{d32}$, $NR^{c32}C(O)R^{b32}$, $NR^{c32}C(O)OR^{a32}$, $NR^{c32}C(O)NR^{c32}R^{d32}$, $C(=NR^{e32})R^{b32}$, $C(=NR^{e32})NR^{c32}R^{d32}$, $NR^{c32}C(=NR^{e32})NR^{c32}R^{d32}$, $NR^{c32}C(=NR^{e32})R^{b32}$, $NR^{c32}S(O)R^{b32}$, $NR^{c32}S(O)NR^{c32}R^{d32}$, $NR^{c32}S(O)_2R^{b32}$, $NR^{c32}S(O)(=NR^{e32})R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, $OS(O)(=NR^{e32})R^{b32}$, $OS(O)_2R^{b32}$, $SF_5$, $P(O)R^{f32}R^{g32}$, $OP(O)(OR^{h32})(OR^{i32})$, $P(O)(OR^{h32})(OR^{i32})$, and $BR^{j32}R^{k32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, 4, 5, 6, 7, or 8 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, 4, 5, 6, 7, or 8 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, 4, 5, 6, 7, or 8 independently selected $R^{3C}$ substituents;

each $R^{e32}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{f32}$ and $R^{g32}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h32}$ and $R^{i32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j32}$ and $R^{k32}$ is independently selected from OH, $C_{1-6}$ alkoxy, and $C_{1-6}$ haloalkoxy;

or any $R^{j32}$ and $R^{k32}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{3C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $NHOR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}NR^{c33}R^{d33}$, $NR^{c33}C(O)R^{b33}$, $NR^{c33}C(O)OR^{a33}$, $NR^{c33}C(O)NR^{c33}R^{d33}$, $C(=NR^{e33})R^{b33}$, $C(=NR^{e33})NR^{c33}R^{d33}$, $NR^{c33}C(=NR^{e33})NR^{c33}R^{d33}$, $NR^{c33}C(=NR^{e33})R^{b33}$, $NR^{c33}S(O)R^{b33}$, $NR^{c33}S(O)NR^{c33}R^{d33}$, $NR^{c33}S(O)_2R^{b33}$, $NR^{c33}S(O)(=NR^{e33})R^{b33}$, $NR^{c33}S(O)_2NR^{c33}R^{d33}$, $S(O)R^{b33}$, $S(O)NR^{c33}R^{d33}$, $S(O)_2R^{b33}$, $S(O)_2NR^{c33}R^{d33}$, $OS(O)(=NR^{e33})R^{b33}$, and $OS(O)_2R^{b33}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{3C}$ are each optionally substituted with 1, 2, 3, or 4 independently selected $R^M$ substituents;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a33}$, $R^{c33}$ and $R^{d33}$ are each optionally substituted with 1, 2, 3, or 4 independently selected $R^M$ substituents;

or, any $R^{c33}$ and $R^{d33}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b33}$ are each optionally substituted with 1, 2, 3, or 4 independently selected $R^M$ substituents;

each $R^{e33}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$;

$R^5$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$; and each $R^M$ is independently selected from H, D, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

2. The compound of claim 1, or a pharmaceutically acceptable salt thereof, wherein $R^1$ is selected from C(O)$R^{b1}$, C(O)N$R^{c1}R^{d1}$, C(O)O$R^{a1}$, C(=N$R^{e1}$)$R^{b1}$, C(=N$R^{e1}$)N$R^{c1}R^{d1}$, S(O)$R^{b1}$, S(O)N$R^{c1}R^{d1}$, S(O)$_2R^{b1}$, and S(O)$_2$N$R^{c1}R^{d1}$.

3. The compound of claim 1, or a pharmaceutically acceptable salt thereof, wherein $R^1$ is C(O)$R^{b1}$.

4. The compound of claim 1, or a pharmaceutically acceptable salt thereof, wherein $R^{a1}$, $R^{c1}$, and $R^{d1}$ are each independently selected from phenyl, $C_{3-6}$ cycloalkyl, 5-6 membered heteroaryl, and 4-6 membered heterocycloalkyl.

5. The compound of claim 1, or a pharmaceutically acceptable salt thereof, wherein $R^{b1}$ is selected from phenyl, $C_{3-6}$ cycloalkyl, 5-6 membered heteroaryl, and 4-6 membered heterocycloalkyl.

6. The compound of claim 1, or a pharmaceutically acceptable salt thereof, wherein $R^1$ is cyclopropylcarbonyl.

7. The compound of claim 1, or a pharmaceutically acceptable salt thereof, wherein $R^2$ is selected from H, $C_{1-6}$ alkyl, $C_{1-6}$ haloalkyl, $C_{2-6}$ alkenyl, and $C_{2-6}$ alkynyl.

8. The compound of claim 1, or a pharmaceutically acceptable salt thereof, wherein $R^2$ is H or $C_{1-6}$ alkyl.

9. The compound of claim 1, or a pharmaceutically acceptable salt thereof, wherein $R^2$ is H or methyl.

10. The compound of claim 1, or a pharmaceutically acceptable salt thereof, wherein $R^3$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, or 4 independently selected $R^{3A}$ substituents.

11. The compound of claim 1, or a pharmaceutically acceptable salt thereof, wherein $R^3$ is selected from phenyl and 5-10 membered heteroaryl, wherein the phenyl and 5-10 membered heteroaryl of $R^3$ are each optionally substituted with 1, 2, 3, or 4 independently selected $R^{3A}$ substituents.

12. The compound of claim 1, or a pharmaceutically acceptable salt thereof, wherein $R^3$ is selected from phenyl and indolyl, wherein the phenyl and indolyl of $R^3$ are each optionally substituted with 1, 2, 3, or 4 independently selected $R^{3A}$ substituents.

13. The compound of claim 1, or a pharmaceutically acceptable salt thereof, wherein each $R^{3A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{c31}C(O)NR^{c31}R^{d31}$, $S(O)R^{b31}$, $S(O)NR^{c31}R^{d31}$, $S(O)_2R^{b31}$, and $S(O)_2NR^{c31}R^{d31}$, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents.

14. The compound of claim 1, or a pharmaceutically acceptable salt thereof, wherein each $R^{3A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $OR^{a31}$, $SR^{a31}$, $C(O)R^{b31}$, $C(O)NR^{c31}R^{d31}$, $C(O)OR^{a31}$, $NR^{c31}R^{d31}$, $S(O)R^{b31}$, $S(O)NR^{c31}R^{d31}$, $S(O)_2R^{b31}$, and $S(O)_2NR^{c31}R^{d31}$, wherein the $C_{1-6}$ alkyl, $C_{6-10}$ aryl, $C_{3-10}$ cycloalkyl, 5-10 membered heteroaryl, and 4-10 membered heterocycloalkyl of $R^{3A}$ are each optionally substituted with 1, 2, 3, or 4 independently selected $R^{3B}$ substituents.

15. The compound of claim 1, or a pharmaceutically acceptable salt thereof, wherein each $R^{3A}$ is independently selected from halo, $C_{1-6}$ alkyl, $C_{1-6}$ haloalkyl, 5-10 membered heteroaryl, 4-10 membered heterocycloalkyl, $OR^{a31}$, $SR^{a31}$, $C(O)NR^{c31}R^{d31}$, $NR^{c31}R^{d31}$, and $S(O)_2R^{b31}$, wherein the $C_{1-6}$ alkyl, 5-10 membered heteroaryl, and 4-10 membered heterocycloalkyl of $R^{3A}$ are each optionally substituted with 1, 2, 3, or 4 independently selected $R^{3B}$ substituents.

16. The compound of claim 1, or a pharmaceutically acceptable salt thereof, wherein each $R^{3A}$ is independently selected from halo, $C_{1-6}$ alkyl, $C_{1-6}$ haloalkyl, 5-6 membered heteroaryl, 4-6 membered heterocycloalkyl, $OR^{a31}$, $SR^{a31}$, $C(O)NR^{c31}R^{d31}$, $NR^{c31}R^{d31}$, and $S(O)_2R^{b31}$, wherein the $C_{1-6}$ alkyl, 5-6 membered heteroaryl, and 4-6 membered heterocycloalkyl of $R^{3A}$ are each optionally substituted with 1, 2, 3, or 4 independently selected $R^{3B}$ substituents.

17. The compound of claim 1, or a pharmaceutically acceptable salt thereof, wherein $R^{a31}$, $R^{b31}$, $R^{c31}$, and $R^{d31}$ are each independently selected from H, $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{a31}$, $R^{b31}$, $R^{c31}$, and $R^{d31}$ are each optionally substituted with 1, 2, 3, or 4 independently selected $R^{3B}$ substituents.

18. The compound of claim 1, or a pharmaceutically acceptable salt thereof, wherein $R^{a31}$, $R^{b31}$, $R^{c31}$, and $R^{d31}$ are each independently selected from H, $C_{1-6}$ alkyl, $C_{1-6}$ haloalkyl, $C_{3-6}$ cycloalkyl, and (4-6 membered heterocycloalkyl)-$C_{1-6}$ alkyl-, wherein the $C_{1-6}$ alkyl of $R^{a31}$, $R^{b31}$, $R^{c31}$, and $R^{d31}$ is optionally substituted with 1 or 2 OH groups.

19. The compound of claim 1, or a pharmaceutically acceptable salt thereof, wherein $R^{a31}$, $R^{b31}$, $R^{c31}$, and $R^{d31}$ are each independently selected from H, methyl, hydroxymethyl, difluoromethyl, cyclopropyl, and tetrahydropyranylmethyl.

20. The compound of claim 1, or a pharmaceutically acceptable salt thereof, wherein each $R^{3A}$ is independently selected from chloro, ethyl, trifluoromethyl, hydroxymethyl, pyrazolyl, thiazolyl, piperazinyl, methoxy, difluoromethoxy, cyclopropoxy, methylthio, methylsulfonyl, methylamino, tetrahydropyranylmethylaminocarbonyl, wherein the pyrazolyl, thiazolyl, and piperazinyl of $R^{3A}$ are each optionally substituted with 1 or 2 independently selected $R^{3B}$ substituents.

21. The compound of claim 1, or a pharmaceutically acceptable salt thereof, wherein each $R^{3B}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $S(O)R^{b32}$, $S(O)NR^{c32}R^{d32}$, $S(O)_2R^{b32}$, and $S(O)_2NR^{c32}R^{d32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{3B}$ are each optionally substituted with 1, 2, 3, or 4 independently selected $R^{3C}$ substituents.

22. The compound of claim 1, or a pharmaceutically acceptable salt thereof, wherein each $R^{3B}$ is independently selected from $C_{1-6}$ alkyl, $C_{6-10}$ aryl, $C_{3-10}$ cycloalkyl, 4-10 membered heterocycloalkyl, and $S(O)_2R^{b32}$, wherein the $C_{1-6}$ alkyl, $C_{6-10}$ aryl, $C_{3-10}$ cycloalkyl, and 4-10 membered heterocycloalkyl of $R^{3B}$ are each optionally substituted with 1, 2, 3, or 4 independently selected $R^{3C}$ substituents.

23. The compound of claim 1, or a pharmaceutically acceptable salt thereof, wherein each $R^{3B}$ is independently selected from $C_{1-6}$ alkyl, phenyl, $C_{3-6}$ cycloalkyl, 4-6 membered heterocycloalkyl, and $S(O)_2R^{b32}$, wherein the $C_{1-6}$ alkyl of $R^{3B}$ is optionally substituted with aminocarbonyl; and $R^{b32}$ is selected from phenyl and $C_{3-6}$ cycloalkyl.

24. The compound of claim 1, or a pharmaceutically acceptable salt thereof, wherein each $R^{3B}$ is independently selected from methyl, aminocarbonylethyl, tetrahydropyranyl, cyclopentyl, and cyclopropylsulfonyl.

25. The compound of claim 1, or a pharmaceutically acceptable salt thereof, wherein $R^4$ is selected from H, D, and $C_{1-6}$ alkyl.

26. The compound of claim 1, or a pharmaceutically acceptable salt thereof, wherein $R^4$ is H.

27. The compound of claim 1, or a pharmaceutically acceptable salt thereof, wherein $R^5$ is selected from H, D, and $C_{1-6}$ alkyl.

28. The compound of claim 1, or a pharmaceutically acceptable salt thereof, wherein $R^5$ is H.

29. The compound of claim 1, or a pharmaceutically acceptable salt thereof, wherein $R^4$ and $R^5$ are each H.

30. The compound of claim 1, or a pharmaceutically acceptable salt thereof, wherein:
   $R^1$ is selected from $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)R^{b1}$, $S(O)NR^{c1}R^{d1}$, $S(O)_2R^{b1}$, and $S(O)_2NR^{c1}R^{d1}$;
   $R^2$ is selected from H, $C_{1-6}$ alkyl, $C_{1-6}$ haloalkyl, $C_{2-6}$ alkenyl, and $C_{2-6}$ alkynyl;
   $R^3$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, or 4 independently selected $R^{3A}$ substituents;
   $R^4$ is selected from H, D, and $C_{1-6}$ alkyl; and
   $R^5$ is selected from H, D, and $C_{1-6}$ alkyl.

31. The compound of claim 1, or a pharmaceutically acceptable salt thereof, wherein:
   $R^1$ is selected from $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)R^{b1}$, $S(O)NR^{c1}R^{d1}$, $S(O)_2R^{b1}$, and $S(O)_2NR^{c1}R^{d1}$;
   $R^{a1}$, $R^{c1}$, and $R^{d1}$ are each independently selected from phenyl, $C_{3-6}$ cycloalkyl, 5-6 membered heteroaryl, and 4-6 membered heterocycloalkyl;
   $R^2$ is selected from H, $C_{1-6}$ alkyl, $C_{1-6}$ haloalkyl, $C_{2-6}$ alkenyl, and $C_{2-6}$ alkynyl;
   $R^3$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, or 4 independently selected $R^{3A}$ substituents;
   each $R^{3A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{c31}C(O)NR^{c31}R^{d31}$, $S(O)R^{b31}$, $S(O)NR^{c31}R^{d31}$, $S(O)_2R^{b31}$, and $S(O)_2NR^{c31}R^{d31}$, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents;

$R^{a31}$, $R^{b31}$, $R^{c31}$, and $R^{d31}$ are each independently selected from H, $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{a31}$, $R^{b31}$, $R^{c31}$, and $R^{d31}$ are each optionally substituted with 1, 2, 3, or 4 independently selected $R^{3B}$ substituents;

each $R^{3B}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $S(O)R^{b32}$, $S(O)NR^{c32}R^{d32}$, $S(O)_2R^{b32}$, and $S(O)_2NR^{c32}R^{d32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{3B}$ are each optionally substituted with 1, 2, 3, or 4 independently selected $R^{3C}$ substituents;

$R^4$ is selected from H, D, and $C_{1-6}$ alkyl; and
$R^5$ is selected from H, D, and $C_{1-6}$ alkyl.

32. The compound of claim 1, or a pharmaceutically acceptable salt thereof, wherein:

$R^1$ is $C(O)R^{b1}$;

$R^{b1}$ is selected from phenyl, $C_{3-6}$ cycloalkyl, 5-6 membered heteroaryl, and 4-6 membered heterocycloalkyl;

$R^2$ is H or $C_{1-6}$ alkyl;

$R^3$ is selected from phenyl and 5-10 membered heteroaryl, wherein the phenyl and 5-10 membered heteroaryl of $R^3$ are each optionally substituted with 1, 2, 3, or 4 independently selected $R^{3A}$ substituents;

each $R^{3A}$ is independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $OR^{a31}$, $SR^{a31}$, $C(O)R^{b31}$, $C(O)NR^{c31}R^{d31}$, $C(O)OR^{a31}$, $NR^{c31}R^{d31}$, $S(O)R^{b31}$, $S(O)NR^{c31}R^{d31}$, $S(O)_2R^{b31}$, and $S(O)_2NR^{c31}R^{d31}$, wherein the $C_{1-6}$ alkyl, $C_{6-10}$ aryl, $C_{3-10}$ cycloalkyl, 5-10 membered heteroaryl, and 4-10 membered heterocycloalkyl of $R^{3A}$ are each optionally substituted with 1, 2, 3, or 4 independently selected $R^{3B}$ substituents;

each $R^{a31}$, $R^{b31}$, $R^{c31}$, and $R^{d31}$ is independently selected from H, $C_{1-6}$ alkyl, $C_{1-6}$ haloalkyl, $C_{3-6}$ cycloalkyl, and (4-6 membered heterocycloalkyl)-$C_{1-6}$ alkyl-, wherein the $C_{1-6}$ alkyl of $R^{a31}$, $R^{b31}$, $R^{c31}$, and $R^{d31}$ is optionally substituted with 1 or 2 OH groups;

each $R^{3B}$ is independently selected from $C_{1-6}$ alkyl, $C_{6-10}$ aryl, $C_{3-10}$ cycloalkyl, 4-10 membered heterocycloalkyl, and $S(O)_2R^{b32}$, wherein the $C_{1-6}$ alkyl, $C_{6-10}$ aryl, $C_{3-10}$ cycloalkyl, and 4-10 membered heterocycloalkyl of $R^{3B}$ are each optionally substituted with 1, 2, 3, or 4 independently selected $R^{3C}$ substituents;

$R^4$ is selected from H, D, and $C_{1-6}$ alkyl; and
$R^5$ is selected from H, D, and $C_{1-6}$ alkyl.

33. The compound of claim 1, or a pharmaceutically acceptable salt thereof, wherein:

$R^1$ is cyclopropylcarbonyl;

$R^2$ is H or methyl;

$R^3$ is selected from phenyl and indolyl, wherein the phenyl and indolyl of $R^3$ are each optionally substituted with 1, 2, 3, or 4 independently selected $R^{3A}$ substituents;

each $R^{3A}$ is independently selected from chloro, ethyl, trifluoromethyl, hydroxymethyl, pyrazolyl, thiazolyl, piperazinyl, methoxy, difluoromethoxy, cyclopropoxy, methylthio, methylsulfonyl, methylamino, tetrahydropyranylmethylaminocarbonyl, wherein the pyrazolyl, thiazolyl, and piperazinyl of $R^{3A}$ are each optionally substituted with 1 or 2 independently selected $R^{3B}$ substituents;

each $R^{3B}$ is independently selected from $C_{1-6}$ alkyl, phenyl, $C_{3-6}$ cycloalkyl, 4-6 membered heterocycloalkyl, and $S(O)_2R^{b32}$, wherein the $C_{1-6}$ alkyl of $R^{3B}$ is optionally substituted with aminocarbonyl; and $R^{b32}$ is selected from phenyl and $C_{3-6}$ cycloalkyl;

$R^4$ is H; and $R^5$ is H.

34. The compound of claim 1, wherein the compound of Formula I is a compound of Formula II:

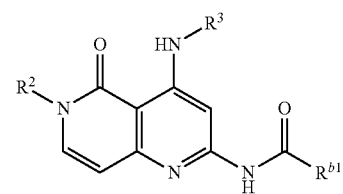

or a pharmaceutically acceptable salt thereof.

35. The compound of claim 1, wherein the compound of Formula I is a compound of Formula III:

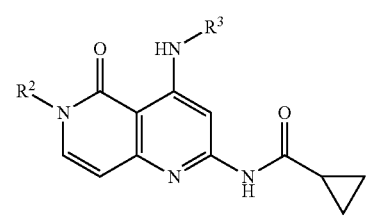

or a pharmaceutically acceptable salt thereof.

36. The compound of claim 1, wherein the compound of Formula I is a compound of Formula IV:

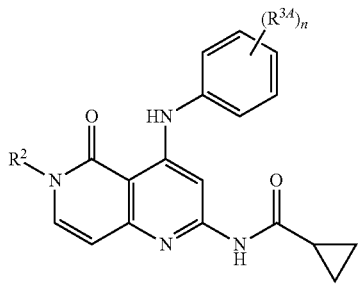

or a pharmaceutically acceptable salt thereof, wherein n is 0, 1, 2, 3 or 4.

37. The compound of claim 1, which is selected from:
N-(4-((2-methoxy-3-(1H-pyrazol-4-yl)phenyl)amino)-5-oxo-5,6-dihydro-1,6-naphthyridin-2-yl)cyclopropanecarboxamide;
N-(4-((2-methoxy-3-(2-(tetrahydro-2H-pyran-4-yl)thiazol-5-yl)phenyl)amino)-5-oxo-5,6-dihydro-1,6-naphthyridin-2-yl)cyclopropanecarboxamide;
N-(4-((3-(1-cyclopentyl-1H-pyrazol-4-yl)-2-methoxyphenyl)amino)-5-oxo-5,6-dihydro-1,6-naphthyridin-2-yl)cyclopropanecarboxamide;
N-(4-((3-(4-(cyclopropylsulfonyl)piperazin-1-yl)-2-methoxyphenyl)amino)-5-oxo-5,6-dihydro-1,6-naphthyridin-2-yl)cyclopropanecarboxamide;
N-(4-((2-methoxy-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide;
N-(5-oxo-4-((3-(1-(tetrahydro-2H-pyran-4-yl)-1H-pyrazol-4-yl)phenyl)amino)-5,6-dihydro-1,6-naphthyridin-2-yl)cyclopropanecarboxamide;
N-(4-((2-methoxy-4-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide;
N-(4-((3-(1-(1-amino-1-oxopropan-2-yl)-1H-pyrazol-4-yl)-2-methoxyphenyl)amino)-5-oxo-5,6-dihydro-1,6-naphthyridin-2-yl)cyclopropanecarboxamide;
N-(4-((1-ethyl-1H-indol-7-yl)amino)-5-oxo-5,6-dihydro-1,6-naphthyridin-2-yl)cyclopropanecarboxamide;
N-(4-((2-methoxy-3-(2-(tetrahydro-2H-pyran-4-yl)thiazol-5-yl)phenyl)amino)-6-methyl-5-oxo-5,6-dihydro-1,6-naphthyridin-2-yl)cyclopropanecarboxamide;
3-((2-(cyclopropanecarboxamido)-5-oxo-5,6-dihydro-1,6-naphthyridin-4-yl)amino)-2-methoxy-N-((tetrahydro-2H-pyran-4-yl)methyl)benzamide;
N-(4-((2-(methylthio)-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide;
N-(4-((2-(methylsulfonyl)-3-(1-(tetrahydro-2H-pyran-4-yl)-1H-pyrazol-4-yl)phenyl)amino)-5-oxo-5,6-dihydro-1,6-naphthyridin-2-yl)cyclopropanecarboxamide;
N-(4-((2-methoxy-3-(trifluoromethyl)phenyl)amino)-5-oxo-5,6-dihydro-1,6-naphthyridin-2-yl)cyclopropanecarboxamide;
N-(4-((2,3-dimethoxyphenyl)amino)-5-oxo-5,6-dihydro-1,6-naphthyridin-2-yl)cyclopropanecarboxamide;
N-(4-((3-chloro-2-(1H-pyrazol-4-yl)phenyl)amino)-5-oxo-5,6-dihydro-1,6-naphthyridin-2-yl)cyclopropanecarboxamide;
N-(4-((3-chloro-2-(5-methyl-1H-pyrazol-4-yl)phenyl)amino)-5-oxo-5,6-dihydro-1,6-naphthyridin-2-yl)cyclopropanecarboxamide;
N-(4-((2-(1H-pyrazol-4-yl)-3-(trifluoromethyl)phenyl)amino)-5-oxo-5,6-dihydro-1,6-naphthyridin-2-yl)cyclopropanecarboxamide;
N-(4-((2-(5-methyl-1H-pyrazol-4-yl)-3-(trifluoromethyl)phenyl)amino)-5-oxo-5,6-dihydro-1,6-naphthyridin-2-yl)cyclopropanecarboxamide;
N-(4-((2-(difluoromethoxy)phenyl)amino)-5-oxo-5,6-dihydro-1,6-naphthyridin-2-yl)cyclopropanecarboxamide;
N-(4-((2-methoxyphenyl)amino)-5-oxo-5,6-dihydro-1,6-naphthyridin-2-yl)cyclopropanecarboxamide;
N-(4-((2-(methylamino)phenyl)amino)-5-oxo-5,6-dihydro-1,6-naphthyridin-2-yl)cyclopropanecarboxamide;
N-(4-((2-(hydroxymethyl)phenyl)amino)-5-oxo-5,6-dihydro-1,6-naphthyridin-2-yl)cyclopropanecarboxamide; and
N-(4-((2-cyclopropoxyphenyl)amino)-5-oxo-5,6-dihydro-1,6-naphthyridin-2-yl)cyclopropanecarboxamide;
or a pharmaceutically acceptable salt thereof.

38. A pharmaceutical composition, comprising a compound of claim 1, or a pharmaceutically acceptable salt thereof, and a pharmaceutically acceptable carrier.

39. A method of inhibiting an activity of the V617F variant of JAK2 kinase, comprising contacting the kinase with a compound of claim 1, or a pharmaceutically acceptable salt thereof.

40. A method of treating a myeloproliferative disorder selected from polycythemia vera, essential thrombocythemia, myelofibrosis with myeloid metaplasia, primary myelofibrosis, post-essential thrombocythemia myelofibrosis, and post polycythemia vera myelofibrosis, in a patient in need thereof, the method comprising administering to the patient a therapeutically effective amount of a compound of claim 1, or a pharmaceutically acceptable salt thereof.

41. The method of claim 40, wherein the myeloproliferative disorder is polycythemia vera.

42. The method of claim 40, wherein the myeloproliferative disorder is essential thrombocythemia.

43. The method of claim 40, wherein the myeloproliferative disorder is myelofibrosis with myeloid metaplasia.

44. The method of claim 40, wherein the myeloproliferative disorder is primary myelofibrosis.

45. The method of claim 40, wherein the myeloproliferative disorder is post-essential thrombocythemia myelofibrosis.

46. The method of claim 40, wherein the myeloproliferative disorder is post polycythemia vera myelofibrosis.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Biotin-labeled peptide, custom synthesis

<400> SEQUENCE: 1

Glu Gln Glu Asp Glu Pro Glu Gly Asp Tyr Phe Glu Trp Leu Glu
1               5                   10                  15